US009057485B2

(12) United States Patent
Knox et al.

(10) Patent No.: US 9,057,485 B2
(45) Date of Patent: Jun. 16, 2015

(54) PARTICLE DETECTORS

(71) Applicant: Xtralis Technologies Ltd, Nassau, NP (BS)

(72) Inventors: Ron Knox, Victoria (AU); Karl Boettger, Mount Waverley (AU); Kemal Ajay, Mount Waverley (AU)

(73) Assignee: Xtralis Technologies Ltd (BS)

( * ) Notice: Subject to any disclaimer, the term of this patent is extended or adjusted under 35 U.S.C. 154(b) by 0 days.

(21) Appl. No.: 14/451,330

(22) Filed: Aug. 4, 2014

(65) Prior Publication Data

US 2014/0340892 A1 Nov. 20, 2014

Related U.S. Application Data

(62) Division of application No. 13/318,309, filed as application No. PCT/AU2010/000511 on May 3, 2010, now Pat. No. 8,797,531.

(30) Foreign Application Priority Data

May 1, 2009 (AU) ................................ 2009901922
May 1, 2009 (AU) ................................ 2009901923
May 1, 2009 (AU) ................................ 2009901924
May 1, 2009 (AU) ................................ 2009901925
May 1, 2009 (AU) ................................ 2009901926
May 1, 2009 (AU) ................................ 2009901927

(51) Int. Cl.
*G01N 21/00* (2006.01)
*F21K 99/00* (2010.01)
(Continued)

(52) U.S. Cl.
CPC ....... *F21K 9/00* (2013.01); *G01N 21/53* (2013.01); *G01N 2201/0627* (2013.01);
(Continued)

(58) Field of Classification Search
CPC ............... G02B 2027/0178; G02B 27/017; G02B 2027/014; G02B 27/0093; G02B 2027/0187; G02B 2027/0118; G02B 27/0172; G02B 5/30; G02B 2027/0138; G02B 27/0176; G02B 21/10; G02B 2027/0127; G02B 2027/0132
See application file for complete search history.

(56) References Cited

U.S. PATENT DOCUMENTS 3,982,130 A 9/1976 Trumble
4,156,816 A 5/1979 Lindgren
(Continued)

FOREIGN PATENT DOCUMENTS

GB 2319604 A 5/1998
JP 51-127786 A 11/1976
(Continued)

OTHER PUBLICATIONS

"Chinese Application Serial No. 200980130131.9, Office Action mailed Jul. 8, 2014", (English Translation), 14 pgs.
(Continued)

*Primary Examiner* — Michael P Stafira
(74) *Attorney, Agent, or Firm* — Schwegman Lundberg & Woessner, P.A.

(57) ABSTRACT

A beam detector including a light source, a receiver, and a target, acting in cooperation to detect particles in a monitored area. The target reflects incident light, resulting in reflected light being returned to receiver. The receiver is capable of recording and reporting light intensity at a plurality of points across its field of view. In the preferred form the detector emits a first light beam in a first wavelength band; a second light beam in a second wavelength band; and a third light beam in a third wavelength band, wherein the first and second wavelengths bands are substantially equal and are different to the third wavelength band.

8 Claims, 50 Drawing Sheets

(51) Int. Cl.
*G01N 21/53* (2006.01)
*G01N 15/02* (2006.01)
*G01N 15/14* (2006.01)
*G01N 15/10* (2006.01)

(52) U.S. Cl.
CPC . *G01N 2201/0633* (2013.01); *G01N 2201/062* (2013.01); *G01N 15/0205* (2013.01); *G01N 15/1459* (2013.01); *G01N 21/538* (2013.01); *G01N 15/10* (2013.01); *G01N 2201/061* (2013.01)

(56) References Cited

U.S. PATENT DOCUMENTS

| | | | |
|---|---|---|---|
| 4,348,111 | A | 9/1982 | Goulas et al. |
| 4,387,993 | A | 6/1983 | Adrian |
| 4,547,675 | A * | 10/1985 | Muggli et al. ............ 250/565 |
| 4,854,705 | A | 8/1989 | Bachalo |
| 4,857,895 | A * | 8/1989 | Kaprelian ............ 340/630 |
| 4,927,268 | A | 5/1990 | Carr |
| 4,928,153 | A | 5/1990 | Glass |
| 5,260,765 | A | 11/1993 | Hawkinson |
| 5,392,114 | A | 2/1995 | Cole |
| 5,451,931 | A * | 9/1995 | Muller et al. ............ 340/630 |
| 5,694,221 | A | 12/1997 | Knapp |
| 6,011,478 | A | 1/2000 | Suzuki et al. |
| 6,266,137 | B1 | 7/2001 | Morinaga |
| 7,292,338 | B2 | 11/2007 | Itagaki |
| 7,525,660 | B2 | 4/2009 | Gigioli et al. |
| 7,564,365 | B2 | 7/2009 | Marman et al. |
| 7,671,988 | B2 | 3/2010 | Dal Sasso et al. |
| 8,098,362 | B2 | 1/2012 | Kanaya |
| 8,339,598 | B2 | 12/2012 | Ban et al. |
| 8,508,376 | B2 | 8/2013 | Knox et al. |
| 8,620,031 | B2 | 12/2013 | Knox et al. |
| 8,797,531 | B2 | 8/2014 | Knox et al. |
| 8,804,119 | B2 | 8/2014 | Knox et al. |
| 2002/0153499 | A1 | 10/2002 | Oppelt et al. |
| 2004/0075056 | A1 | 4/2004 | Bell et al. |
| 2005/0069207 | A1 * | 3/2005 | Zakrzewski et al. ........ 382/190 |
| 2006/0065860 | A1 | 3/2006 | Jones |
| 2006/0202847 | A1 * | 9/2006 | Oppelt et al. ............ 340/630 |
| 2006/0232773 | A1 * | 10/2006 | Barton et al. ............ 356/338 |
| 2006/0261967 | A1 * | 11/2006 | Marman et al. ............ 340/630 |
| 2007/0064980 | A1 | 3/2007 | Knox et al. |
| 2007/0097372 | A1 | 5/2007 | Itagaki |
| 2008/0021674 | A1 | 1/2008 | Puskas |
| 2008/0069575 | A1 * | 3/2008 | Harada ............ 399/33 |
| 2008/0144169 | A1 | 6/2008 | Zahniser et al. |
| 2008/0198027 | A1 | 8/2008 | Bugge |
| 2008/0297360 | A1 | 12/2008 | Knox et al. |
| 2009/0004580 | A1 | 1/2009 | Kanaya |
| 2009/0109043 | A1 * | 4/2009 | Luterotti ............ 340/630 |
| 2011/0221889 | A1 | 9/2011 | Knox et al. |
| 2012/0140231 | A1 | 6/2012 | Knox et al. |
| 2014/0306113 | A1 | 10/2014 | Knox et al. |

FOREIGN PATENT DOCUMENTS

| | | | |
|---|---|---|---|
| JP | 55-080037 | A | 6/1980 |
| JP | 01-121737 | A | 5/1989 |
| JP | 03-239949 | A | 10/1991 |
| JP | 04-059454 | U | 5/1992 |
| JP | 06-034540 | A | 2/1994 |
| JP | 06-109631 | A | 4/1994 |
| JP | 11-295233 | A | 10/1999 |
| JP | 11-304582 | A | 11/1999 |
| JP | 2001-116692 | A | 4/2001 |
| JP | 2001-331878 | A | 11/2001 |
| JP | 2003-281643 | A | 10/2003 |
| JP | 2004-104727 | A | 4/2004 |
| JP | 2004-325211 | A | 11/2004 |
| JP | 2005-504300 | A | 2/2005 |
| JP | 2005-115970 | A | 4/2005 |
| JP | 2007-057360 | A | 3/2007 |
| JP | 2007-179266 | A | 7/2007 |
| JP | 2007-533966 | A | 11/2007 |
| JP | 2007-533971 | A | 11/2007 |
| TW | 200915010 | | 4/2009 |
| WO | WO-01/59737 | A1 | 8/2001 |
| WO | WO-2004/102498 | A1 | 11/2004 |
| WO | WO-2006/050570 | A1 | 5/2006 |
| WO | WO-2006/091328 | A2 | 8/2006 |
| WO | WO-2008/064396 | A1 | 6/2008 |
| WO | WO-2009/062256 | A9 | 5/2009 |
| WO | WO-2009/149498 | A1 | 12/2009 |
| WO | WO-2010124347 | A1 | 11/2010 |

OTHER PUBLICATIONS

"Taiwan Application No. 099114049, office action mailed 2014", 7 pgs.
"U.S. Appl. No. 12/997,155, Non Final Office Action mailed Oct. 29, 2013", 10 pgs.
"U.S. Appl. No. 12/997,155, Notice of Allowance mailed Mar. 28, 2014", 12 pgs.
"U.S. Appl. No. 12/997,155, Response filed Jan. 22, 2014 to Non Final Office Action mailed Oct. 29, 2013", 11 pgs.
"U.S. Appl. No. 13/318,309, Non Final Office Action mailed Sep. 26, 2013", 8 pgs.
"U.S. Appl. No. 13/318,309, Notice of Allowance mailed Mar. 31, 2014", 11 pgs.
"U.S. Appl. No. 13/318,309, PTO Response to Rule 312 Communication mailed Jun. 2, 2014", 2 pgs.
"U.S. Appl. No. 13/318,309, Response filed Jan. 22, 2014 to Non Final Office Action mailed Sep. 26, 2013", 15 pgs.
"U.S. Appl. No. 13/318,309, Response filed Aug. 20, 2013 to Restriction Requirement mailed Jul. 8, 2013", 10 pgs.
"U.S. Appl. No. 13/318,309, Restriction Requirement mailed Jul. 8, 2013", 6 pgs.
"European Application No. 09761163.6. Amendment filed Dec. 9, 2010", 5 pgs.
"European Application No. 09761163.6. Extended European Search Report dated Dec. 14, 2012", 7 pgs.
"European Application No. 09761163.6. Office Action mailed Aug. 21, 2012", 2 pgs.
"European Application No. 09761163.6. Response filed Oct. 31, 2013 to Office Action mailed Aug. 21, 2012", 10 pgs.
"European Application Serial No. 10769161.0, Amendment filed Dec. 1, 2011", 4 pgs.
"European Application Serial No. 10769161.0, Office Action mailed Jan. 21, 2014", 1 pg.
"European Application Serial No. 10769161.0, Response filed Jul. 30, 2014 to Office Action mailed Jan. 21, 2014", 11 pgs.
"European Application Serial No. 10769161.0, Supplementary European Search Report mailed Jan. 3, 2014", 7 pgs.
"International Application No. PCT/AU2009/000727, International Preliminary Report on Patentability dated Dec. 14, 2010", 10 pgs.
"International Application No. PCT/AU2009/000727, International Search Report and Written Opinion mailed Sep. 30, 2009", 15 pgs.
"International Application No. PCT/AU2010/000511, International Prelimiinary Report on Patentability dated Nov. 1, 2011", 16 pgs.
"International Application No. PCT/AU2010/000511, International Search Report and Written Opinion mailed Sep. 8, 2010", 23 pgs.
"Japanese Application No. 2011-512783, Office Action Summary", (English Translation), (2013), 2 pgs.
"Japanese Application No. 2012-507546, Office Action mailed Dec. 20, 2013", (English Translation), (2013), 2 pgs.
"Machine Translation of JP 06-109631, published Apr. 22, 1994", 9 pgs.
"Machine Translation of JP 11-295233A, published Oct. 29, 1999", 4 pgs.
"Machine Translation of JP 11-304582A, published Nov. 5, 1999", 5 pgs.
"Machine Translation of JP 2001-331878, pubished Nov. 30, 2001", 7 pgs.
"Machine Translation of JP 2003-281643A, published Oct. 3, 2003", 4 pgs.

(56) References Cited

OTHER PUBLICATIONS

"Machine Translation of JP 2004-104727A, published Apr. 2, 2004", 4 pgs.
"Machine Translation of JP 2004-325211A, published Nov. 18, 2004", 12 pgs.
"Machine Translation of JP 2005-115970, published Apr. 28, 2005", 18 pgs.
"Machine Translation of JP 2005-504300A, published Feb. 10, 2005", 7 pgs.
"Machine Translation of JP 2007-057360A, published Mar. 8, 2007", 4 pgs.
"Machine Translation of JP 2007-179266A, published Jul. 12, 2007", 6 pgs.
"Machine Translation of JP 2007-533966A, published Nov. 22, 2007", 4 pgs.
"Machine Translation of JP 2007-533971A, published Nov. 22, 2007", 5 pgs.
Wang, J. C., et al., "In situ particle size measurements using a two-color laser scattering technique", *Applied Optics*, 25(5), (1986), 653-657.

* cited by examiner

PARTICLE DETECTORS

PRIORITY CLAIM TO RELATED APPLICATIONS

This application is a divisional application of U.S. Ser. No. 13/318,309, filed Oct. 31, 2011, which is a U.S. national stage application filed under 35 U.S.C. §371 from International Application No. PCT/AU2010/000511, filed May 3, 2010, and published as WO 2010/124347 A1 on Nov. 4, 2010, which claims priority to Australian Application No. 2009901922, filed May 1, 2009, Australian Application No. 2009901923, filed May 1, 2009, Australian Application No. 2009901924, filed May 1, 2009, Australian Application No. 2009901925, filed May 1, 2009, Australian Application No. 2009901926, filed May 1, 2009, and Australian Application No. 2009901927, filed May 1, 2009, which applications and publication are incorporated by reference as if reproduced herein and made a part hereof in their entirety, and the benefit of priority of each of which is claimed herein.

FIELD OF THE INVENTION

The present invention relates to aspects of particle detectors. By way of example the embodiments will be described in relation to beam detectors adapted for detecting smoke. In one aspect the present invention relates more generally to battery powered devices, although the illustrative embodiment will be described in connection with beam detectors.

BACKGROUND OF THE INVENTION

Various methods of detecting particles in air are known. One method involves projecting a beam across a monitored area and measuring the attenuation of the beam. Such detectors are commonly known as 'obscuration detectors', or simply 'beam detectors'.

Some beam detectors employ a co-located transmitter and receiver with a distant reflector, and others use a separate transmitter unit and receive a unit located on opposite sides of the open space being monitored.

An exemplary, conventional beam detector is shown in FIG. 1. The detector 10 includes a light source and detector 12 and a reflector 14 placed either side of a monitored area 16. Incident light 18 from the light source and detector 12 are projected toward the reflector 14. The reflector 14 reflects the incident light 18 as reflected light 20 back toward the light source and detector 12. If particulate matter enters the monitored area 16, it will attenuate the incident light 18 and reflected light 20 and cause the amount of light received at the light source and detector 12 to diminish. An alternative beam detector separates the light source from the detector and omits the reflector and directly illuminates the detector with the light source across the monitored area 16. Other geometries are also possible.

Whilst the mechanism of smoke detection used by beam detectors is sound, beam detectors commonly suffer from a number of problems.

Firstly, beam detectors may suffer a type I (false positive) error where foreign objects or other particulate matter, such as dust, enters the monitored area and obscure the beam. Beam detectors are generally unable to distinguish between the obscuration caused by particles of interest e.g. smoke, and obscuration which results from the presence of foreign body of no interest e.g. a bug flying into the beam.

Secondly, beam detectors may require careful alignment at the time of installation. Such alignment aims to ensure that in normal conditions, free from particles, light enters the sensor so as to capture the majority of the transmitted beam, and to in turn maximise sensitivity to an obscuration. This calibration may be slow and therefore costly to perform. Moreover, it may need to be repeated as the physical environment changes, for example because of small movements in the structure to which a beam detector is attached. In some cases, if the intensity of incident light on the detector diminishes quickly this misalignment may also cause a false alarm.

The inventors have proposed a system to address some of these drawbacks in Australian provisional patent application 2008902909, filed 10 Jun. 2008 in the name of Xtralis Technologies Ltd and International Patent application PCT/AU 2009/000727. An exemplary embodiment described therein and reproduced as FIG. 2 herein includes a light source 32, a receiver 34, and a target 36, acting in co-operation to detect particles in a monitored area 38. The target 36, e.g. a corner cube reflects incident light 40, resulting in reflected light 32 being returned to receiver 34. In the preferred embodiment the receiver 34 is preferably a video camera or other receiver having an array of light sensors e.g. one or more CCD (charge-coupled device) image sensors, or CMOS (complementary metal-oxide-semiconductor) image sensors, or indeed any device capable of recording and reporting light intensity at a plurality of points across its field of view.

In this system the receiver 34 receives all of the light in its field of view 40, and includes imaging optics to form an image of a field of its view 40, including the target 36 on its image sensor. Receiver 34 records the intensity of light in its field of view, in the form of data representing the image intensity at a series of locations throughout the field of view. A portion of this data will correspond, at least partially, to reflected light 42. A microcontroller 54 analyses the image data, and determines which portion of the data provides the best estimate of reflected light 42. Because the receiver 34 has a wide field of view and has the ability to independently measure light at a wide range of points within this field of view the light source 32 need not be carefully aligned with target 36, or with receiver 34, since the effect of a misalignment will simply be that a different portion of data, corresponding to different pixels within the view, will be used to measure the reflected light 42. Accordingly, provided that the field of view of the receiver includes target 36, one or more regions of interest within the image will include a measured value for the reflected light 42.

If smoke or other particulate matter enters monitored area 38, it will obscure or scatter incident light 40 or reflected light 42. This obscuration or scattering will be detected as a drop in the intensity for received reflected light 42 measured in the image region determined by the microcontroller.

Pixels falling outside the region selected by the microcontroller, to include the reflected light 42, can be ignored as light received by these pixels does not correspond to the reflected light 42.

Over time, as the building moves or other factors alter the geometry of the system, the target 36 will still be in the field of view of the receiver 34 however, the image of the target 36 will appear at a different point on the image detector of the receiver 34. In order to address this motion, the microcontroller can be adapted to track the image of the target 36 across its light sensor over time to enable a smoke detection to be performed on the correct image regions over time.

In some embodiments described therein the target 36 is illuminated at two (or more) wavelengths $\lambda_1$ and $\lambda_2$ e.g. an infrared (IR) and ultraviolet (UV) wavelength which are emitted by corresponding light sources (or a common source) along two substantially collinear paths.

The wavelengths are chosen such that they display different behaviour in the presence of particles to be detected, e.g. smoke particles. In this way the relative change in the received light at the two (or more) wavelengths can be used to give an indication of what has caused attenuation of the beam.

Furthermore, the applicants earlier application depicts an embodiment capable of monitoring multiple targets simultaneously. According to this embodiment, illustrated in FIG. 3 herein, the detector 50 includes a light source 52, a receiver 54, a first target 56, and a second target 57 acting in co-operation to detect smoke in monitored area 58. Target 56 reflects incident light 62, resulting in reflected light 64 returning to receiver 54. Target 57 reflects incident light 65, resulting in reflected light 67 returning to receiver 54. As with the previous embodiment, the receiver 54 communicates the image data to a microcontroller 74. Microcontroller 74 analyses the data, and determines which portion of the data contains information most strongly related to reflected light 64 and reflected light 67 respectively. At the conclusion of this decision process, the microcontroller 74 will have selected two portions of data, corresponding to respective individual pixels or respective groups of pixels read from its image sensor, that can most reliably be used to measure the intensity of reflected light 64 and reflected light 67 respectively. In this way the system 50 can, by the addition of only an additional target or light source, perform the function of two beam detectors.

Using such a system, present inventors have previously proposed a particle detection system which addresses the seemingly contradictory requirements of the need for high sensitivity and the need for a wide angular range of operation in a beam detection system. However, these constraints as well as constraints on the intensity of light sources able to be used as transmitters mean that there may be a need to further enhance the particle detection system in these respects.

In beam detectors the transmitted light intensity may be limited. For example, there may be budgetary considerations which mean that a relatively low power light emitter must be selected in the product. Furthermore, in some cases, a limited electrical power supply is available, especially if the transmitter unit is powered by a battery. Eye safety is also a factor in limiting the transmission power of the light source as is the potential nuisance effect of visible light from the transmitter. For any of these reasons, a relatively low transmitted signal power may be used in a beam detector. Consequently, the signal to noise ratio of the system may be compromised.

In order to operate satisfactorily whilst keeping the emitted power as low as possible it is advantageous, for sensitivity purposes, that the polar emission pattern of the transmitter and the viewing angle of the receiver are kept as narrow as possible. However, for installation and alignment purposes it is advantageous that the same angles are kept as broad as possible. Accordingly, accommodating these seemingly contradictory requirements of the system can present problems.

A further problem that may arise in such a system is that a reflective surface may provide one or more unintended light paths between the transmitter and the receiver, and so interfere with either the recognition of the direct light path, or cause uncontrolled and unintended contributions to the received signal(s), or both. This effect is exacerbated if the reflective surface is subject to any changes, such as movement with temperature or building wind loads; or the movement of people or vehicles that causes its reflected contribution to vary over time.

Since beam detector components are often mounted just below a substantially flat ceiling, this type of undesired reflection may be common. It has been realised by the inventors that to cause such an issue, the finish of the reflective surface does not need to be obviously reflective or mirror-like, and that even a common matt-painted surface may provide a relatively strong specular reflection at the narrow angle of incidence, such as would typically occur in a beam detector with a long span mounted near a surface. While a mirror like, or gloss finish is the extreme case, even an apparently rough surface may give enough specular reflection to create these problems.

Adjacent walls, particularly glazed walls, may also create a similar issue with the additional complication that blinds or open-able windows may be used at various times. However, this issue does not arise as commonly, since it is rarely required that beams are directed in close proximity to walls.

For this reason and others, beam detectors typically require careful alignment at the time of installation. Such alignment aims to ensure that in normal conditions, free from particles, light enters the sensor so as to capture the majority of the transmitted beam, and to in turn maximise sensitivity to an obscuration. This calibration may be slow and therefore costly to perform. Moreover, it may need to be repeated as the physical environment changes, for example because of small movements in the structure to which a beam detector is attached. In some cases, if the intensity of incident light on the detector diminishes quickly this misalignment may also cause a false alarm.

Since beam detectors are typically mounted to a wall or like flat surface it is generally not possible to get behind the detector in order to use a line of sight type alignment device. Also, since detectors are usually mounted at high elevations and in inaccessible locations, the problem of achieving accurate alignment, and the difficulties caused by misalignment, are exacerbated.

As discussed in relation to FIG. 1, some beam detectors employ a co-located transmitter and receiver with a remote reflector. Another arrangement, as illustrated in FIG. 9, uses a light source 1102 that is remote from the receiver 1104. The separate transmitter 1102 may be battery powered in order to avoid the requirement for costly wiring. Furthermore, in embodiments that are powered from the fire alarm loop the detector unit 1104 (or the combined light source and detector 102, of FIG. 1) may also employ a battery to act as a reserve supply for periods of high power consumption that exceed a specified limit of capacity of a wired loop supply.

In order to achieve the required service life, and for conformance with safety requirements, it is desirable that the battery-powered units should not be powered on during shipping or in long-term storage.

Conventionally, battery-powered equipment is often activated using a manual switch, or by removal of an insulating separator, or by inserting the batteries into the equipment. The inventors have identified that these methods have several disadvantages, particularly in the case of beam-detection systems. The conventional systems for powering up the battery-powered equipment are not automatic and, in consequence, may be overlooked when the beam-detection system is installed. In beam-detection systems the wavelengths used for the light source 102, 202 are often invisible to the human eye. This makes it difficult to confirm that the light source 102, 202 is active when installed. In addition, the beam detection systems are often installed at a significant height, requiring scaffolding or a cherry-picker to access the system components. As a result, it is time-consuming and costly to access and rectify a unit that has inadvertently been left non-operational.

Some of the conventional techniques of activating battery-powered units also interfere with the common requirement that beam-detection systems should avoid arrangements that cause penetrations through the main enclosure of the unit. It is often the case that transmitters are designed to be resistant to the entry of dust and moisture, and the use of manually-operated switches may makes this isolation more difficult and costly to achieve.

A further problem that may arise with beam detectors is that their exposed optical surfaces may become contaminated with dirt over time. This can gradually reduce the received signal with the potential to be raise a false alarm. Methods to avoid and remove dirt build up on optical surfaces are known, and employed particularly commonly in the field of closed circuit TV security surveillance applications, such as the use of contamination-resistant coatings on viewing windows, protective shrouds, wash-wipe mechanisms and the like.

Also, as described in PCT/AU2008/001697 in the name of Xtralis Technologies Limited, there are other mechanical means for cleaning or avoiding dirt build up on optical surfaces, including methods using filtered clean air as a barrier, or electrostatic guard areas to prevent window contamination. Such methods may advantageously be used for beam detectors separately or in combination with other aspects of the current invention, and each constitute an aspect of the present invention.

With the dual wavelength system described in connection with FIGS. 2 and 3 a variation in the absolute intensities of received light is tolerated to an extent, because a differential measure is used to detect particles in the beam, but relative variation between the wavelengths may create faults or, worse still, false alarms; specifically a relative reduction in the received signal from the UV beam compared to the IR beam may be mistaken for smoke. Thus any wavelength selective build up of contaminants on the optical surfaces can be problematic.

It is a problem in the field of video surveillance, and similar fields which have remotely located optical devices (such as cameras), that insects or other foreign bodies may from time to time land on the exposed surfaces of the optical components of the system and partly or totally obscure the field of view of the optical components. Similar problems may also arise in particle detection systems like beam detectors which are exposed to bugs and other foreign bodies. Accordingly, there is a need to protect components of particle detection systems such as a beam detector and thereby to avoid or minimise false alarms caused by such circumstances.

As described above, some embodiments of the present invention may include separate light emitters in the transmitter which are configured to emit light in different wavelength bands. Most preferably the light emitters are LEDs. Over time the output of the LEDs may vary in either absolute or comparative intensity or both. With the dual wavelength system variations in absolute intensity can be tolerated to a certain extent so long as the relative measure of intensity used by the system for detecting particles remains substantially constant. However, relative variations in the output intensities of the two light emitters may create faults or false alarms. This is particularly the case when the output signal from the UV LED reduces compared to the output of the infrared LED.

It is known to use beam detectors to monitor large areas by using beams over say, 150 meters long or, in relatively confined spaces requiring a beam length of eg. only 3 meters. In conventional beam detector systems an identical light source and receiver can be used for these two very different applications, i.e. 150 meter separation or for 3 meter separation. This is made possible by either adjusting the gain on the receiver or turning down the transmitter power according to the separation between the transmitter and the receiver.

However, the applicant's previous applications discussed above, and the example of FIG. 3 show a beam detector which may include more than one transmitter for each receiver. This presents its own particular problems, in that it is possible to have multiple transmitters set at vastly different distances from the receiver. For example, consider a room of the type illustrated in FIG. 57. This room 5700 is generally L-shaped and has a receiver 5702 mounted at the external apex of the L-shape. Three transmitters 5704, 5706, 5708 are positioned around the room 5700. The first transmitter 5704 is located along one arm of the L. A second transmitter 5706 is located in a position 90° from the first receiver 5704 at the end of the other arm of the L. A third transmitter 5708 is mounted across the apex of the L-shape from the receiver 5702. As will be appreciated the distances between the transmitters 5704 5706 and the receiver 5702 are much longer than the distance between the transmitter 5708 and the receiver 5702. As a result, the level of light received from each transmitter will be very different. Moreover transmitter 5708 may be so close to the receiver that it saturates its light receiving element.

Other disadvantages may also arise, for example, from time to time, an installer may take advantage of the reliable performance of beam detectors and install a system outside the manufacturer's specifications. For example, although beam detectors are often intended to operate with a substantial separation between the transmitter and receiver an installer may extend this distance to provide a system beyond that recommended by the manufacturer or allowed by regulations. In some cases an installer of the particle detector may not know of the limits of operation of the receiver for the light source provided therewith.

In such circumstances an installed particle detector may operate satisfactorily at initial installation, but sometime following installation, cease to operate correctly. This may occur, for instance where the particle detector or was initially installed close to, but beyond its design limits. Over time, changes may occur to the equipment or environment, which gradually alter the received signal strength due to reasons other than the presence of particles in the beam. These changes may be caused by, for example, component ageing, gross alignment drift, or contamination of optical surfaces. Such system drift would ordinarily be handled by the system if it had been set-up within its design limits. However, when the system is set up outside these limits, degradation of performance and the associated occurrence of fault conditions may occur prematurely or repeatedly.

Furthermore, it is desirable to be able to calibrate and/or test such a beam detector by simulating the presence of smoke using a solid object. Such a test is a requirement of standards bodies testing for beam detectors. For example, the European EN 54-12 standard for 'Biodetection and fire alarm systems. Smoke detectors. Line detectors using an optical light beam'.

In prior art testing methods the testing of beam detectors employs a light filter that partially obscures the projected light beam to simulate the effect of smoke. The filters used usually consist of a mesh of fibres, or dye-loaded plates or transparencies with printed features which obstruct all visible and near visible wavelengths by substantially the same amount in a repeatable fashion. The present inventors have realised that this type of filter may not be suitable for use with a beam detector of the type described above.

In a preferred embodiment of the system described in FIGS. 1 to 3, the light sources are configured to include a plurality of light emitters, wherein each light emitter is adapted to generate light in a particular wavelength band. Moreover, the separate light sources are arranged to emit light at different times in order that a monochromatic imaging element may be used. The direct result of the use of separate light emitters is that there is some separation between the two light emitters in the light source, and thus the light will travel over slightly different, although closely adjacent, beam paths through the intervening space between the light source and receiver. This provides a risk that a small object such as an insect on the transmitter could affect one light path more than the other and so affect the reading of the receiver. This may induce a false alarm or unnecessary fault condition.

Conventional beam detectors require careful alignment at the time of installation. Such alignment aims to ensure that in normal conditions, free from particles, light enters the sensor so as to capture the majority of the transmitted beam, and to in turn maximise sensitivity to an obscuration. This calibration may be slow and therefore costly to perform. Moreover, it may need to be repeated as the physical environment changes, for example because of small movements in the structure to which a beam detector is attached. As stated above, the inventors have previously proposed a particle detector in PCT/AU 2008/001697, filed 10 Jun. 2009 in the name of Xtralis Technologies Ltd (the specification of which is incorporated herein, by reference, in its entirety) which includes a receiver which has a light sensor comprising matrix of light sensor elements, e.g. CCD (charge-coupled device) image sensor chip, or CMOS (complementary metal-oxide-semiconductor) image sensors such as in a video camera, or other receiver that is capable of receiving and reporting light intensity at a plurality of points across its field of view. Each sensor element in the receiver produces a signal that is related to the intensity of the light that it receives. The signals are transmitted to the controller, where a particle detection algorithm is applied to the received image data. Compared to a single-sensor receiver, the receiver in this particle detector has a wider field of view but lower noise and has the ability to independently measure light at a wider range of points within this field of view.

Because each sensor element has an inherent noise level, the overall signal-to-noise ratio of the system can be improved by focusing the target (i.e. beam image) on a single sensor element. However, this may not yield optimal results.

The above mentioned type of sensor e.g. CCD's and the like, are sometimes subject to a phenomenon created by the image processing algorithm used for the receiver, known as staircasing, wherein adjacent pixels or adjacent groups of pixels have significantly different values. The physical structure of the sensor also has non-responsive "gaps" between sensor elements that produce no signal. Because of these effects, any variation in the alignment of the smoke detector components can potentially create a large variation in the measured light intensity level.

For example, because of the small size of the focused target, a very small movement of the receiver or the transmitter could cause the target to move onto an entirely different sensor element with a very different inherent noise level or response compared to the previous pixel on which it was focused. It may also fall into a position, where all, or a non-trivial part, of the received beam falls into one of the aforementioned "gaps". The resulting variation in the image intensity as determined by the controller can thus potentially cause the controller to falsely detect smoke.

To partly ameliorate this problem, the detector can be adapted to track the target across the light sensors over time to enable a smoke detection to be performed on the signals from the correct sensors over time. However, to properly determine the image intensity, the controller will be required to ascertain the inherent properties of different light sensors used over time. Doing so requires system resources such as processing cycles and power. Also it is not always possible for the controller to make this determination.

In beam detectors an additional problem that may arise is interference from ambient light within the volume being monitored. The ambient light can either be from sunlight illuminating the volume or artificial lighting used to illuminate the space. Accordingly, beam detectors require mechanisms for minimising the impact of this light. This problem is compounded by the conflicting requirement that the light sources of the beam detector should be relatively low powered so that they minimise power consumption, are eye safe and do not create a visible nuisance. In prior art beam detectors which use a single wavelength of light a filter is typically used to reduce the signal from ambient light. In the case of an infrared beam detector this is generally a low pass filter that removes substantially all visible and UV light. However, this is inappropriate for a multiple wavelength system as described herein.

In the preferred embodiment of the system described above the particle detector is powered at the receiver directly from the fire alarm loop. This minimises the installation costs of the device in that it obviates the need for dedicated wiring for supplying power or communicating with the detector. However, the fire alarm loop usually only provides a very small amount of DC electrical power for the detector. For example, an average power consumption of about 50 mW may be desirable for such a detector. However with current technology the power consumed during video capture and processing may be far above the 50 mW that is available from the loop. To address this problem a separate power supply could be used, but this is costly since standards for fire safety equipment are onerous, e.g. they require a fully approved and supervised battery backed supply, and fixed mains wiring.

The limited supply of power also limits the optical power output of the transmitter. The limited optical power output in turn limits the signal to noise ratio of the measured signal. If the signal to noise ratio of the system degrades too far, the system may experience frequent or continual false alarms.

In some systems, the signal to noise ratio can be enhanced by employing long integration or averaging times at the receiver. However system response times, which are usually between 10 and 60 seconds, must be increased to higher levels if long integration times are used. This is undesirable.

In addition to using a beam detector for smoke detection it is often desirable to use other sensor mechanisms for detecting additional or alternative environmental conditions or hazards, for example $CO_2$ gas detection or temperature detection. The detectors conventionally use a wired or radio communication link to signal an alarm or fault condition to fire alarm control panel or like monitoring system. As such these links often add significant cost and potential reliability issues to the alarm system.

In some systems the present inventors have determined that it can be beneficial to operate at least some components, and most advantageously the transmitter on a battery. An exemplary component is described in the applicant's co-pending patent application no. PCT/AU 2009/000727, filed on 26 Jun. 2008, the contents of which are incorporate herein by reference for all purposes.

However, a problem that can arise in a battery powered component of a particle detector is that over time, the batteries of the component will become discharged and the component will ultimately fail. Such failure will potentially require an unscheduled maintenance call out for the device to be repaired and recommissioned. In a smoke detection application this is particularly problematic as the equipment is used in a life-safety role and faults are required to be rapidly remedied. The problem can be remedied by performing preventative maintenance but ultimately this may amount to performing unnecessary servicing and replacement of units that have a significant amount of battery life remaining and therefore is costly and wasteful of materials.

Unfortunately, variations in individual battery performance and environmental conditions make simply scheduling routine replacement periods unreliable and potentially wasteful. One apparent solution to the problem is to equip the component with an indicator of battery state, however this has a disadvantage of adding cost, and the indicator itself is power consuming which further reduces battery life. Moreover, it requires regular direct inspection of the indicator on the component which, in the case of a beam detector, may be particularly inconvenient.

In beam detectors such as that described in relation to FIG. 3 i.e. where a plurality of beam detectors are formed by corresponding transmitter and receiver pairs, such that two or more beams either intersect or pass through a common region of air, sufficiently close to each other that their points of intersection can be mapped to addresses within the region being monitored, a problem may arise in that any one of the subsystems may be affected by environmental conditions or system problems that do not affect the other subsystem. Such issues generally force a reduction in achievable sensitivity or increase the rate of unwanted false alarms.

Reference to any prior art in the specification is not, and should not be taken as, an acknowledgment or any form of suggestion that this prior art forms part of the common general knowledge in Australia or any other jurisdiction or that this prior art could reasonably be expected to be ascertained, understood and regarded as relevant by a person skilled in the art.

SUMMARY OF THE INVENTION

In a first aspect, the present invention provides a beam detector arrangement comprising a transmitter adapted to transmit one or more beams of light having a predetermined characteristic over a field of illumination and a receiver having a field of view of the receiver and adapted to receive a beam of light transmitted by the transmitter;
the beam detector being installed to protect a monitored volume which includes a structure having one or more reflective surfaces within the field of illumination of the transmitter and the field of view of the receiver;
the beam detector including a processor adapted to determine whether a light beam received at the receiver possesses one or more predetermined light characteristics.

In the event that the one or more characteristics are possessed the processor can be adapted to determine that a beam of light from the transmitter is received. In the event that a received beam does not possess the one or more characteristics the processor can determine that a beam of light from the transmitter is not received. Alternatively the processor can determine that the beam of light received is a reflection of the transmitted beam.

The beam detector arrangement can include signalling means adapted to signal a fault condition in the event that the processor determines that a beam of light from the transmitter is not received and/or a reflected beam is received.

In a second aspect the present invention provides a method for determining whether a beam of light received by a receiver of a beam detector is a directly transmitted beam or a reflected beam. The method including receiving the beam at a receiver and measuring one or more predetermined characteristics of the beam, and depending on the extent to which the predetermined characteristic is present in the beam determining if the received beam is a directly transmitted beam or a reflected beam. In the event that the one or more characteristics of the received beam do not substantially match one or more predetermined characteristics of the transmitted beam the method can include, determining that the received beam is a reflection. The beam characteristics can include relative strength of two or more wavelength components in the received beam and/or received polarisation characteristics of the beam.

In a further aspect the present invention provides a receiver for a beam detector, the receiver including the plurality of image sensors, each image sensor including a plurality of sensor elements, said image sensors being arranged to have at least partially overlapping fields of view. The receiver can additionally include an optical arrangement adapted to form an image on each of the two sensors. The receiver can additionally include image analysis means to analyse an image from more than one of the plurality of image sensors to determine an angular position of an image component within the field of view of a plurality of the sensors. The image component can be one or more beams transmitted by a light source of a beam detector.

In a further aspect the present invention provides a receiver for a beam detector, the receiver including:
one or more sensors including a plurality of sensor elements to receive a beam of light from a transmitter;
processing means in data communication with the one or more sensors to receive and process image data therefrom; and
input means adapted to receive an input representative of a number of beams which are to be received from one or more transmitters of the beam detector.

Preferably, the input means can include one or more switches (e.g. DIP switches), or by providing a data input interface such as a serial port, or the like, over which data may be provided to the processor means, or memory associated therewith.

In a further aspect, the present invention provides a beam detector including: one or more light sources adapted to transmit said beam of light across a region being monitored; one or more receivers arranged with respect to the transmitter and the volume being monitored such that light from the transmitter arrives at the receiver after traversing at least a part of the volume being monitored.

In certain embodiments of the present invention the beam detector system may include one or more light blocking baffles arranged with respect to the volume being monitored and the transmitter and/or receiver such that no reflections from a surface within a field of illumination a light source and a field of view of a light receiver of the beam detector arrive at the receiver.

In preferred embodiments of the beam detector the light receiver is made in accordance with one of the aspects of the invention described herein.

In certain embodiments of the present invention, the transmitter of the beam detector is made in accordance with an embodiment of any one of the aspects of the present invention.

In one aspect the present invention provides a transmitter for a beam detector transmitter including one or more light sources adapted to generate light in a spatially distinct beam pattern. Preferably, the spatially distinguishable beam pattern is not symmetrical in at least one plane. The spatially distinguishable beam pattern can include a pattern of individual light beams having distinguishable characteristics. The characteristics may be wavelength characteristics, polarisation characteristics or modulation characteristics which are distinguishable from each other. Other characteristics may also be used. For example, in a preferred form, this distinguishable pattern can include a pair of distinguishable light beams. A single light source can be used in some embodiments of the transmitter. In this case, the image of the beam which is formed by a receiver must be such that a shape of the light source is directionally distinguishable. For example, the image of the light source can be 'L' shaped such that up and down and left and right can be distinguished from an image of the light source.

In a beam detector including a transmitter of the above type, the present invention, in a further aspect, also provides a method of determining whether a beam received at a receiver is transmitted by a direct or reflected path, the method including:
arranging a light source and receiver such that the beam transmitted by the source is received at the receiver; and
orienting the light source with respect to an adjacent surface within the field of illumination of the light source and field of view of the receiver, such that a direct image of the light source and reflected mirror image of the light source from the surface are distinguishable at the receiver.

This step of aligning can include aligning the light source such that its image is not symmetrical in the direct and reflected images.

In a further aspect the present invention provides a method of distinguishing a directly received beam from a reflected beam in a beam detector system, the method including receiving an image containing two image segments which potentially correspond to beams transmitted by the particle detector;
determining a brightness of each of the received beams; and
determining that a brightest one of the received beams is the directly received beam.

In a further aspect of the present invention there is provided a method of determining which one of a plurality of received beams is directly received from a light source and which is received by a reflection from a surface, the method including:
determining which of the received beams is received at a sensor element of a light sensor of a receiver of the beam detector that is furthest perpendicularly from the reflecting surface; and
designating the determined beam image as the direct beam image.

In a first aspect there is provided a beam detector including:
a light source adapted to transmit a beam of light with a first polarisation state;
a light receiver adapted to receive light in a second polarisation state and output a received light level; and
a controller adapted to analyse the received light level and apply alarm and/or fault logic and if a predetermined fault condition exists, to initiate an action.

In one embodiment the first and second polarisation states are parallel.

In another embodiment the first and second polarisation states are offset from each other. They may be orthogonal.

The beam detector can include a light source adapted to transmit a second beam of light with a third polarisation state. The first and third polarisation states are preferably different. Most preferably they are orthogonal. The first and second light sources can be a common light source. The third and second polarisation states can be the same.

The beam detector can also include a light receiver adapted to receive light in a fourth polarisation state.

The second and fourth polarisation states are preferably different. Most preferably they are orthogonal. The fourth and first polarisation states can be the same.

One or both of the light receiver or transmitter can include a polarising filter, or a plurality of interchangeable filters.

A component of a beam detector system including:
at least one electro-optical component configured to emit light or receive light in a first spatial distribution; and
an optical subsystem arranged with respect to the electro-optical component such that the first spatial distribution is adjusted to form a second spatial distribution, wherein the relative extent of the first spatial distribution along two non-parallel axes are different to the relative extent of the second spatial distribution along the same axes.

Preferably the axes are orthogonal to each other. Most preferably one is interdict to be a vertical axis and the other a horizontal axis.

Preferably the second spatial distribution is relatively wider horizontally than vertically when compared to the first spatial distribution.

The optical subsystem can include an anamorphic lens, or other 'wide-screen' optical system.

The electro-optical component can be an image sensor. The electro-optical component can be a light emitter e.g. an LED, laser diode.

A further aspect of the present invention provides a light source for a beam detector including:
at least a light emitter to generate a beam of light; and
an optical subsystem for controlling the angular dispersion of the beam of light wherein the optical subsystem is adapted to shape the beam of light such that it has a larger angular dispersion along one axis than another.

Preferably the shape of the beam is wider than it is high. The beam can be shaped such that it has a horizontal angular dispersion of between 5 and 25 degrees. Most preferably it is between about 10 and 15 degrees.

The vertical dispersion can be between 0 and 10 degrees. Most preferably it is between about 3 and 5 degrees.

In a yet another aspect the present invention provides a receiver for a beam detector including:
a light sensor capable of providing an output representative of a sensed light level at a plurality of positions on the sensor; and
an optical subsystem adapted to receive light in a field of view having a first shape and direct it onto the light sensor in an image of a second different shape.

Preferably the optical subsystem includes an anamorphic lens. The field of view of the optical subsystem is preferably wider in one direction than another. Preferably it is wider than it is high.

The field of view of the optical subsystem can be defined by a maximum light acceptance angle in one direction and a maximum light acceptance angle in another direction.

Preferably the maximum horizontal acceptance angle is 90 degrees or less. However it could be more in some cases.

Preferably the maximum vertical acceptance angle is 10 degrees or less.

A further aspect of the invention, in broad outline relates to the set up of particle detection apparatus wherein a visual alignment device incorporated with or attached to the particle detection apparatus is directed towards a target and is used to accurately align the apparatus at the time of installation, or when adjustment of alignment is necessary. The visual alignment device and the optical elements in the particle detector will have a fixed alignment relative to each other. The visual alignment device may comprise a visual beam generator which projects a visually observable light beam towards the remote surface, or it may comprise a video camera which receives an image of the remote surface and displays the image of the surface on a display screen.

One aspect of the invention provides a component of a smoke detector comprising:
- an optical module including one or more light sources and/or one or more light receivers;
- mounting means for mounting the optical module to a support surface;
- an articulated connection located between the mounting means and the optical module; and
- a visual alignment device fixed to move with the optical module for assisting in aligning the light source or sources and/or receiver or receivers, relative to a target.

Optionally the visual alignment device comprises one or more sockets in the optical module in which an alignment beam generator can be inserted.

The articulated connection may include one or more locking means for locking the orientation of the optical module relative to the mounting means. The articulated connection may comprise a ball and cup joint, capable of allowing the optical module to be tilted relative to the mounting means through a relatively large arc of tilt, the locking means adapted to lock the ball to the cup in a selected orientation. The locking means may comprise a screw member which engages in a threaded bore in the cup and contacts the surface of the ball to lock the ball and cup together. Optionally the screw is accessible via the visual alignment device.

In an alternative configuration of the invention provides a component of a smoke detector comprising:
- an optical module including one or more light sources and/or one or more light receivers;
- fixed mounting means for mounting the optical module to a support surface;
- an articulated mounting means located between the optical module and one or more light sources or light receivers; and
- a visual alignment device fixed to move with the light source or sources and/or receiver or receivers, to assist in aligning the light source, sources and/or receivers relative to a target.

Optionally the visual alignment device comprises one or more sockets in the articulated mounting means in which an alignment beam generator can be inserted.

The articulated connection may include one or more locking means for locking the orientation of the optical module relative to the articulated mounting means. The articulated connection may comprise a ball and cup joint, capable of allowing the optical module to be tilted relative to the mounting means through a relatively large arc of tilt, the locking means adapted to lock the ball to the cup in a selected orientation. The locking means may comprise a screw member which engages in a threaded bore in the cup and contacts the surface of the ball to lock the ball and cup together. Optionally the screw is accessible via the visual alignment device. Alternatively a rotatable mount can be used.

The visual alignment device may comprise a laser housed in or mounted on a cylindrical tube or shaft sized to be a sliding fit in the beam alignment means. Optionally the laser forms part of a tool for locking the articulated connection. The laser may flash to assist in visual identification.

Alternatively the visual alignment device may comprise a video camera mounted to move with the housing, and able to generate an image of the target, the image including sighting means which, when aligned with the target will indicate that the optical component is operationally aligned. The housing may include a video camera mount which, when the camera is mounted thereto aligns the camera with the housing such that the camera has a field of view aligned in a direction in a known orientation relative to the light source. Optionally the known orientation is axially aligned with light emitting from the light source.

The component can be, for example a transmitter, receiver or target for a particle detector, such as a beam detector.

Another aspect of the invention provides a method of aligning a component of a smoke detector comprising:
- mounting the component in an initial orientation to a support surface, the component including a visual alignment device;
- determining the orientation of the component by visually observing an output of the visual alignment device;
- adjusting the orientation of the component by monitoring the visual alignment device until the component is in a selected operating orientation; and
- fixing the component in said operating orientation.

The method can include removing the visual alignment device from the component.

The orientation of the component could be determined by observing either of a position of an alignment light beam emitted from the visual alignment device at a location remote from the support surface, or observing an image of the remote surface generated by a camera of the visual alignment device.

A further aspect of the invention provides an alignment tool comprising:
- a shaft having a handle;
- a driver actuatable by the handle;
- a visual alignment device in a fixed or known orientation relative to the driver; and
- a shaft and a handle.

Further there is provided for the visual alignment device to comprise a laser which is located in a casing, and for a handle to have a recess therein shaped to receive the casing. The laser will typically be a battery powered laser with an on/off switch so that the laser may be switched off when not in use. The shaft may be straight or may have an elbow therein, depending on the configuration of the apparatus with which the tool is to be used. Alternatively the visual alignment device may comprise a video camera.

An aspect of the invention provides a visual alignment tool having:
- engagement means for engaging with and aligning the visual alignment tool relative to a particle detector component; and
- visual targeting means for providing a visual indication of the alignment of the particle detector component when so engaged.

The visual targeting means may be a camera, but is preferably a means for projecting visible light. The visible light could be a simple beam as in a laser pointer, or more complex patterns such as cross hairs. The means for projecting may flash to assist in visual identification. The visual targeting means is preferably battery powered, and may include an on/off switch so that it may be switched off when not in use.

The engagement means is preferably an elongate projection receivable within a recess within the particle detector component. Preferably the visual targeting means is coaxially aligned with the engagement means.

The visual alignment tool preferably includes an elongate handle and a shaft, the shaft projecting from an end of the handle and being coaxially aligned therewith, wherein at least a portion of the shaft forms the engagement means. The shaft and recess may be cylindrical and sized for a sliding fit therebetween.

The visual targeting means is preferably arranged at the other end of the handle. Optionally the visual targeting means may be removable from the handle.

The visual alignment tool may include a driver for engaging with and actuating a locking means of the particle detector component.

The driver is preferably formed at an end of the shaft distal from the handle and rotatable about the axis of the shaft to actuate the locking means. The driver may be, for example, an Allen key (hex), Phillips head or other propriety shape e.g. a triangle. Ideally the driver is shaped for engagement with the locking means in only a single relative rotational orientation, e.g. the drive may be a non-equilateral triangular projection receivable in a complementary recess, so that the rotational orientation of the visual alignment tool is indicative of the state of the locking means. Visible indicia may be provided on the tool to aid in said indication.

In this aspect the invention also provides a particle detector component;
  the component including a mounting portion, an optical module, and locking means;
  the mounting portion being fixedly attachable to a mounting surface;
  the optical module being articulated relative to the mounting portion for alignment relative to a target and including means for enabling a visual indication of said alignment; and
  the locking means being actuatable to lock the optical module relative to the mounting portion in a selected alignment.

The term 'target' as used herein is intended to be interpreted broadly, and may include an actual target mounted at the remote location for reflecting the source light back to a receiver. The target may also however simply refer to a remote surface if reflected light from that remote surface is monitored by the receiver or even a desired point on which a component should be aligned, e.g. the receiver could be a target for a light source or vice versa.

The means for enabling a visual indication could be a visual targeting means, including an electro optical device such as a camera or laser pointer, but is preferably an engagement feature for cooperating with a visual alignment tool incorporating visual targeting means.

Preferably the optical module includes an elongate recess forming the engagement feature. The recess preferably has at least one open end and is arranged so that the axis of the recess projects toward the target when the optical module is in alignment with it. The recess may project in a direction parallel to a limit of a field of operation of the optical module or in some other known physical relationship with the spatial optical characteristics of the optical module.

The locking means is preferably actuatable by the visual alignment tool. The locking means preferably includes a driven member located within the recess and engageable with a driver of the visual alignment tool to actuate the locking mechanism. Preferably it is adapted to be rotationally driven about the axis of the recess to a selected orientation to actuate with locking means. The driven member is preferably shaped for engagement with the driver of the visual alignment tool in only a single relative rotational orientation, e.g. the driver may a non-equilateral triangular projection receivable in a complementary recess formed in the driven member, so that the rotational orientation of the visual alignment tool is indicative of the state of the locking means. Indicia may be provided on the component to aid in said indication.

Preferably one of the optical module and the mounting portion, most preferably the optical module, is captured within the other portion, said articulation being effected by a spherical sliding fit between the optical module and the mounting portion. The driven member may be a grub screw within one of the optical module and mounting portion, and rotatable to engage the other of the optical module or mounting portion. But preferably, the optical module includes a brake shoe and a cam, wherein the cam is arranged to be driven by the driven member and in turn drive the brake shoe to, frictionally or otherwise, engage the mounting portion and thereby lock the optical module relative to the mounting portion. The cam may be attached to the driven member or integrally formed therewith. The braking shoe may be biased towards a retracted, non-braking, position.

The optical module may include a simple optical element, such as a lens or a mirror. For example, a mirror alignable for redirecting a beam to or from a fixedly mounting electro-optical element. In this case the mirror and electro-optical element may be mounted in a housing.

Preferably the optical module includes an electro-optical element such as a light emitting element or elements or light receiver. The electro-optical element could be camera.

Preferably the particle detector component is configured to operatively connect a circuit, to enable operation of the electro-optical element, to a power supply when said locking means is actuated. For this purpose, a switch may be associated with the driven member. For example, the driven member may carry at a point at a radius from its axis a magnet which is arranged to act on a reed switch when the driven member is rotated to the selected orientation.

This aspect of the invention also provides a combination of the particle detector component and the visual alignment tool, and methods of installing, and aligning, a particle detector component.

There is provided a method of aligning a particle detector component, the particle detector component includes an optical module, a mounting portion and locking means, the method includes:
  articulating the optical module relative to the mounting portion to align a visual indication of orientation with a target.

Preferably the method includes actuating the locking means to lock the optical module in said alignment.

Preferably the method further includes engaging with the optical module of the particle detector component a visual alignment tool to provide said visual indication of the orientation of the optical module; and,
  disengaging said visual alignment tool.

Said actuation preferably includes rotating said visual indication tool, and most preferably simultaneously connects an electro-optical component to a power supply.

The method of installing the particle detector component includes:
  fixedly mounting a mounting portion of the particle detector component to a mounting surface; and
  aligning the particle detector component in accordance with the aforedescribed method.

In a preferred form the step locking the optical module and connecting the electro-optical component to a power supply.

In another aspect the invention provides a smoke detector component:
  the component including a mounting portion, an optical module, locking means and activation means;
  the mounting portion being fixedly attachable to a mounting surface;
  the optical module including a electro-optical element and being articulated relative to the mounting portion for alignment relative to a target;

the locking means being actuatable in response to an installer input to lock the optical module relative to the mounting portion in a selected alignment; and the activation means configured to operatively connect the electro-optical element to a power supply in response to said installer input.

In a further aspect the present invention provides, a component of a particle detector including an electro-optical component adapted to at least transmit or receive an optical signal over an angular region, an optical assembly adapted to redirect an optical signal said optical assembly an electro-optical component being mounted relative to each other such that the electro-optical component receives or transmits optical signals via the optical assembly, wherein: the orientation of the optical assembly is adjustable with respect to the electro-optical component to enable the direction of optical signals transmitted or received by the component to be changed.

Preferably the component includes a housing in which the electro-optical component and optical assembly are mounted; and an aperture through which an optical signal may pass.

The mounting means can be adapted to mount the optical assembly rotably with respect to the housing. The mounting means is preferably a friction fit with a recess in the housing. The mounting means preferably includes an engagement means engagable by a actuating tool to allow rotation of the optical assembly. The engagement means can be adapted to engage with an actuating tool as described herein.

The optical assembly can include a mirror to reflect an optical signal.

The electro-optical component can be a light sensor including a plurality of sensor elements. The light sensor is preferably a camera adapted to capture a series of images.

According to an aspect of the invention there is provided a particle detector assembly comprising a first module having an actuator and a second module configured to be mounted to the first module. The second module comprises electro-optical system for use in a beam-detection system and a power source operable to provide electrical power to the electro-optical system. The second unit also includes a switch responsive to the actuator. When the second module is mounted to the first module, the actuator causes the switch to operatively connect the power source to the electro-optical system.

In one arrangement the actuator is a magnet, and a reed switch is used to detect the proximity of the magnet when the two modules are assembled.

In broad concept, one aspect of this invention, may improve system performance in cases where contamination of the optical surface affects both wavelengths by substantially the same amount. In this aspect, very gradual reduction of the received signals are compensated by an increase of the effective overall receiver gain of both signal channels, using a time constant that is chosen to be far longer than might cause a real fire to go undetected; for example a week.

Thus, in one aspect the present invention includes detecting a long time drift in received light level in a particle detection system; and increasing gain of a detection circuit to compensate for the drift. In a system with multiple illuminations, e.g. at different wavelengths a wavelength dependent gain increase can be made.

This concept can be extended such that where the contamination of the optical surface affects the shorter wavelength by more than it does the longer wavelength, as may occur when the contamination consists largely of very small particles such as are present as a result of smoke pollution, the very gradual reduction of the received signals are individually compensated by an increase of the effective overall receiver gain of each signal channel separately, again using a time constant that is chosen to be far longer than might cause a real fire to go undetected; for example a week.

In a first aspect the present invention provides a light source for use in a particle detection system, the light source adapted to transmit: a first light beam in a first wavelength band; a second light beam in a second wavelength band; and a third light beam in a third wavelength band, wherein the first and second wavelengths bands are substantially equal and are different to the third wavelength band.

The first and second wavelength bands may be in the ultraviolet portion of the EM spectrum. The third wavelength may be in the infrared portion of the EM spectrum.

The location from which the first light beam is transmitted from the light source may be separated from the location from which the second light beam is transmitted from the light source. The separation may be approximately 50 mm.

The light source may further include a first light emitter for emitting the first and second light beams and a second light emitter for emitting the third light beam. In this case the light source may further include a beam splitter for splitting light emitted from the first light emitter into the first and second light beams. Alternatively, the light source may include a first light emitter for emitting the first light beam, and a second light emitter for emitting the second light beam, and a third light emitter for emitting the third light beam. The first, second and/or third light emitters may be light emitting diodes.

The light source may further include a controller, the controller configured to generate the first, second and third light beams in a repeated sequence. Preferably the repeated sequence includes the alternate operation of the first, second and/or third light emitters.

In a further aspect the present invention provides a light source for use in a particle detection system, the light source including: a first light emitter for emitting a first beam of light; a second light emitter for emitting a second beam of light; and an optical system including a transmission zone from which light from the first and second light emitters is transmitted from the light source, wherein the optical system is arranged such that obstruction of the transmission zone by a foreign body results in a substantially equivalent obstruction of both the first and second beams of light.

The first and second light emitters can be semiconductor dies. Preferably they are semiconductor dies housed within a single optical package.

The optical system can further include light directing optics for directing the first and second beams of light from the first and second light emitters to the transmission zone.

The light directing optics may be selected from a group including, but not limited to, a convex lens, a Fresnel lens, and a mirror. Other optical components or combinations thereof can be used.

The transmission zone is preferably forms at least a part of an externally accessible optical surface of the optical system. For example the outside surface of a lens, mirror, window, LED package or the like.

The optical system may further include beam shaping optics adapted to modify a beam shape of either or both of the first and second beams of light.

The beam shaping optics may provide light transmitted from the light source with a beam divergence of approximately 10 degrees.

In this case the beam shaping optics may modify the beam shape of either or both of the beams to extend further in one direction than another, e.g. further horizontally than vertically.

The beam shaping optics can also modify the first and second beams so that they have a different beam shape to each other. The beam shaping optics may modify the first beam of light to have a wider beam shape than the second beam of light.

The beam shaping optics may include one or more beam intensity adjusting elements configured to adjust the spatial intensity of the beam. Beam intensity adjusting elements may be selected from a group including, but not limited to, an optical surface coating, a ground glass diffuser, and an etched glass diffuser.

The first light emitter may emit an ultraviolet light beam and the second light emitter may emit an infrared light beam.

The light directing optics and beam shaping optics can be combined into a single optical element, or comprise an optical arrangement with multiple optical elements. The optical elements can be transmissive or reflective elements.

In a further aspect the present invention provides a particle detection system including a light source and a receiver, the light source as described in any one or more of the above statements.

A light source for a particle detector, including: one or more light emitters adapted to generate at least one light beam having a first apparent size from a distant point of view; an optical system arranged to receive the at least one light beam and transmit the at least one light beam and adapted to cause the transmitted light beam to have a second apparent size larger than the first apparent size from the distant point of view.

The optical system preferably includes a beam diffuser. The diffuser can be a dedicated optical component (e.g. a piece of etched glass) or formed as a surface treatment on an optical component that is used for another purpose.

In another aspect, there is provided, a light source for a particle detector, including: one or more light emitters adapted to generate at least one light beam having components in at least two wavelength bands, and optionally an optical system through which the one or more beams pass; the light emitter(s) and or optical system being configured to cause light in one of the at least two wavelength bands to have a spatial intensity profile which is different to light in another of the wavelength bands.

Preferably the beam width of light in one wavelength band is wider than the beam width of light in another wavelength band. Preferably light in a longer wavelength wavelength band has a narrower beam width than light shorter wavelength wavelength band. Preferably the longer wavelength band includes the infrared or red portion of the EM spectrum. The shorter wavelength band can include light in the blue, violet or ultraviolet portion of the EM spectrum.

In yet another aspect, the present invention provides a light emitter usable in a particle beam detector, the light emitter including: housing including a window portion through which light is emitted; means to generate light in a plurality of wavelength bands; and a light sensitive element arranged within the housing and configured to receive a portion of the light in at least one or more of the wavelength bands emitted by the means to generate light; one or more electrical contacts for enabling electrical connection between the means to generate light, the light sensitive element and an electrical circuit.

Preferably the light emitter includes a plurality of light emitting elements adapted to emit light in a corresponding wavelength band.

The light sensitive element can be a photo diode or other light sensitive circuit element.

Most preferably the light emitter elements are LED dies. Preferably the window portion of the housing can be adapted to control the shape of a beam of light emitted.

The housing can be an LED package.

In one form the light emitter includes a plurality of light emitters for emitting light in one or more of the wavelength bands. The plurality of light emitters can be arranged within the housing to achieve a predetermined beam characteristic. In one example, the light emitters corresponding to one wavelength band can be arranged to surround one or more light emitters corresponding to another wavelength band.

In a preferred form the housing can include means to minimise ambient light arriving at the light sensitive element. For example, the means can include one or more filters which attenuate light outside the wavelength bands emitted by the light emitting elements. Alternatively, it can include one or more baffles or walls arranged within the housing such that the light sensitive element is substantially shielded from receiving direct light from outside the housing.

In a further aspect the present invention provides a method of determining the output strength of a light emitting element of a light source in a particle detector. The method including illuminating the light emitting element in accordance with a modulation pattern including "on periods" in which the light emitter is emitting light and "off periods" in which no light is emitted by the light emitter; detecting the output from the light emitting element in one or more on periods and one or more off periods; correcting the detected light output in one or more on periods on the basis of the measured light level in the one or more off periods. For example, the correction may including subtracting the off period measurement from an adjacent on period measurement. Alternatively, the on or off periods may be accumulated or averaged over some predetermined number of corresponding on or off periods to determine the light output level.

In another aspect the present invention provides a light source for a particle detector including at least one light emitter of a type described herein.

The light source can include a modulation circuit component adapted to control an illumination pattern of the light source and a feedback circuit component electrically connected to the light sensitive element and adapted to receive an input therefrom and output a control signal to the modulation circuit.

The modulation circuit can be adapted to vary one or more of:
  the duration of illumination;
  the intensity of illumination;
  the voltage applied to a light emitter; or
  the current applied to a light emitter,
  on the basis of a level of or variation in the received feedback signal received.

In a further aspect, the present invention provides a method in a light source of a particle detector, the method including: illuminating at least light emitter of the light source according to a first modulation pattern, the pattern including a plurality of illumination pulses; receiving a feedback signal; adjusting the modulation pattern in response to the feedback signal.

The method can include adjusting at least one of:
  the duration of illumination;
  the intensity of illumination;
  the voltage applied to a light emitter;
  the current applied to a light emitter.

Preferably the feedback signal is generated by a light sensitive element arranged to monitor the light output at least one light emitting element of the light source.

The feedback signal can be a signal adapted to compensate for a predetermined characteristic of at least one light emitter of the light source. The predetermined characteristic can be a temperature response of a light emitter.

In an embodiment of the present invention the step of adjusting the modulation pattern in response to the feedback signal can include adjusting the modulation pattern to encode data relating to the output intensity of at least one light emitter of the light source. For example, one or more modulation pulses may be, inserted into, or adjusted in, the modulation pattern to transmit light emitter output data to a receiver of the output of light.

In another aspect of the present invention there is provided a component for a beam detector including:
- a housing having at least one side defining at least one internal volume, the at least one wall including an optically transmissive wall portion through which light may pass into or out of the housing;
- an electro-optical system within the internal volume adapted to transmit and/or receive light through an optically transmissive wall portion of the housing;
- a foreign body detection system adapted to detect a foreign body on or near an outer surface of the optically transmissive wall portion, and including a light source adapted to illuminate the outer surface and any foreign body on or near the outer surface;
- a light receiver to receive light scattered from the foreign body in the event one is illuminated, and generate an output signal;
- a controller adapted to analyse the output signal and apply fault logic to determine the presence of a foreign body in the event that one or more criteria are met and take an action.

The light receiver can be any one of:
- a photo diode; and
- part of a light sensor array used to detect particles in use.

The light source can be mounted within the internal volume. Alternatively it can be mounted outside the housing.

In a first aspect the present invention provides a method, in a particle detection system comprising one or more light sources and a receiver arranged so that light from the one or more light sources traverses an area to be monitored for particles and is received by the receiver, and a controller programmed to monitor for the occurrence of one or more predefined alarm and/or fault conditions based on at least one received light intensity threshold; the method including: providing at least one initial light received intensity threshold for use by the controller during a commissioning period; and providing at least one first operational received light intensity threshold for use during an operational period following the commissioning period.

Preferably a received light intensity threshold provided during the commissioning period includes a minimum received light intensity threshold, below which a fault condition may be indicated.

The received light intensity threshold provided during the operational period can include a minimum received light intensity threshold, below which either a fault condition or alarm condition may be indicated.

The minimum received light intensity threshold in the commissioning period can be above a minimum received light intensity threshold during at least a portion of the operational period.

The method can further include: providing at least one second operational light intensity threshold, after the passing of a delay period, at least one second operational light intensity threshold being for use during at least part of the operational period following the delay period.

The second operational intensity threshold can be based on one or more measurements of received intensity during the delay period.

This second operational light intensity threshold is preferably higher than at least one first operational light intensity threshold. The second operational light intensity threshold can be lower than at least one initial light intensity threshold.

The method further include: determining the passing of the delay period. The step of: determining the passing of the delay period can be performed automatically by the controller; and/or upon the receipt of an command signalling the end of the delay period.

If the received light includes a plurality of wavelength components the method includes: determining the occurrence of at least one predefined alarm condition based on the received light intensity at two or more wavelengths. The method can include, determining the occurrence of one or more predefined alarm conditions based on combination of the received light intensity at two or more wavelengths.

The method can further include, initiating the operational period after the commissioning period. Initiating the operational period can be performed, automatically, e.g. based in a timer; or upon the receipt of an initiation command.

In a further aspect the present invention provides a controller for particle detection system comprising one or more light sources and a receiver arranged so that light from the one or more light sources traverses an area to be monitored for particles and is received by the receiver, the controller being programmed to monitor for the occurrence of one or more predefined alarm and/or fault conditions based on at least one received light intensity threshold; said controller being adapted to perform a method as described herein.

The controller can initiate an action upon the occurrence of one or more predefined alarm and/or fault conditions. For example the action can be the generation of an alarm or error signal.

The present invention also provides a particle detection system including such a controller. The particle detection system can further includes, a receiver for receiving light; one or more light sources arranged to emit light at one or more wavelengths, so that light from the one or more light sources traverses an area to be monitored for particles and is received by the receiver. Preferably each light source is a light emitting diode. The receiver can include an array of light sensor elements, e.g. the receiver can be a video camera.

A further aspect of the present invention can also provide a method of commissioning and operating a particle detection system, comprising: arranging one or more light sources and a receiver so that light from the one or more light sources traverses an area to be monitored for smoke before being received by the receiver; and performing the method which is an embodiment of the first aspect of the present invention.

In a further aspect there is provided a particle detection system for monitoring a volume, the system including: at least one transmitter adapted to transmit one or more light beams; a receiver adapted to receive said one or more light beams from at least one transmitter after traversing the volume being monitored; a controller adapted to determining the presence of particles in the volume on the basis of the output of the receiver; and means for determining a light output intensity of a transmitter for use in particle detection.

The means for determining a light output intensity of the transmitter are associated with the transmitter. The means for determining a light output intensity of the transmitter can include one or more filters selectively able to be selectively positioned in a path of a beam of light emitted by the transmitter. The transmitter can include mounting means configured to receive one or more filter elements to enable the intensity of the light output by the transmitter to be set to a determined level.

The means for determining a light output intensity of the transmitter can include electronic control means adapted to electronically control the light output of the transmitter. The electronic control means can include one or more switches able to be manually controlled to select the a light output intensity for the transmitter.

The electronic control means may be in data communication with a receiver and is adapted to receive control information from the receiver relating to the received light level form the transmitter, and is adapted to control the light output of the transmitter in response to said control information.

The means for determining a light output intensity of a transmitter for use in particle detection can be associated with the receiver.

The transmitter can be adapted to transmit a plurality of signals at different intensity levels. In this case the means for determining a light output intensity of a transmitter for use in particle detection can include, means associated with the receiver to determine the received light intensity level for the at the plurality of signals transmitted at different intensity levels and compare the received light intensity level to one or more criterion to determine the a light output intensity of the transmitter for use in particle detection.

The transmitter can be adapted to transmit a repeated pattern of signals including a plurality of signals at different intensity levels; and the receiver can be adapted to selectively receive the one or more signals in the repeated pattern determined to be used in particle detection.

The transmitter may include means for generating a repeated pattern of signals including a plurality of signals configured to produce different received light levels at a receiver of the detection system.

The particle detection system is most preferably a beam detector.

The repeated pattern of signals can include signals transmitted with different intensity levels. The repeated pattern of signals can include signals of different durations.

In another aspect the present invention provides a transmitter for a particle detection system, including: at least one light source to generate a beam of light at least one wavelength; a housing in which the light source is mounted; one or more filters selectively mountable with respect to the light source for selectively attenuating the beam of light.

The transmitter can includes a power source to powering the at least one light source.

The transmitter can includes control circuitry to control an illumination pattern of the at least one light source.

In yet another aspect the present invention provides a receiver for a particle detection system: at least one light sensor for measuring the level of light received from a transmitter of a particle detection system; a controller to selectively activate the light sensor to receive signals. The controller can be adapted to selectively activate the light sensor to predetermined receive signals transmitted by a transmitter of a particle detection system.

The predetermined signals transmitted by a transmitter can be predetermined on the basis of the measured level of light received by the sensor in an earlier time period.

The test filter comprising at least one sheet like filter element, and being configured to transmit light in a first wavelength band transmitted by the particle detector to a different extent than light in a second wavelength band transmitted by the particle detector. Preferably, the test filter transmits a light in a shorter wavelength and emitted by the particle detector less than it transmits light in a longer wavelength band transmitted by the particle detector.

The test filter may include one or more sheets of filter material.

In one embodiment, a sheet or sheets of filter material may be formed of a material such that differential transmission at the two wavelengths is achieved. Alternatively, one or more of the filter elements can be treated or impregnated with colour selective transmissive material. The material in this case can be a dye.

In a preferred form the test filter includes a plurality of filter elements combined at such a manner to achieve predetermined transmission characteristic. Preferably, the transmission characteristics mimic smoke at a predetermined concentration. The plurality of sheets can be combined in such a manner to provide a selectable transmission characteristic.

In one embodiment, a sheet or sheets of substantially transparent material to which has been added particles in a predetermined size range corresponding to particles to be detected by the detector under test. Most preferably, the particles are between 0.2 and 1.0 micron in diameter.

In a further embodiment a filter element may have a surface treatment to create a desired absorption characteristic. In one form, a filter element can include a textured surface. The textured surface can be caused by, for example, mechanical abrasion, particle blasting, chemical or laser etching.

In an alternative embodiment, third form, surface is printed with predetermined number of dots corresponding to the predetermined transmission.

The filter elements may reflect or absorb light which is not transmitted. However, absorption is typically more convenient.

In a first aspect present invention provides a receiver in a particle detector, said receiver including at least one receiver element adapted to receive light and output a signal indicative of the received light intensity at plurality of spatial positions; and an optical system including at least one wavelength selective element configured to receive light at a plurality of wavelengths simultaneously and transmit light in two or more wavelength bands to the one or more sensor elements such that an output signal indicative of the received light intensity in the at least two wavelength bands can be obtained.

In a preferred form the receiver is configured to measure the received light intensity at a plurality of spatially separate positions in a plurality of wavelength bands substantially simultaneously.

In one form of the invention, the wavelength selective element can include a one or more filter elements placed in a light path before the receiver. Most preferably, the filter element or elements includes a mosaic dye filter. Alternatively, the wavelength selective element can include one or more light separating elements, e.g. prisms, diffraction gratings, or the like. In a further alternative, the light separation element can be combined with the light sensor element, and comprise a multi-layered light sensitive element wherein respective layers of the light sensitive element are configured to measure the intensity of light in a corresponding wavelength band.

In a particularly preferred form, the wavelength bands of interest include an infrared band and an ultraviolet band. In this example, the wavelength selective elements can be adapted to be infrared selective and ultraviolet selective.

In some embodiments of the present invention the wavelength selective element may be adapted to split the incoming beam of light into respective wavelength components and direct each wavelength component to a corresponding sensor or subset of elements of a sensor.

In a further aspect the present invention provides receiver for a beam detector including filtering means having multiple passbands. In one form, the filtering means can include a multiple passband interference filter. For example, such a filter may be arranged to selectively transmit in first passband sensor a long wavelength and one or more harmonics of that wavelength. For example, the filter can be designed to transmit substantially all of the light at 800 nanometers and 400 nanometers while blocking a large majority of light at other wavelengths. The filtering means can include a plurality of filters. For example, the plurality of filters can include more than one interference filter or plurality of dye filters or the like. Said plurality filters can be arranged in a predetermined spatial pattern such that light in different passbands falls on different portions of a sensor of the receiver.

In a further aspect of the present invention there is provided a projected beam particle detector including a receiver of the type described above. Preferably, the particle detector includes a polychromatic light source. Most preferably, the light source can be adapted to emit light in a plurality of wavelength bands simultaneously. In a particularly preferred embodiment, the light source includes synchronously operated monochromatic light sources. However, it may alternatively include a polychromatic light source. The polychromatic light source can include xenon flash tube or krypton light source. Alternatively, the light emitter may be a combination of a phosphorescent material and light emitter arranged to illuminate the phosphorescent material. The light emitter may, for example be an LED.

In a further aspect of the present invention there is provided a transmitter for a beam detector including a light source adapted to emit light in a plurality of wavelength bands corresponding substantially to respective passbands of filter of the receiver of the beam detector.

In a further aspect the present invention provides a beam detector comprising at least one receiver and transmitter made in accordance with the foregoing aspects of the invention.

According to one aspect of the invention, there is provided a smoke detector including:
 a transmitter adapted to emit a light beam;
 a receiver having a light sensor with a plurality of sensor elements, for detecting the light beam, each of the sensor elements being adapted to generate an electrical signal related to the intensity of light impinging upon it;
 the transmitter and received being arranged such that at least a portion of a light beam from the transmitter is received by the receiver;
 a beam diffusing optics located in a path of travel of the light beam to the receiver, for forming a diffused image of the light beam on the light sensor, and
 a controller that processes electrical signals generated by a plurality of the sensor elements to determine the intensity of the received beam, and apply alarm and/or fault logic to the intensity data to determine if a predetermined condition is fulfilled, and initiate an action if the predetermined condition is fulfilled.

The beam diffusing optics can include a lens which focuses the light beam at a point which is not coincident with the sensor. The beam diffusing optics can optionally include a diffuser which may be placed between the transmitter and the light sensors. A diffuser and lens can be used together.

The diffused image of the beam preferably covers a plurality of sensor elements on the sensor of the receiver. For example it can cover between 2 and 100 elements. Preferably it covers between 4 and 20 sensor elements, although it may be more depending on the size and density of sensor elements on the sensor. The diffused image of the beam is preferably larger than a sharply focused image of the beam would be.

The controller is preferably adapted to combine the received signals from a plurality of sensor elements to determine the received light level. In one form the measured light level from a plurality of sensor elements are added. Prior to adding the signal levels of each contributing sensor element can be weighted.

The controller may determine a centre-of-signal position corresponding to an image of a beam on the light sensors, and weight the signal from each sensor element according to a distance between each sensor and the centre-of-signal position.

The transmitter may transmit a beam of light having components in two or more wavelength bands.

According to another aspect of the invention, there is provided a method for detecting smoke, including:
 transmitting a light beam from a transmitter toward a receiver having a sensor comprising multiple sensor elements;
 arranging a receiver so that it receives the beam;
 forming a diffused image of the light beam on the sensor;
 generating electrical signals related to the intensity of the received light level detected by at least those sensor elements of the multiple sensor elements on which the beam impinges;
 determining the intensity of the received beam based on a plurality of the signals;
 applying an alarm and/or fault logic to the received determined intensity; and
 initiating an action if a predetermined alarm and/or fault condition is determined.

The step of forming a diffused image of the beam optionally comprises defocusing the light beam such that it is focused at a position that is not coincident with the light sensor.

Alternatively or additionally, the step of diffusing the beam may include placing a diffuser between the transmitter and the sensor.

The step of determining the intensity of the received beam can include combining a plurality of the received signals. The signals can be weighted in the combination. For example the method can include determining a centre of signal position of the diffused image of the beam and weighting the signals according to the distance of their corresponding sensor element from the centre of signal position.

In a first aspect the present invention provides a component for a particle detection system including, a first processor adapted to intermittently receive data from an image capture device and to process said data; a second processor communicatively coupled with the first processor and adapted to selectively activate the first processor.

The second processing device can be additionally configured to perform one or more of the following additional functions of the particle detection system, communication with an external data communication system connected to the particle detector; control of one or more interface components of the system; monitoring of a fault condition of the component, or the like.

Preferably the second processor is of lower power consumption than the first processor.

The component preferably also includes imaging means to receive one or more optical signals from a transmitter associated with the particle detection system.

In a second aspect of the present invention there is provided a method in a particle detection system. The method includes, monitoring an activation period of a first processor using a second processor; activating the first processor in response to a signal from the second processor; and performing one or more data processing steps with the first processor.

The method can include deactivating the first processor upon completion of one or more processing tasks.

The first processor is preferably adapted to process video data from a receiver of the particle detection system.

In one aspect the present invention provides a light source for a particle detector, including:
- at least one light emitter for emitting at least one beam of light for illuminating a part of a region being monitored;
- a battery for supplying electrical power to the light source;
- a battery monitor for measuring at least one of the voltage of the battery or its current output;
- a controller configured to, control the illumination of at least one light emitter of the light source and to receive at least one of, the voltage of the battery or its current output, and to determine a valve indicative of a remaining expected battery life. Preferably, the controller is adapted, in the event that the remaining expected battery life is less than a predetermined period of time, to generate an indication of the remaining expected battery life.

Preferably the light source includes an environmental monitor to monitor an environmental factor affecting the remaining expected battery life, e.g. temperature.

The predetermined period of time is preferably longer than a period between scheduled, recommended or mandated servicing intervals for the light source.

In another aspect the present invention provides environmental monitoring system including:
- a beam detector subsystem including at least one transmitter adapted to emit one or more beams of light across a region being monitored and at least one receiver, adapted to receive at least one beam of light emitted by a transmitter;
- at least one additional environmental monitor adapted to sense an environmental condition associated with the region being monitored and to communicate an output, via an optical communication channel, to a receiver of the beam detector subsystem.

In a preferred form, the optical communications channel can be implemented by modulating a beam output by one or more transmitters of the beam detection subsystem.

Alternatively, the optical communications channel can include a light emitter associated with the one or more additional environmental monitors and arranged to lie within a field of view of a receiver of the beam detector subsystem wherein the light emitter is adapted to be modulated to communicate a sensed condition by an associated environmental monitor.

In a particularly preferred form the light receiver of the beam detector subsystem can include one or more sensors including a plurality of sensing elements adapted to measure a received light intensity at a plurality of spatial positions. Such a system can be used to simultaneously monitor an optical communications channel and a particle detection beam of one or more transmitters of the beam detector subsystem.

In a further aspect of the present invention there is provided the beam detection system comprising a plurality of beam detectors; at least one controller in data communication with the detectors and receiving an output from each of said beam detectors. The controller being adapted to correlate the output of at least a pair of beam detectors which are spatially substantially spatially coincident for at least part of their beam length and in the event that a predetermined correlation condition exists determining that either particle detection event or a fault condition has occurred. In one form, the correlation includes a temporal correlation. The correlation may include a particle detection level correlation. In a simple form, the correlation may simply be performed by comparing whether the particle detection level of two or more beam detectors are substantially equal, alternatively, a particle detection profile for a plurality of beam detectors may be compared to one another to determine the extent of correlation between them.

In another aspect of the present invention there is provided a method of operating a particle detection system including plurality of beam detectors having beams that can substantially coincident at least one point. The method including receiving an output from the plurality of beam detectors, determining if a correlation condition exists between at least two of the outputs, and if a predetermined correlation condition exists; determining either a particle detection event or false alarm event has occurred according to predetermined particle detection and/or fault logic. The alarm can include cross correlating a time varying particle detection profile of two detectors. It can also or alternatively include determining a correlation between a particle detection state i.e. an alarm level or alarm threshold crossing of the two or more detectors.

Throughout this specification the term "beam" will be used in reference to the output of a light emitter such as an LED. The beam will not necessarily be collimated or confined to a single direction, but may be divergent, convergent or of any suitable shape. Similarly, "light" should be understood to broadly mean electromagnetic radiation and is not confined to the visible portion of the electromagnetic spectrum.

In another aspect the present invention provides a particle detection system including; at least one light source adapted to illuminate a volume being monitored, said illumination including a pulse train including a plurality of pulses, said pulse train being repeated with a first period; a receiver having a field of view and being adapted to receive light from at least one light source after said light has traversed the volume being monitored and being adapted to generate signals indicative of the intensity of light received at regions within the field of view of the receiver, said receiver being configured to receive light from the at least one light source in a series defined by an exposure time and receiving frame rate; a processor associated with the receiver adapted to process the signals generated by the receiver, wherein the pulses with the pulse train emitted within each plurality of pulses has a temporal position that is related to the receiving frame rate.

A pulse in the pulse train can preferably have a duration about half the exposure time. Preferably the period of repetition of the pulse train is substantially longer than the period between temporally adjacent frames. The frame rate is in any one of the following ranges: 100 fps-1500 fps, 900 fps-1100 fps, 500 fps to 1200 fps. Most preferably the frame rate is about 1000 fps.

The duration of a pulse is preferably between 1 µs and 100 µs. Most preferably the duration of a pulse is about 50 µs.

The exposure time will typically be between 2 and 200 µs. Preferably the exposure time is about 100 µs.

The pulse train can include at least one synchronisation pulse. Preferably it includes 2. The pulse train can include at least one pulse at a first wavelength. the pulse train can include at least one pulse at a second wavelength. The pulse train can include at least one data pulse.

The frame rate and temporal spacing between each of the pulses are selected such that, in at least a first time period, there is changing phase difference between them. the frame rate and temporal spacing between each of the pulses are selected the temporal spacing between each of the pulses is such that each of the pulses in a pulse train substantially fall within a respective exposure.

In another aspect of the present invention there is provided a method in a particle detection system including; at least one light source adapted to illuminate a volume being monitored, a receiver having a field of view and being adapted to receive light from at least one light source after said light has traversed the volume being monitored and being adapted to generate a series of frames indicative of the intensity of light received at regions within the field of view of the receiver, and a processor associated with the receiver adapted to process the signals generated by the receiver, and provide an output; said method including: determining a number of light sources from which the receiver is receiving light.

The method can further include: analysing a plurality of frames output by the receiver to determine the number of light sources.

The method can further include: operating the receiver at a high frame rate during the step of determining the number of light sources; and subsequently operating the receiver at a second lower frame rate.

The method can further include: analysing a plurality of frames from the receiver to identify regions having relatively high variation in received light level between frames to identify candidate positions within the field of view of the receiver.

The method can further include: comparing the variation in received light levels for a position between frames to a threshold.

The method can further include: attempting to synchronise the receiver to a predetermined transmission pattern expected from a transmitter for a candidate position, and in the event synchronisation is successful determining the candidate position is receiving light from a transmitter.

The method can further include: attempting to synchronise the receiver to a predetermined transmission pattern expected from a transmitter for a candidate position, and in the event synchronisation is unsuccessful determining the candidate position is not receiving light from a transmitter.

The step of attempting to synchronise the receiver to a predetermined transmission pattern can include: capturing a plurality of at least partial frames including the candidate location; comparing the received frames to an expected pattern of received light corresponding to a pulse train emitted by a transmitter; attempting to synchronise to the received pattern using a phase locked loop.

The step of comparing the received frames to an expected pattern of received light corresponding to a pulse train emitted by a transmitter; can include determining a reference level of received light representing a time when no pulse is received for the candidate position; comparing a light level received from each pulse to the reference level and if the difference exceeds a predetermined threshold, determining a pulse is received.

The step of comparing the received frames to an expected pattern of received light corresponding to a pulse train emitted by a transmitter; can includes determining whether a series of pulses corresponding to an expected pattern is received.

The method can further include: comparing the determined number of light sources with a predetermined number of light sources; and in the event that the determined number does not match the predetermined number either: repeating the determining step; or signalling a fault.

In order to more clearly explain each of the aspects of the present invention and their implementation, these aspects have each been described in relation to separate embodiments. A person skilled in the art will readily understand how to combine two or more of such embodiments into an implementation of the invention. Thus it should be understood that the invention disclosed and defined in this specification extends to all alternative combinations of two or more of the individual features and aspects mentioned or evident from the text or drawings. All of these different combinations constitute various alternative aspects of the invention.

Throughout this specification the term "beam" will be used in reference to the output of a light emitter such as an LED. The beam will not necessarily be collimated or confined to a single direction, but may be divergent, convergent or of any suitable shape. Similarly, "light" should be understood to broadly mean electromagnetic radiation and is not confined to the visible portion of the electromagnetic spectrum.

As used herein, except where the context requires otherwise, the term 'comprise' and variations of the term, such as 'comprising', 'comprises' and 'comprised', are not intended to exclude further additives, components, integers or steps.

BRIEF DESCRIPTION OF THE DRAWINGS

Illustrative embodiments of the present invention will now be described, by way of non-limiting example only, with reference to the accompanying drawings, in which.

DETAILED DESCRIPTION OF THE EMBODIMENTS

Figure 4:
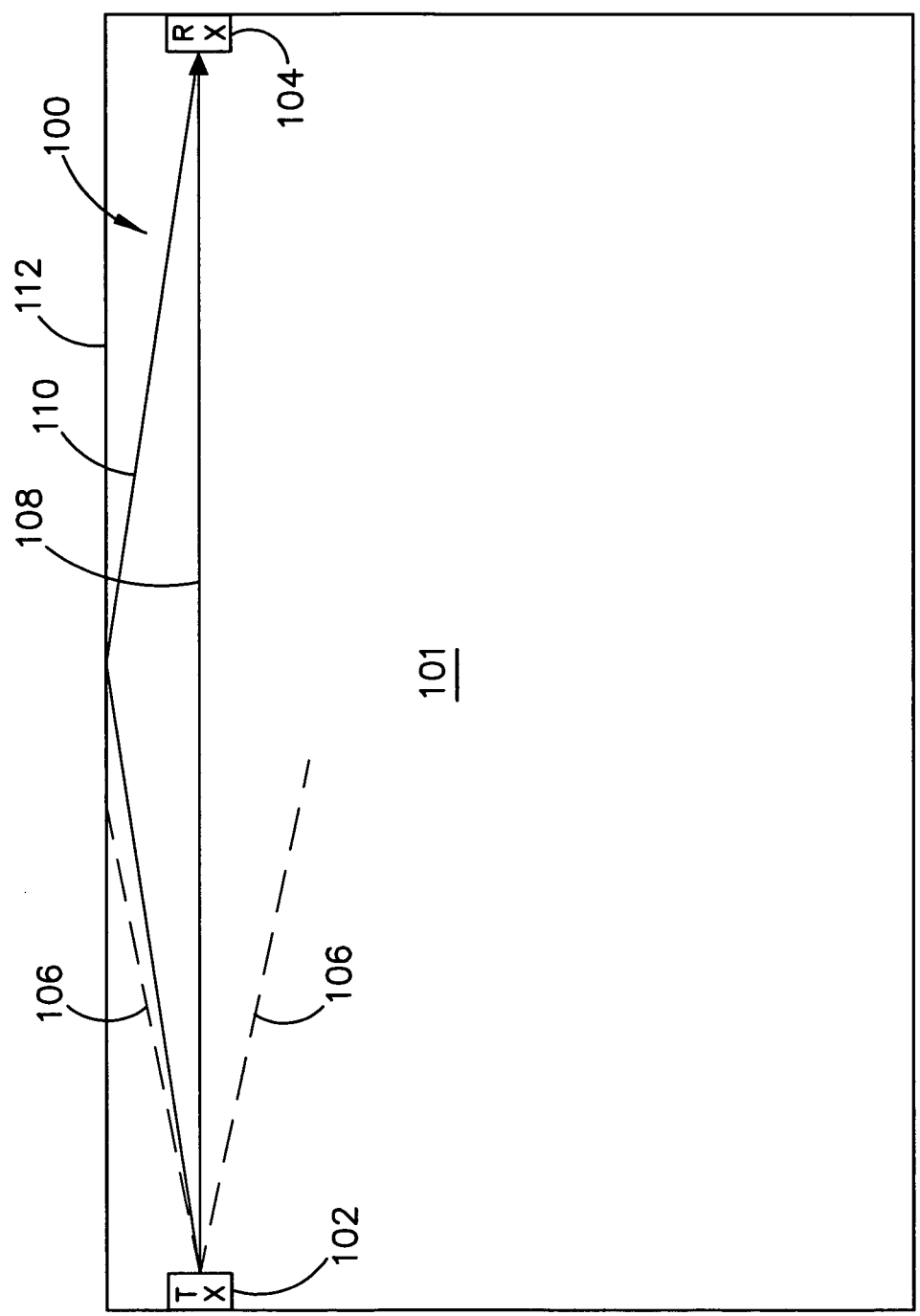
FIG. 4 illustrates a scenario in which a reflection may be caused in a beam detector.

FIG. 4 illustrates a beam detector of the type described above. The beam detector 100 includes a transmitter 102 and a receiver 104. The beam detector 100 is set-up to detect particles in a volume 101, which may be a room for example. The transmitter 102 emits a diverging beam of light over a field of illumination defined by lines 106. The beam of light includes a direct illumination path 108 which arrives without reflection at the receiver 104. Within the field of illumination 106 of the transmitter 102 some rays will arrive at the receiver 104 by a reflected path, e.g. path 110 which reflects off the ceiling 112 defining the volume 101. The present inventors have determined that if certain conditions are fulfilled, the presence of the reflected beam 110 can be ignored. For example, if the received beam satisfies minimum received intensity requirements; and, in the event that the beam includes distinguishable characteristics, e.g. wavelength components and/or polarisation states, that the received beam possesses the predetermined characteristics. In some cases it is relevant whether the beam which is used for detecting particles is the direct beam 108 or the reflected beam 110, for example, in a multiple wavelength system, it may be that the surface finish of the ceiling 112 is such that light in one wavelength band will be reflected more completely than light in a second wavelength band. In the event that these wavelength bands coincide with wavelength bands transmitted by the transmitter 102 that are used for particle detection by the receiver 104, a differential measure of received light intensity in the two wavelength bands will behave differently in the reflected light path 110 than in the direct light path 108. Accordingly, in this case, it is necessary to correctly identify the direct light path beam 108.

Figure 5:
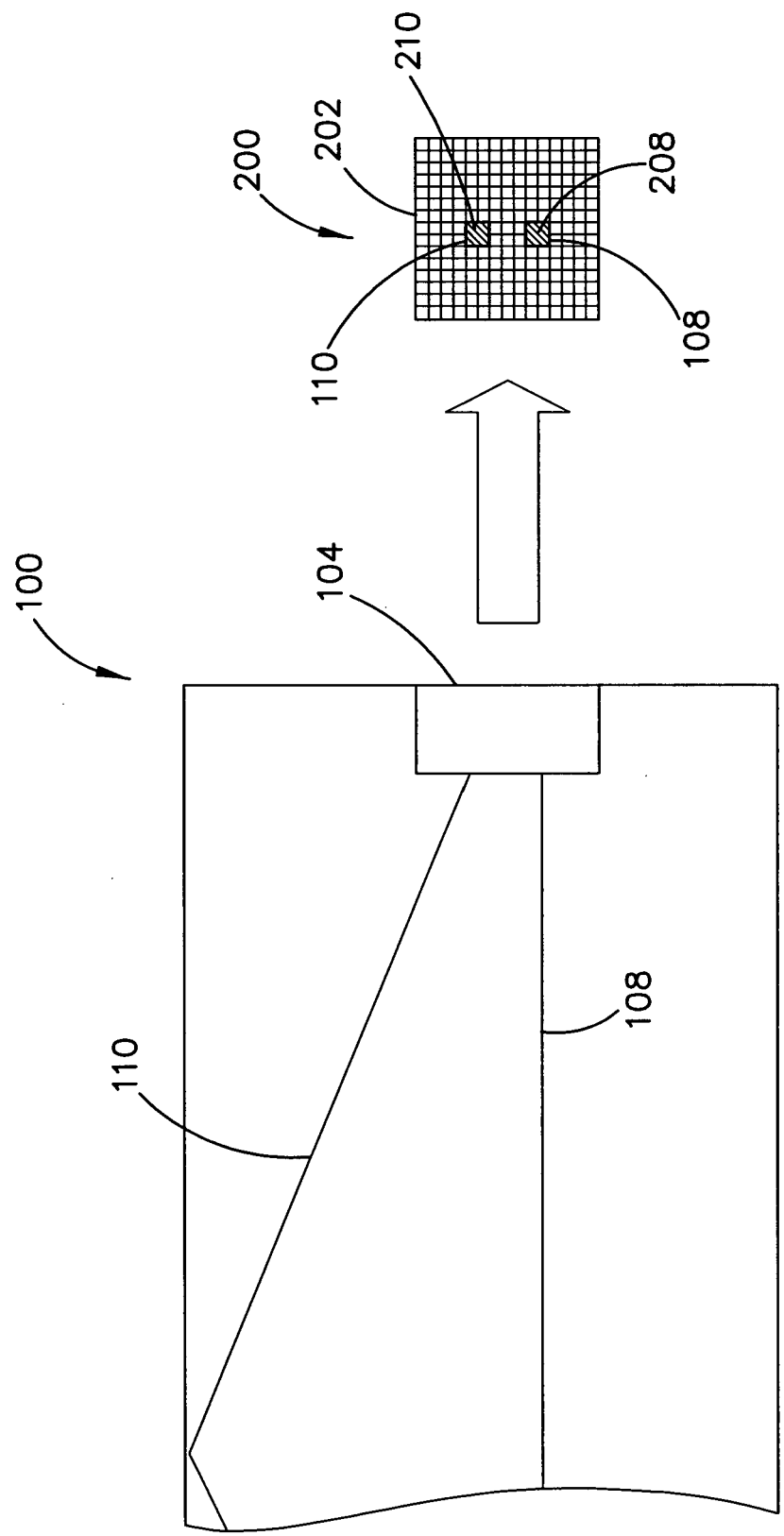
FIG. 5 illustrates a close-up view of a receiver in a beam detector made in accordance with an embodiment of the present invention.

FIG. 5 illustrates one mechanism for determining a direct beam from a reflected beam in such a system. In FIG. 5 corresponding features will be numbered with the same reference numerals as FIG. 4. FIG. 5 illustrates a close-up view of the receiver 104 of the beam detector 100 showing a reflected beam 110 and a direct beam 108. FIG. 5 also shows the detail of the sensor 200 of receiver 104. In this embodiment, the likelihood of distinguishing the direct beam 110 from the reflected beam 110 is improved by providing the light receiver 104 with a sensor having a high spatial resolution. As described above, the sensor 200 of the receiver 104 includes a multiplicity of sensing elements 202 which can independently detect received light intensity at distinct spatial positions. In FIG. 5, by providing a high resolution sensor 200 it can be seen that a group of pixel 208 are illuminated by a direct beam 108 and a separate and distinct group of sensor elements 210 are illuminated by the received reflected beam 110. If the sensor element size was substantially larger it would not be possible to resolve these two received beams into distinct groups of sensor elements. In a particularly preferred form, the spatial resolution of the light sensor is particularly high in the direction of a plane defined by the direct beam and the reflected beam.

In most embodiments the controller of the beam detector can be configured to determine which of the spots, e.g. 210 or 208 has the highest intensity, and to use the highest intensity beam for particle detection. Typically, the brightest received beam will correspond to the direct ray 108. In an extreme case, there may be no sufficient discernable difference between intensity of the two received light beams. In this case, the beam which arrives at the receiver furthest from the reflecting surface is preferably selected as the direct beam as the other beam i.e. a beam nearer the reflective surface, is more likely to be the reflected ray.

In one exemplary embodiment, the resolution of the image sensor is 640×480 pixels.

Figure 6:
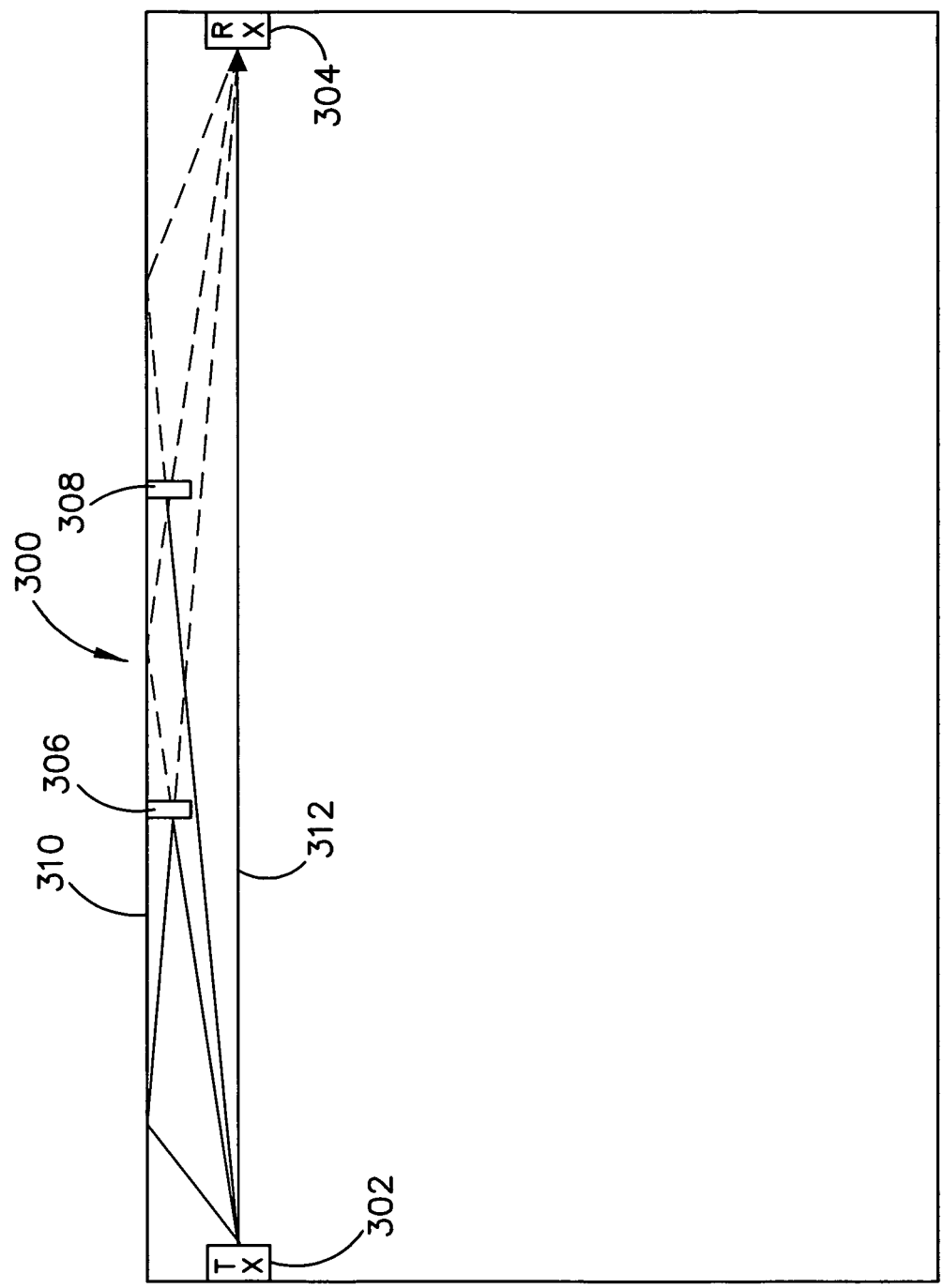
FIG. 6 illustrates a beam detector set-up made in accordance with another embodiment of the present invention.

FIG. 6 shows a further beam detector installation made in accordance with an embodiment of the present invention. In this case, beam detector 300 includes a transmitter 302 and a receiver 304. The operation of the beam detector is substantially identical to those described elsewhere herein. However, the beam detector installation additionally includes two baffles 306 and 308 attached to the reflecting surface 310. The baffles 306 and 308 extend outwardly from the reflecting surface 310 towards the direct beam path 312 and serve to intercept reflected beam paths which could potentially reach the receiver 304. The number and length of the baffles can be chosen to suit the particular installation and may be positioned to extend almost entirely down to the direct beam 312. Alternatively, if accurate positioning is possible, a relatively short baffle can be used if an accurate position of the reflected beam can be determined. Another option involves a longer baffle having an aperture accurately positioned so that the direct beam 312 passes therethrough. As will be appreciated, the same effect can be achieved by placing the transmitter and receiver in close proximity to an existing structure which will act like a baffle, for example, in a warehouse type installation in which the warehouse has a number of horizontally extending ceiling support beams placed beneath the ceiling, the transmitter receiver may be located slightly below the beams such that the beams in effect operate as baffles to prevent interference from reflections off the ceiling's surface.

Figure 7:
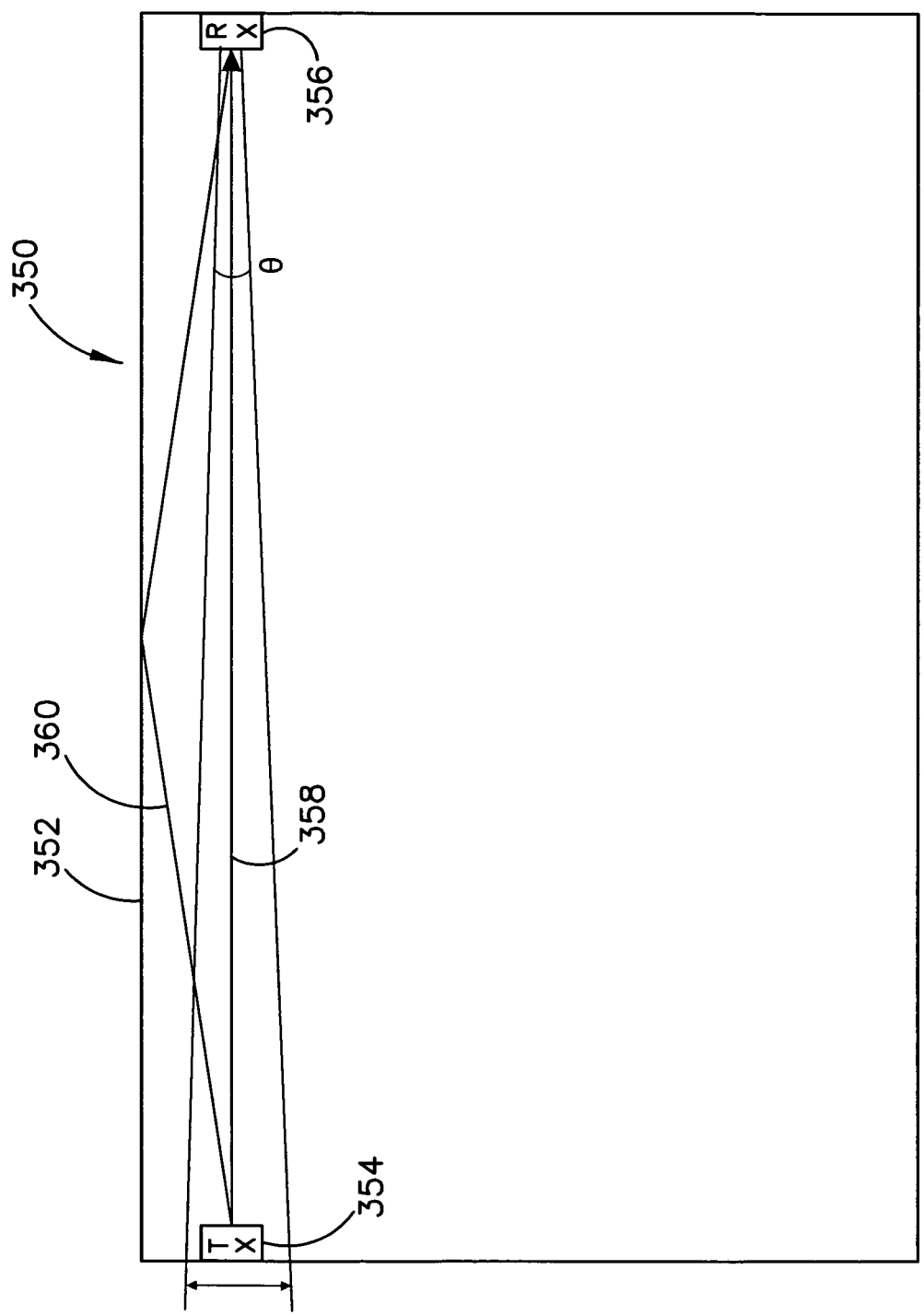
FIG. 7 illustrates beam detector arrangement made in accordance with another embodiment of the present invention.

FIG. 7 illustrates a further embodiment of the present invention. This embodiment shows a beam detector set-up 350 comprising a transmitter 354 and a receiver 356. The transmitter 352 emits a beam or beams of light over a predetermined illumination field and as discussed with the previous embodiments, both direct beams 358 and reflected beams 360 may arrive at the receiver 356. In this embodiment, the receiver is configured such that it has a field of view 8 that is relatively narrow in the direction of the reflection and as such the receiver 356 is unable to 'see' the reflecting surface 362. If the receiver 356 cannot see the reflective surface 362, the only light path to the receiver from the transmitter 354 which will produce a sufficiently strong signal to be discernable will be the direct beam 358. Similarly, the field of illumination of the transmitter 354 can be confined such that it does not illuminate the reflective surface 362. Typically in beam detector installations the reflective surface will be a ceiling of a room being monitored. In this case, the field of view of the receiver 356 and/or the field of illumination of the transmitter 354 will need to be constrained in the vertical direction. Suitable fields of view for field of illumination will have an angle of divergence of between 0° and 5°. However, this requirement will differ depending on the geometry of the system. Clearly a system with a long distance, say a 100 meters between the transmitter and the receiver will require a very narrow angle of beam divergence or viewing angle to achieve this outcome. However, in an embodiment with only 3 meters between the transmitter and the receiver a much wider angle of illumination and field of view is acceptable. Proximity to the reflective surface will also influence the required angles to achieve the aforementioned results.

Figure 8:
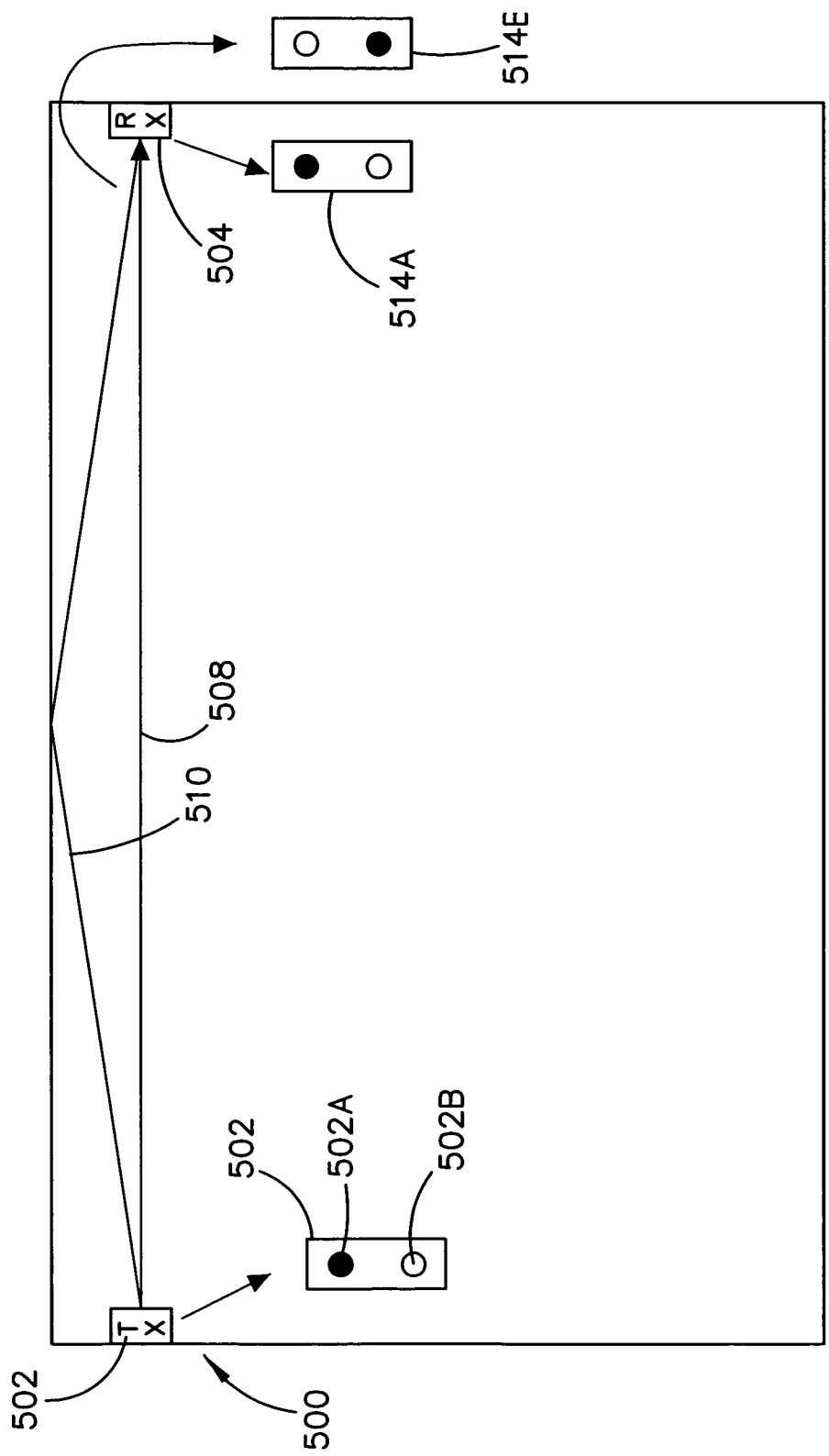
FIG. 8 illustrates another embodiment of the beam detector made in accordance with the present invention.

FIG. 8 shows a further embodiment of a beam detector made in accordance with an aspect of the present invention. In this embodiment, the beam detector 500 includes a transmitter 502 and a receiver 504. The transmitter 502 includes two light emitters 502A and 502B. Each light emitter 502A, 502B emits a beam or beams of light over its respective field of illumination and may direct a direct beam 508 and a reflected beam 510 which arrive at the receiver 504. The two light emitters 502A and 502B are configured to be actuated in predetermined illumination sequence such that the source of a received beam, i.e. which emitter it came from, can be determined by analysing the light received at the receiver 504. In this embodiment, the light which arrives at the receiver 504 via the direct light path 508 will form an image 514A on the receiver sensor (not shown), whereas the light received at the receiver by the reflected light path 510 will form an image on the sensor of the receiver 504 such as that shown at 514B. As will be appreciated, the image formed on the receiver in the two cases (i.e. direct and reflected) differ from each other in that one is a mirror image of the other. The directly formed image 514A preserves the relative positioning of the two light sources 502A and 502B whereas, in the reflected image 514B, the positions of these two sources 502A and 502B are flipped in the plane containing the reflected beam and receiver. Accordingly, by analysing the received images, it is possible to determine which pair of received beams corresponds to the direct beam path 508 and which pair correspond to the reflected beam path 510. In other embodiments of the present invention the two light sources 502A and 502B can be light emitters with different wavelength or polarisation characteristics, rather than being illuminated with different modulation patterns.

As will be appreciated by those skilled in the art any shaped arrangement of light images on the transmitter. For example, a two dimensional ray of distinguishable light emitters can be incorporated into a transmitter to allow determination of the direct or reflected beams from any reflective surface in any orientation with respect to the beam.

Figure 9:
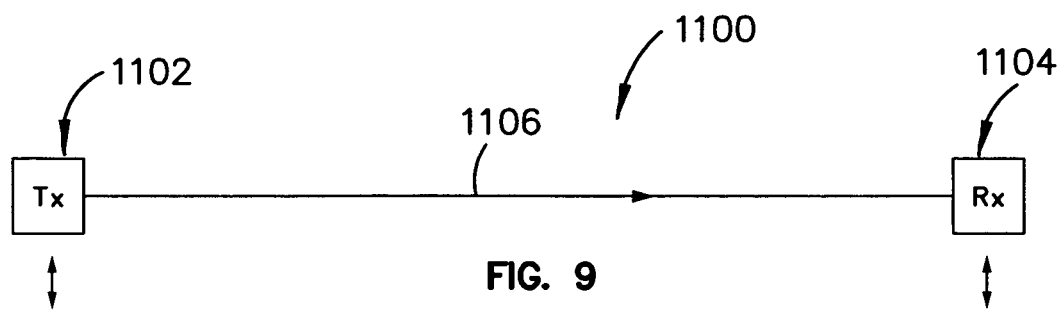
FIG. 9 illustrates schematically an embodiment of the present invention in which the polarisation state of the transmitter and receiver are aligned.

Turning now to FIG. 9, a beam detection system 1100 is illustrated. The beam detection system can be of any of the types described above and includes a transmitter 1102 and a receiver 1104. The transmitter can emit any number of beams of light in any one or more transmission bands. The beam or beams emitted by the transmitter 1102 are received by the receiver 1104. In this embodiment, the transmitter is arranged to transmit polarised light (e.g. vertically polarised light). The receiver 1104 is adapted to receive only light having the same polarisation as that transmitted.

Polarisation of the transmitter can be achieved in a wide variety of ways including by using an inherently polarised light source such as a laser diode or by placing a polarising filter in the beam path of a randomly (or otherwise) polarised light source. Similarly, the polarisation sensitivity of the receiver can be determined by the inherent characteristics of the receiver or by the placement of one or more polarising filters before the sensor elements of the receiver.

In this example, nuisance light such as ambient sunlight which is generally not polarised or is randomly polarised will be substantially rejected by the receiver, whereas all of the transmitted beam (less that proportion extinguished by particles and objects between the transmitter and receiver) will be received by the receiver 104.

Figure 10:
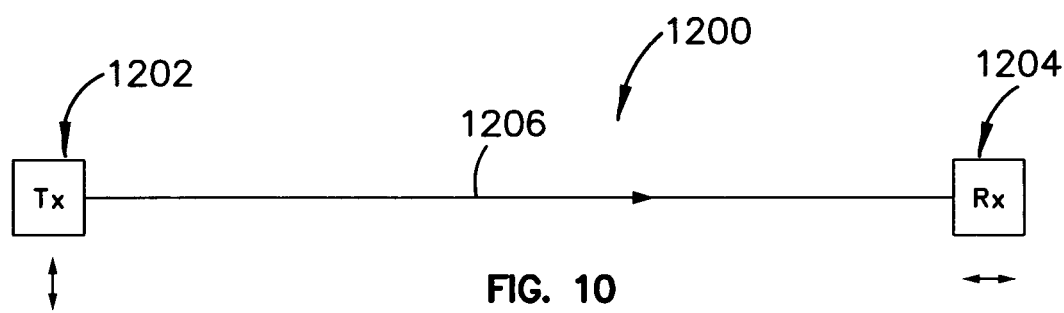
FIG. 10 illustrates schematically an embodiment of the present invention with orthogonally arranged polarisation states at the transmitter and receiver.

FIG. 10 illustrates a similar system to the FIG. 9. The system 1200 in FIG. 10 includes a transmitter 1202 which emits a light beam 1206 that is received by the receiver 1204. In this example, the transmitter is polarised in a first direction (e.g. vertically polarised) and emits at least one polarised beam 1206. The receiver 1204 is arranged to receive light in a polarisation orthogonal to beam transmitted by the transmitter 1202. In this case, the receiver 1204 is adapted to receive horizontally polarised light. Such a polarisation offset presents a benefit in that large particles, like dust, in the path of the beam 1206 may be distinguished from small particles, like smoke. This is because large particles like dust tend to forward scatter light with random polarisation and thus increase the cross-polarised component of light received at the receiver 1204.

Figure 11:
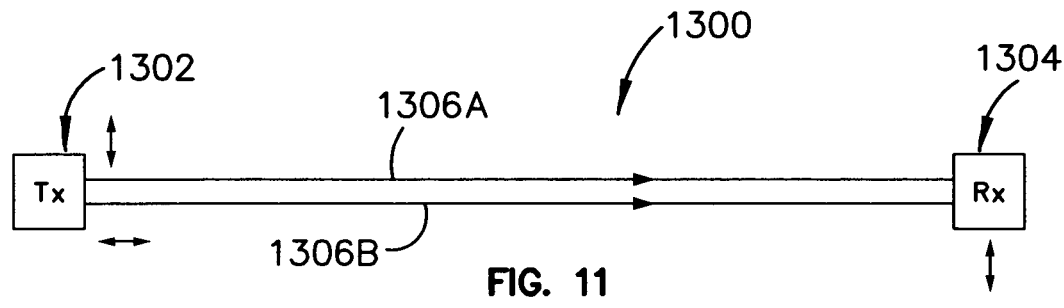
FIG. 11 illustrates an embodiment of the present invention in which two orthogonally polarised beams are transmitted to a polarisation sensitive receiver.

Combinations of the two embodiments described in FIGS. 9 and 10 can be incorporated into a particle detection system. Turning firstly to FIG. 11 the system 1300 includes a transmitter 1302 and a receiver 1304. The transmitter 1302 is adapted to emit light beams 1306A and 1306B. A first of these two light beams 1306A is arranged to be emitted with a first polarisation state whereas the second beam 1306B is emitted with an orthogonal polarisation state. The receiver 1304 is arranged to receive light in a single polarisation only e.g. in the first polarisation state. Accordingly, as will be appreciated both techniques described in relation to FIGS. 9 and 10 may be applied in the same receiver. Preferably, the transmitter 1302 is arranged to generate beams 1306A and 1306B alternately so that the two polarisation state beams arrive at different times at the receiver 1304.

Figure 12:
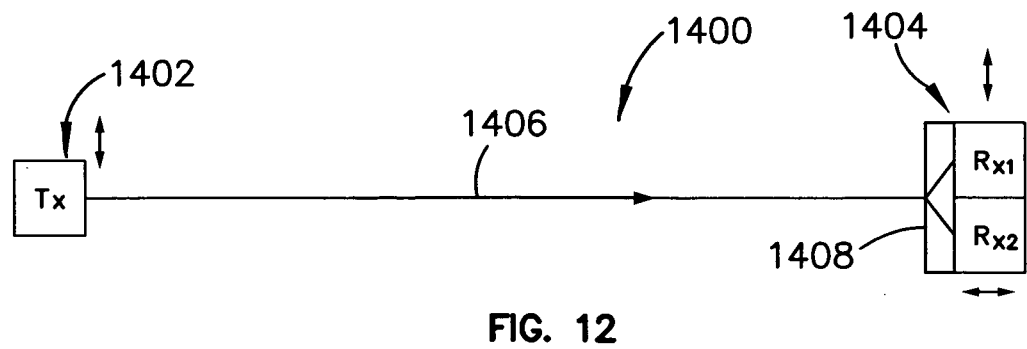
FIG. 12 illustrates an embodiment of the present invention with a transmitter emitting a single polarised beam to be received by two orthogonally polarised receivers.

An alternate system is illustrated in FIG. 12. In this system the beam detector 1400 comprising a transmitter 1402 and a receiver 1404. The transmitter 1402 is configured to emit a vertically polarised beam 1406. The receiver 1404 is adapted to be able to resolve light received in plurality of polarisation states e.g. in vertical polarisation state or a horizontal polarisation state. This can be achieved by having a plurality of adjacent light receiving elements having different polarisations which are operated either concurrently or alternately. In this example, a beam splitting component 1408 is provided prior to the receiver elements to direct beams to each of the receivers.

As will be appreciated by those skilled in the art references the specification to vertical and horizontal polarisation have been selected for convenience only and any polarisations may be used. Moreover, for convenience of description orthogonal polarisation states have been selected to illustrate the present invention. However, the present invention should not be taken as being limited to polarisation states which are either aligned or orthogonal to one another. Other angular offsets between polarisations are possible. Those skilled in the art will be able to determine the appropriate calculations to perform to account for this variation.

One way of achieving variation in polarisation states for a receiver or transmitter is to provide mechanical means for placing polarising filters in the light path. For example, a solenoid can be used as an actuator to move a reciprocating polarising filter into and out of the beam path. Alternatively a rotating filter mechanism can be employed which has plurality of differently polarised filters around a wheel like structure. By rotating the wheel like structure through the light path different polarisations can be achieved over time. Other mechanical arrangements are also possible, for example, the light emitting element of the transmitter 402 could be physically rotated about an axis as could the one or more sensors of the receiver. Other mechanical arrangements will be apparent to those skilled in the art.

Figure 13:
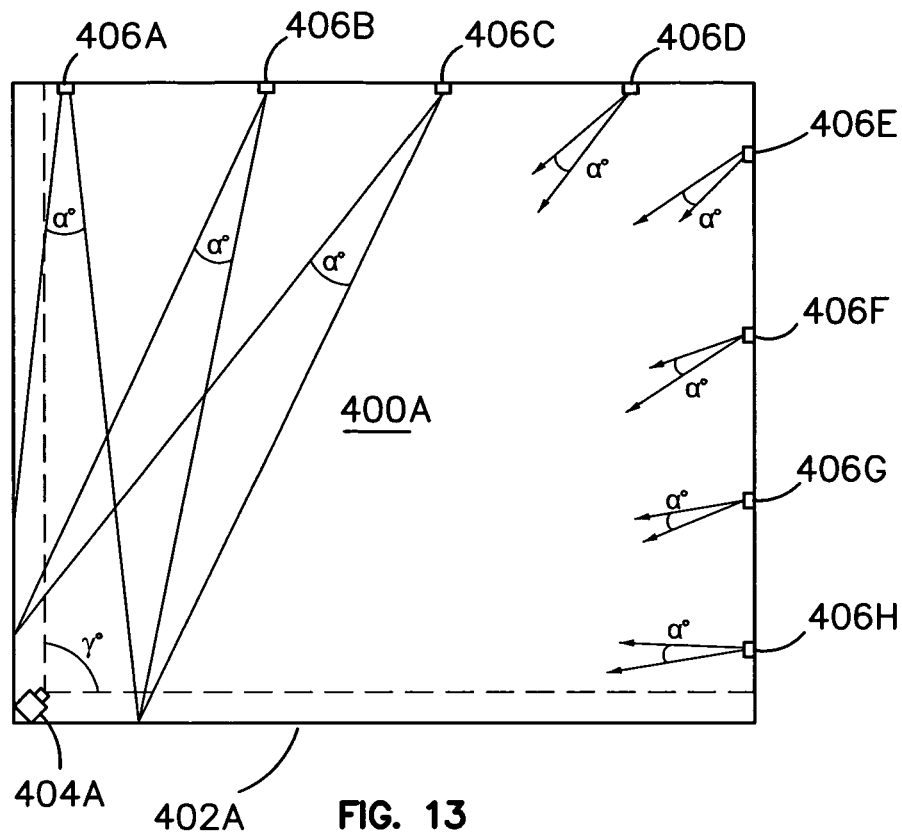
FIG. 13 illustrates a plan view of a volume monitored by a particle detection system operating according to an embodiment of the present invention.
Figure 14:
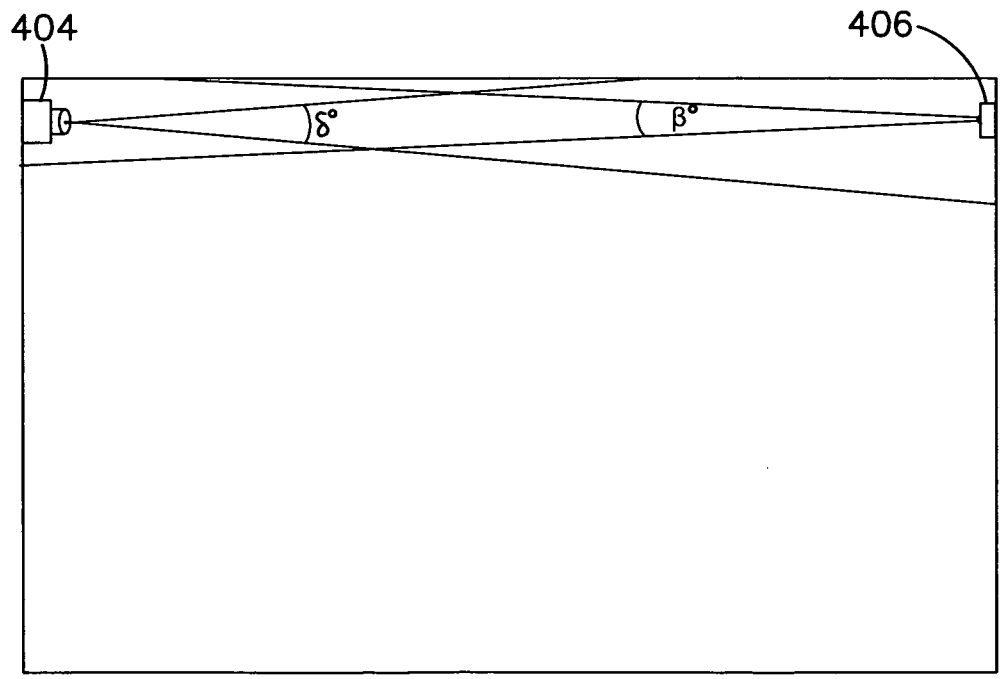
FIG. 14 illustrates a cross sectional view through a volume of FIG. 13 showing the receiver and one transmitter of that system.

FIG. 13 illustrates a plan view of a room 400A in which is installed a beam detector system 402A according to an embodiment of the present invention. The beam detection system includes a single receiver 404A configured to monitor eight transmitters 406A, 406B through 406H. Each of the transmitters 406A to 406H is adapted to transmit light with a horizontal angle of illumination of a degrees. It is also adapted to transmit light with a vertical angle of illumination of β degrees as show in FIG. 14. Similarly the field of view of the receiver 404A differs in its horizontal and vertical extent. In this example, the receiver 404A is adapted to receive light over a viewing angle of γ degrees and vertical viewing angle of δ degrees. In a preferred form of the present invention the horizontal angle of illumination of the transmitters 406A to 406H is wider than their vertical angle of illumination β. Similarly, the receiver 404 has a wider horizontal field of view than it does vertical field of view.

The differential fields of view and fields of illumination of the receiver and transmitter respectively are chosen to account for alignment tolerances in the typical installation. For example, in most installations such as that illustrated in FIG. 13 the transmitters 406A through 406H will typically be installed at the same height as each other and the receiver 404A will be mounted in a plane parallel to the transmitters 406A to 406H. Accordingly, when the image of the transmitters 406A through 406H is received on the light sensor of the receiver 404A they will tend to align on the light sensor. Accordingly, a relatively narrow field of view can be tolerated in the vertical direction for the receiver 404A. However, as will be apparent from FIG. 4 a very wide horizontal field of view is required by the receiver 404A. Similarly, horizontal alignment of the transmitters 406A to 406H is more difficult to achieve than vertical alignment in most installations. This is typically because the range of movement in the vertical plane is more limited and typically walls of a building are relatively parallel in alignment. For this reason an installer may get away with mounting the transmitter and receiver such that their field of view is orthogonal to the plane of the surface on which they are mounted and this will achieve a suitably accurate vertical alignment. However, this may not be the case with horizontal alignment as the angle of illumination of the light sources and angle of reception of the light receiver will vary from the orientation of the surface on which they are mounted due to the geometry of the system being installed. Thus providing an ability for horizontal alignment is necessary and the horizontal field of view of the receiver and horizontal beam width of the transmitters is advantageously relatively wide.

For example, a receiver may be adapted such that its horizontal field of view approaches 90 degrees while its vertical field of view is only around 10 degrees. Similarly, a transmitter may be configured such that its horizontal beam width is around 10 degrees whereas its vertical beam width may be between 3 and 5 degrees.

In order to achieve different horizontal and vertical beam divergences or viewing angles either a transmitter or receiver may be fitted with an optical system including an anamorphic lens.

Figure 15:
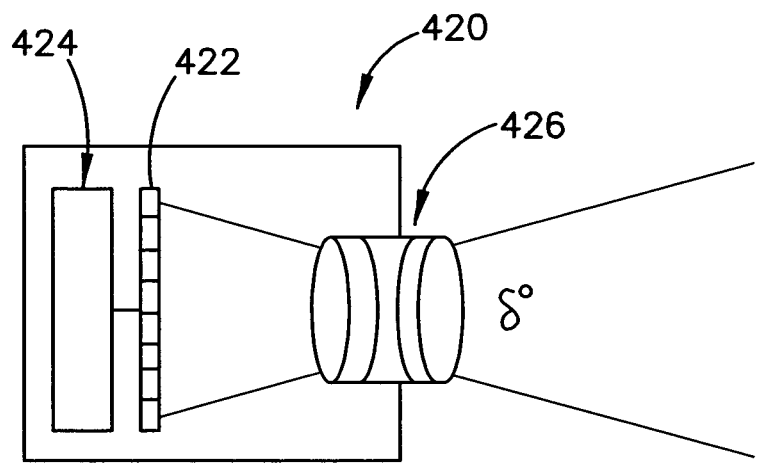
FIG. 15 illustrates a schematic view of a receiver used in an example of the embodiment of the present invention.

FIG. 15 illustrates an exemplary configuration of a receiver such as that described in connection with FIG. 13.

The receiver 420 includes a multi segment light sensor 422 which is coupled to a video readout and processing subsystem 424. The light receiver 920 includes an optical arrangement 426 comprising e.g. a plurality of lenses or other optical components e.g. mirrors, for focusing received light on the sensor array 422. In a preferred form, the anamorphic lens is arranged to provide a substantially different horizontal and vertical field of view for the receiver.

Figure 16:
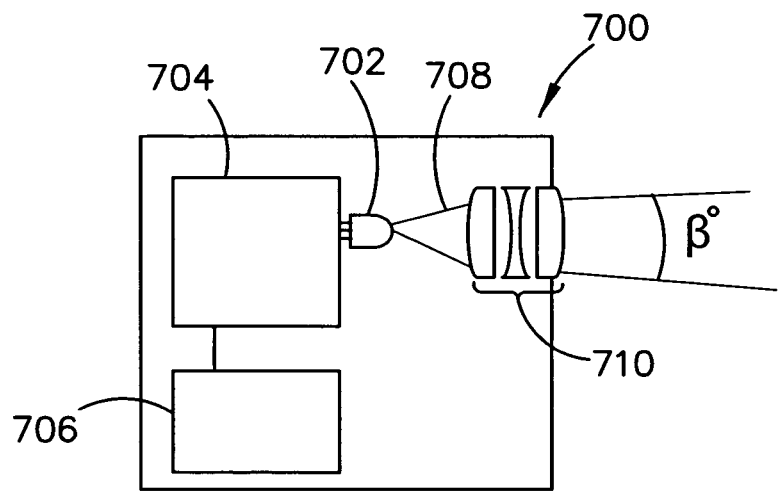
FIG. 16 shows a schematic representation of a transmitter used in an embodiment of the present invention.

FIG. 16 illustrates a transmitter 700 which includes at least one light emitter 702 adapted to emit one or more beams of light in one or more wavelength bands. The transmitter 700 includes control circuitry 704 which is powered by a power source 706 which may, for example be a battery. The light emitter 702 emits a beam of light 708. This beam of light is shaped into a particular dispersion pattern or beam shape by an optical arrangement 710. As described above, the optical arrangement 710 can include one or more anamorphic lenses.

As will be appreciated by those skilled in the art different installations will have different geometrical limitations placed on them and requirements. Accordingly, the present invention should not be considered as being limited to the case where the beam shape of a transmitter e.g. 406 or a receiver e.g. 404 is defined by its vertical or horizontal angles. Rather, the present invention extends to systems in which either or both of the beam width of a transmitter or angular extent of a receiver is different in any two directions whether they are orthogonal with each other or not and whether they are aligned vertically and horizontally or not.

Figure 1:
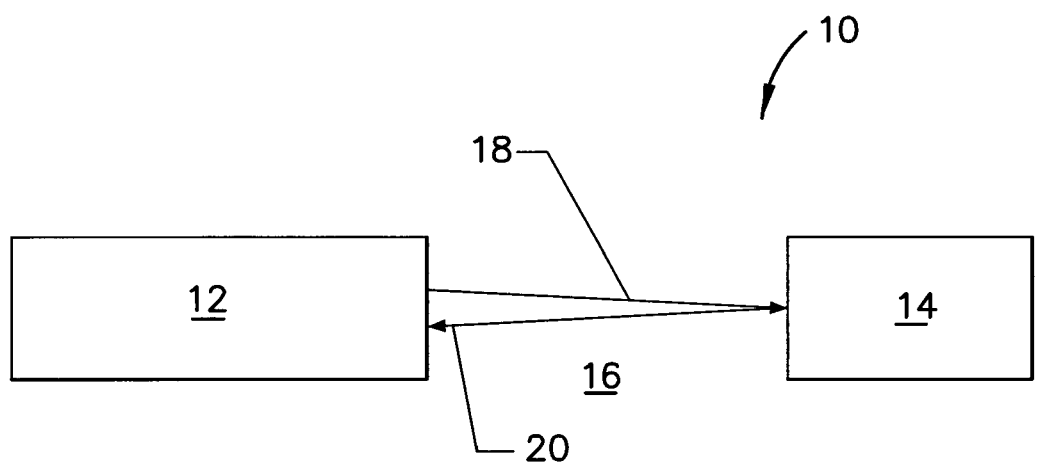
FIG. 1 illustrates a conventional beam detector.
Figure 2:
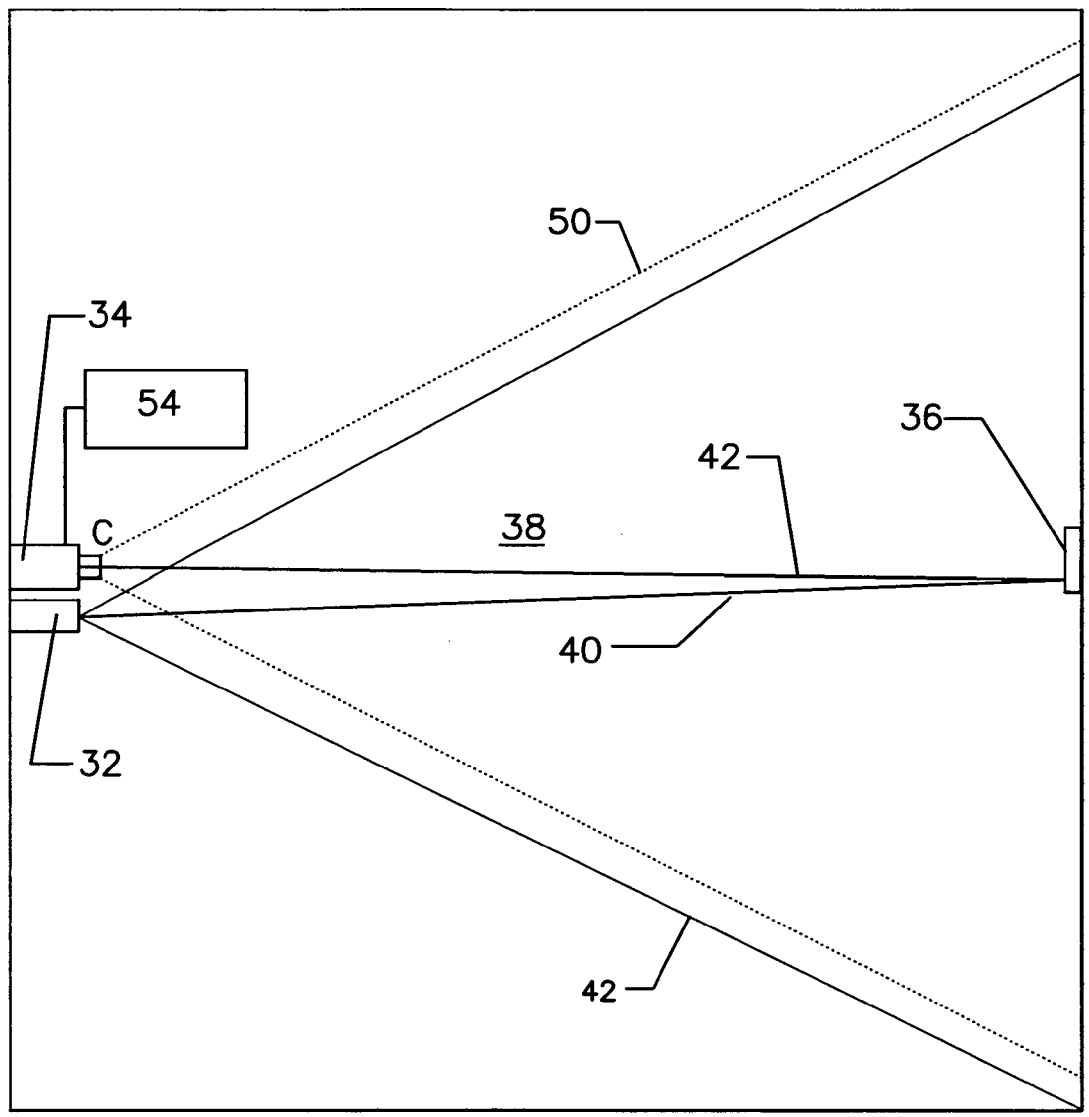
FIG. 2 illustrates a beam detector capable of implementing an embodiment of the present invention.
Figure 3:
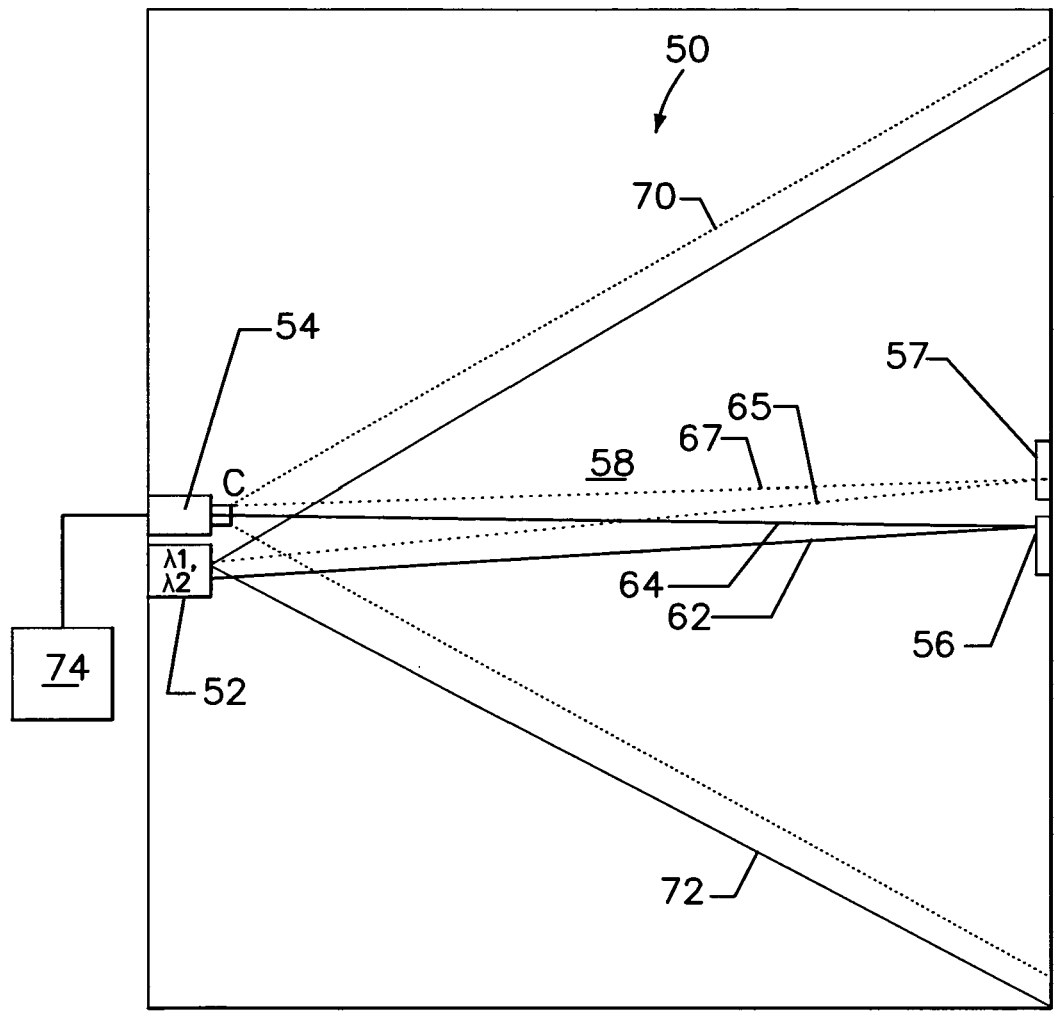
FIG. 3 illustrates a beam detector capable of implementing an embodiment of the present invention.

Irrespective of whether the particle detection system is of the type depicted in FIG. 1, FIG. 2 or FIG. 3 of the drawings, or of a different type, such as that disclosed in PCT/AU2004/000637, PCT/AU2005/001723 or PCT/AU2008/001697 the alignment of the components of the system, eg a light source with the target and the reflection of an emitted beam back to the receiver is important. As mentioned above, there can be a significant distance between the source and the target, thus aligning the light source accurately with the target can be difficult. For this reason it is preferable that an adjustable mounting arrangement is provided which allows the direction of the light source (and/or target—if it is not retro-reflective) to be varied, both at the time of installation, and in the event that movement of the light source and/or the target from its installation position occurs.

Figure 17:
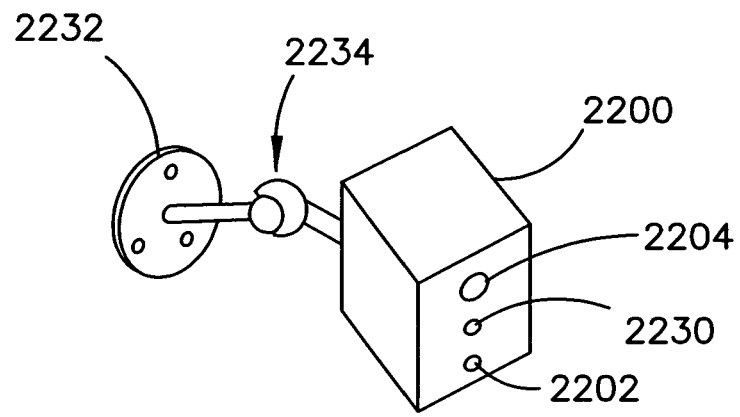
FIG. 17 shows diagrammatically a smoke detector and mounting arrangement according to the invention.

FIG. 17 depicts one embodiment of an alignment beam arrangement which will assist in the alignment of the optical components of a particle detector. The device depicted in FIG. 17 is of a type discussed above with respect to FIG. 2, but the smoke detector can take various different forms. As shown, the smoke detector 2200 includes the light source 2202 and a receiver 2204. In addition, the smoke detector 2200 includes a visual alignment device 2230 of the type adapted to generate an alignment beam 2242 which is axially aligned with the light source 2202 but which is visually observable. The beam 2242 will project onto the target 2206 located some distance away from the smoke detector 2200.

The smoke detector 2200 is provided with a mounting means in the form of a circular plate 2232 which in use will be mounted by screws or the like to a support surface in order to fix the smoke detector 2200 at a appropriate elevation to that support surface. An articulated connection 2234 is provided between the mounting plate 2232 and the smoke detector 2200. The articulated connection can take various forms, which will allow the alignment of the detector to be varied, but being lockable in the selected orientation. A friction lock arrangement is possible, or some form of screw tightening arrangement might be used.

Figure 18:
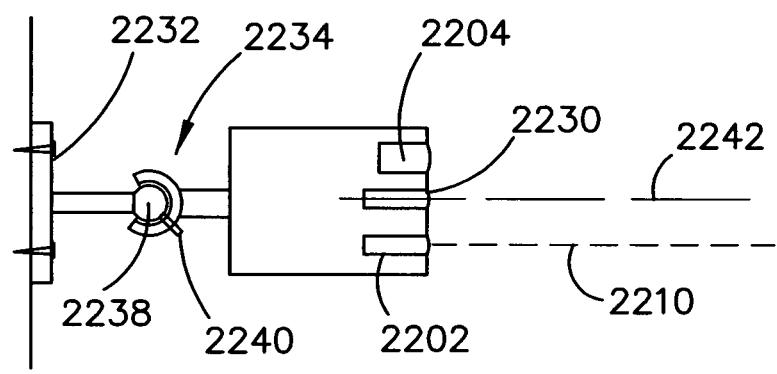
FIG. 18 shows a cross sectional side view of the smoke detector shown in FIG. 17.

As shown in FIG. 18, the articulated connection 2234 comprises a cup 2236 and ball 2238, the ball being able to rotate within the cup. The ball is captively held by the cup so as to allow the smoke detector 2200 to be tilted relative to the support plate 2232, thereby allowing the incident light 2210 to be directed precisely to the target 2206 some distance away. A grubscrew 2240 is provided for locking the ball relative to the cup. Other forms of locking the ball in the cup are possible, including, for example a friction fit.

As mentioned, the alignment beam 2242 is used to facilitate the alignment of the incident light 2210 with the target. Thus, the alignment beam 2242, which would typically comprise a laser beam, is parallel to the incident light 2210. An operator would thus be able to point the alignment beam 2242 at the target or just adjacent to the target to thereby ensure that the incident light 2210 (which is typically not visible) is aimed centrally at the target. Once the incident light 2210 is aimed at the centre of the target, the grubscrew 2240 will be tightened, thereby locking the ball 2238 within the cup 2236. This will ensure that the smoke detector 2200 is optimally aligned and calibration of the system can then take place in the manner described herein.

Figure 19:
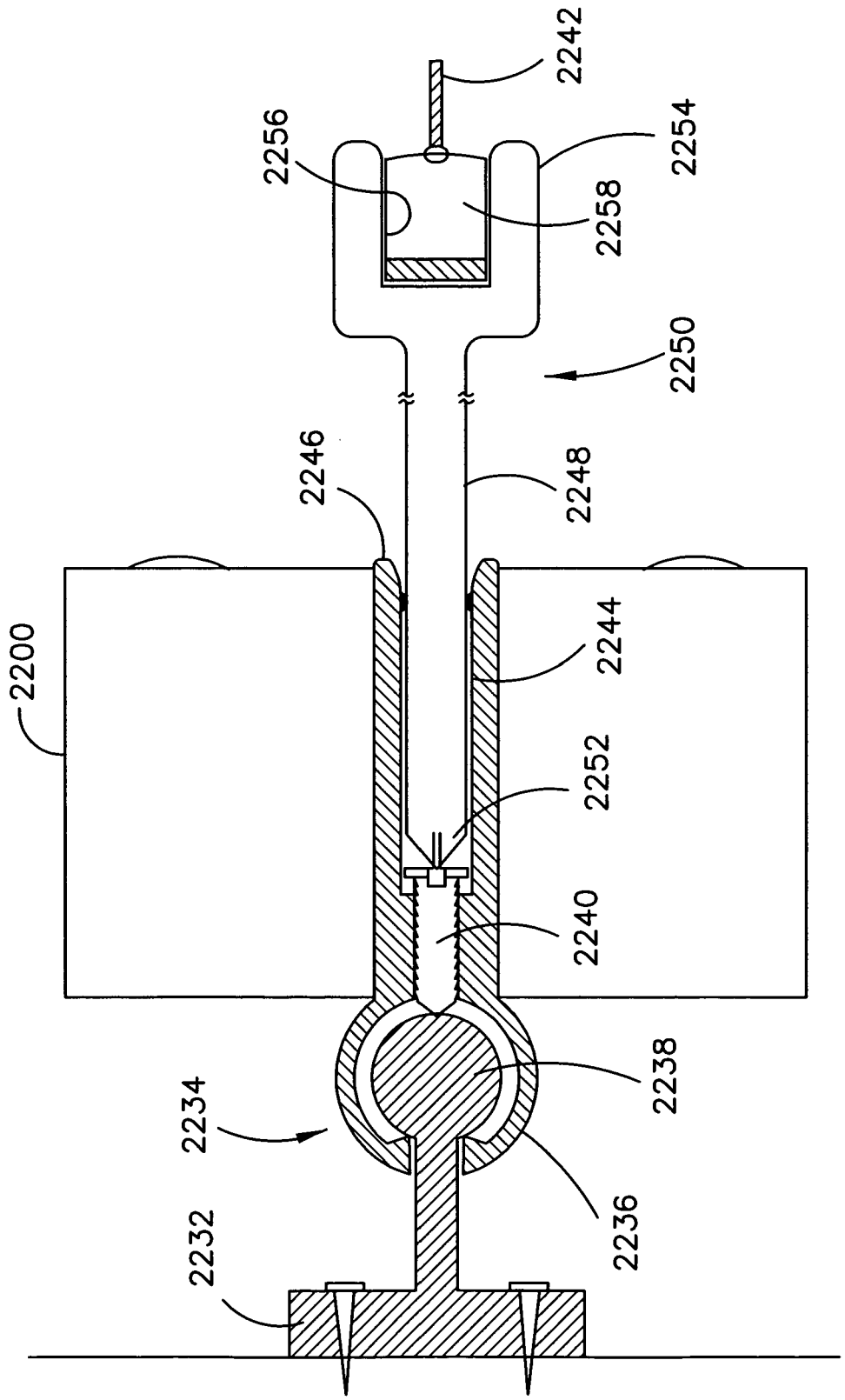
FIG. 19 shows a side view of another embodiment of smoke detector apparatus according to the invention.

FIG. 19 of the drawings depicts a manner of securing the smoke detector 2200 in a selected operable position. In this embodiment, the grubscrew 2240 used for locking the ball 2238 within the cup 2236 is accessible along a passage 2244 extending through to the front side 2246 of the detector housing 2200. The passage 2244 is configured to receive the shaft 2248 of an alignment tool 2250. The alignment tool 2250 has a driver 2252 on one end thereof and a handle 2254 on the other end thereof. The handle 2254 has a recess 2256 in the rear end thereof into which a laser 2258 has been inserted. The shaft 2248 is a close sliding fit with the passage 2244 such as when the shaft is located in the passage 2244 the laser beam 2242 from the laser 2258 is axially aligned with the light source 2202 and/or receiver 2204, as discussed above.

In this embodiment the shaft 2248 and the passage 2244 each have a complementary cylindrical shape. Of course the person skilled in the art will appreciate that other arrangements are possible, for example passage 2244 may have a square profile, the side dimension of the square corresponding to the diameter of the shaft 2248.

The installer, using the tool 2250 depicted in FIG. 19, will thus insert the shaft 2248 into the passage 2244 and then manipulate the housing 2200 whilst observing the visible alignment beam 2242 at a remote target. When the housing is correctly aligned, the handle 2254 will be rotated with driver head 2252 engaged with the grubscrew 2240 to thereby tighten the grubscrew 2240 and lock the cup and ball together. Once locked together in this way, the technician installing the equipment will check that the laser beam 2242 which is still correctly aligned with the target, and if so, will know that the smoke detector is correctly orientated. Clearly, at any time in the future, such as whenever the equipment is to be maintained or serviced, the orientation of the unit can be checked by simply inserting the shaft of the tool 2250 into the passage 2244 and checking, once again, whether the laser beam 2242 is correctly aligned with the target on the remote location.

In this embodiment, the driver 2252 is shown as a screw driver head, but clearly if the grubscrew has some other form of engagement formation, such as an Allen key socket, then the driver 2252 will be in the appropriately sized six sided Allen key configuration.

Whilst FIG. 19 depicts a tool having a laser installed therein for alignment purposes, it will, of course, be possible simply to insert a laser 2258 into the passage 2244 to assist with alignment of the housing relative to the remote target.

FIGS. 17 to 19 depict an arrangement in which the beam is aligned parallel to the incident light beam but this is not the only possible arrangement. For example, the housing may have a plurality of laser receiving sockets therein angled to the incident beam in a configuration which assists in the set up and orientation of the smoke detector relative to a remote target or area of interest. For example, where the smoke detector is of the form discussed above with reference to FIG. 3, then it may be desirable to have a laser beam which also indicates the full arc 2622 of the light source illumination. Clearly it would be possible to include a socket in the housing 2200 at an angle to the incident beam which will correspond to the full arc of the light source illumination.

Figure 20:
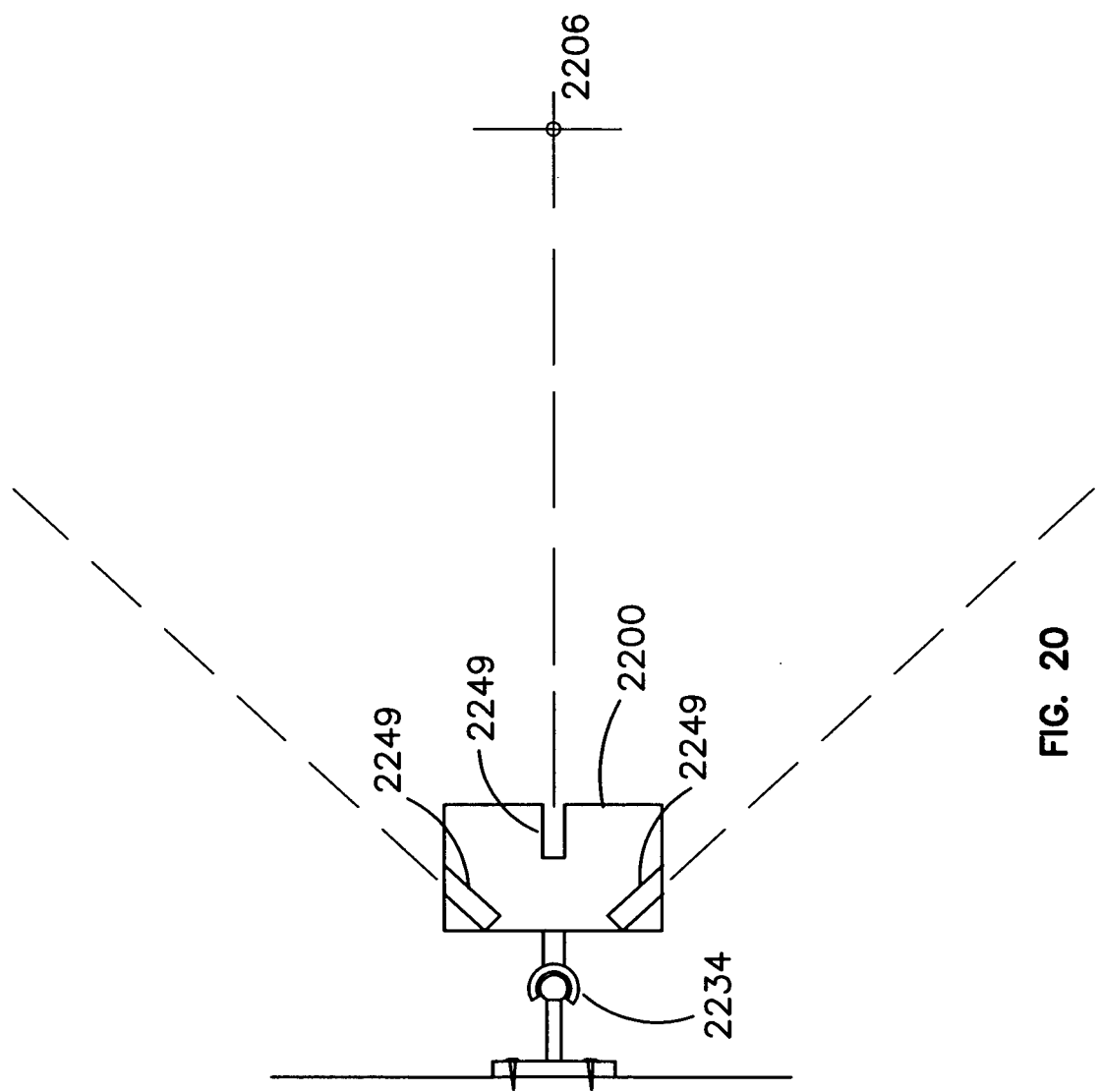
FIG. 20 shows a plan view of another embodiment of smoke detector apparatus according to the invention.

FIG. 20 depicts diagrammatically a housing having three sockets 2249, each of which is adapted to receive a tool 2250 shown in FIG. 19 so as to enable the installation technician to correctly align the housing for optimal performance. The lateral two sockets 2249 are preferably aligned relative to the arc of visible light which the video camera is able to detect, and the central socket will be used to align the centre of the video camera with the target 2206 at the remote location.

Figure 21:
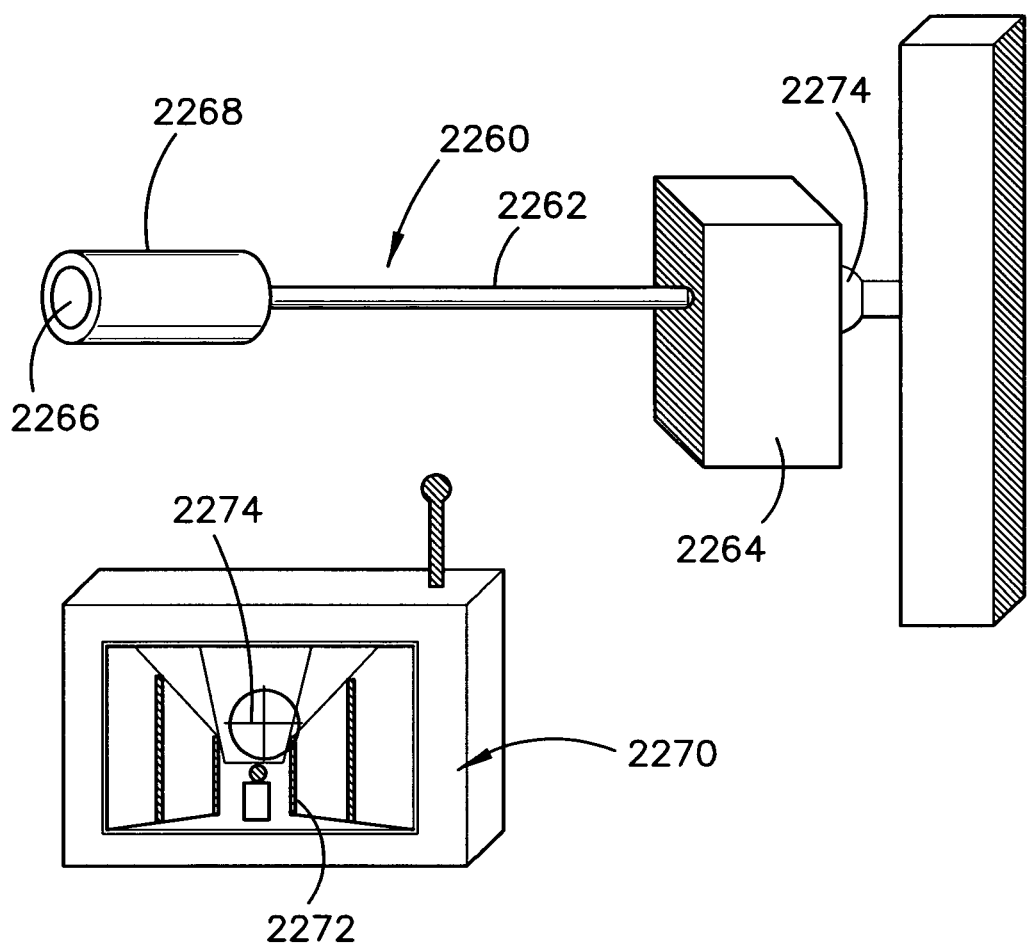
FIG. 21 shows a diagrammatic illustration of a further embodiment of smoke detector apparatus according to the invention.

FIG. 21 depicts a further embodiment of the invention. In this embodiment the visual alignment device 2260 includes a shaft 2262 which in turn is mounted in a socket of the smoke detector housing 2264 and will be aligned in fixed orientation to the optical components mounted in the housing 2264. A video camera 2266 is mounted in a handle portion 2268 at the end of the shaft 2262. The video camera will preferably be battery powered, and is adapted to generate an image of a target at a location remote from the housing 2264. The video camera is preferably provided with a telescopic lens.

The image viewed by the video camera is preferably transmitted wirelessly to a receiver unit 2270 which includes a screen 2272 on which the image of the remote target is displayed. The image may also include a sighting symbol or device 2274 which may be in the form of cross-hairs, or some other form of alignment assisting sighting device, such as a grid pattern or the like.

Clearly, when the housing is moved the field of view of the video camera and hence image generated via the video camera will move on the screen, and the technician doing the alignment of the smoke detector will be able to correctly orientate the housing by viewing the image on the screen. Since the video camera is aligned in a fixed relative alignment to the optical components of the smoke detector, once the image on the screen is correctly aligned with the intended target, the technician will know that the optical components are correctly aligned. The receiver unit is preferably a hand held, battery powered computer device such as a PDA or the like, showing real time images from the camera. The connection between the camera and the receiver will preferably be wireless, but could also be via cable.

The camera may be fitted with a wavelength dependent light filter, at a wavelength that corresponds to a light source, such as a LED, or other active or passive light source, mounted at the target position. The target light source may flash, optionally at a specific rate or pattern, so as to be readily discernable to the human eye. The pattern of flash may also be identified by software in the camera and/or the receiver.

The software in the receiver unit and or the camera may include means for generating an enhanced view of the target on the display, and may include surrounding images of the room or surface on which the target is mounted. The receiver unit and camera combination preferably includes means for generating audible sound cues and/or voice instructions to the operator to assist in the alignment process. These instructions may be in the nature of instructions on how to move the housing so as to correctly align with the target, and could include audible words such as 'up', 'down', 'left', 'right', 'on target', and the like.

It will be appreciated that, with the video camera mounted at the end of the shaft 2262, a small movement of the housing about articulated connection 2274 will move the video camera at the end of the shaft through a relatively wide arc. The shaft thus acts as a lever arm, with the video camera mounted on the distal end of the arm. This increases the sensitivity of the alignment process, so that, provided the video camera and optical components are in the correct relative alignment, when the video camera is correctly aligned with the target the optical components will be precisely aligned in the intended orientation.

Figure 22:
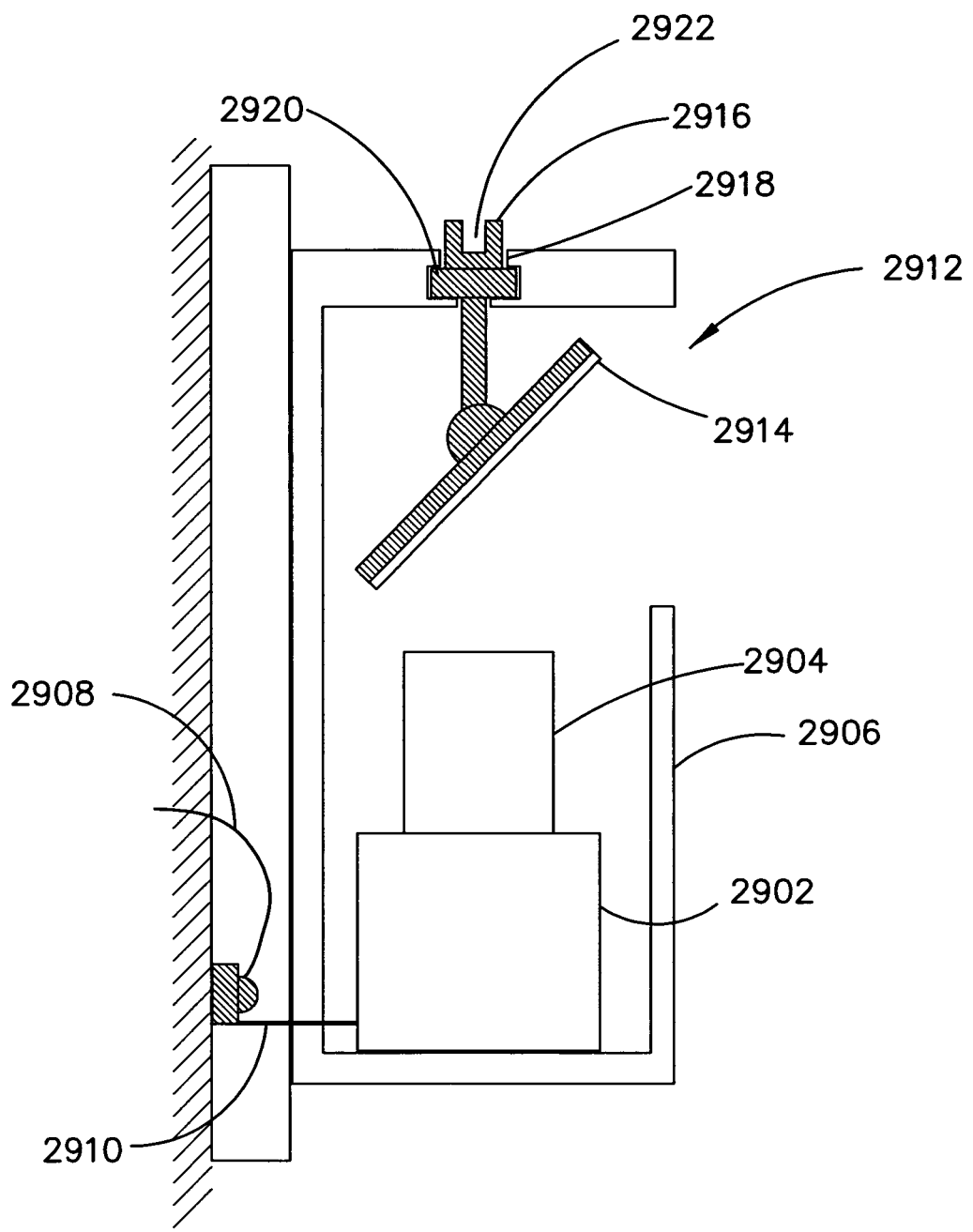
FIG. 22 shows a cross sectional view through a component of a smoke detector made in accordance with an alternative embodiment of the present invention.

FIG. 22 shows an alternative housing configuration for optical components made in accordance with an embodiment of the present invention.

In this example the component 2900 includes an electro-optical component, such as a camera or light source(s) and its associated electronic circuitry and optics 2904. The electro-optical component 2902 is mounted in a fixed relationship with respect to the housing 2906 and is connected via fixed wiring 2908 to electrical and data connections 2910.

The housing 2906 includes an aperture 2912 through which a beam of light may enter or exit the housing. The aperture 2912 may be open or can be closed by a lens or window. The component 2900 also includes an optical assembly 2914 mounted to the housing 2906. The optical assembly, in this case, is a mirror mounted at an angle with respect to the optical axis of the electro-optical system 2902, 2904. The mirror is used to redirect an optical signal either to or from the electro-optical system 2902, 2904 and through the aperture 2912.

The mirror 2914 is mounted to the housing 2906 via an articulated mounting means 2916. The articulated mounting means in this case comprises a rotatable shaft mounted in a rotation friction bearing 2918 which is captured in a corresponding shaped recess 2920 in the housing 2906. The articulated mounting 916 includes an engagement means 2922 which can be engaged from the outside of the housing 2906 using an alignment tool. For example, an alignment tool described in relation to the previous embodiments can be used.

In use, a technician installing the optical component uses the fixed mounting means to attach the housing in a fixed manner with respect to a mounting surface and then adjusts the external field of view (or illumination) of the electro-optical components 2902 by adjusting the orientation of the mirror 2914 using an alignment tool. The method of operation of the system is substantially the same as that described above except that the articulated connection enables the orientation of the optical assembly 2914 to be changed with respect to the electro-optical component which is mounted in a fixed relationship with the mounting surface, rather than enabling realignment of the entire housing with respect to the mounting surface.

Figure 23:
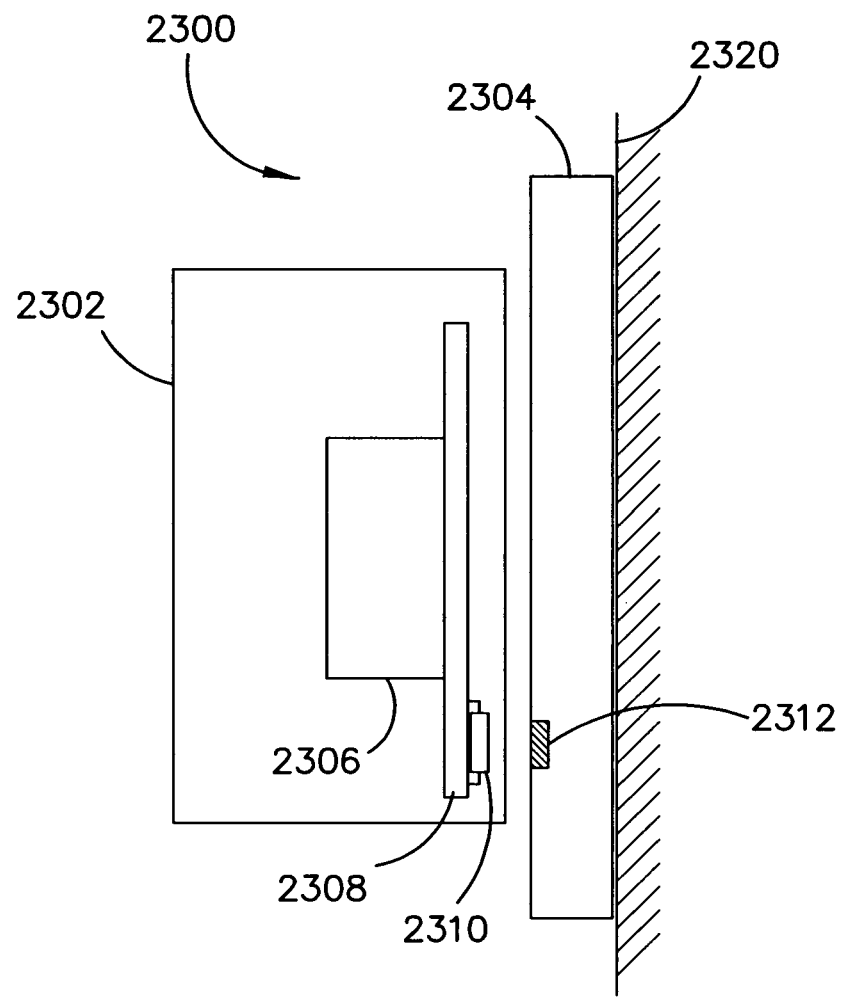
FIG. 23 is a schematic diagram of a beam-detector assembly having a first module and a second module, the assembly being powered up when the two modules are assembled.

FIG. 23 illustrates a beam-detector assembly 2300 which may, for example, be a light transmitter. The assembly 2300 is constructed in two modules. Module 2302 is a main enclosure housing a battery (not illustrated) and the electro-optical system 2306 for the unit. The electro-optical system 2306 may be mounted on a circuit board 2308. Module 2302 also includes a switch 2310 that, in one arrangement, is responsive to magnetic fields. An example of such a switch is a reed switch, which has of a pair of contacts on ferrous metal reeds positioned in a hermetically sealed glass envelope. The contacts are initially separated. In the presence of a magnetic field the switch closes. Once the magnetic field is removed, the stiffness of the reeds causes the contacts to separate.

Other switching devices that are sensitive to magnetic fields, such as Hall-effect devices may also be used.

Module 2304 is a mounting base, which includes an actuator capable of acting on the switch 2310. The actuator may, for example, be a magnet 2312.

The modules 2302 and 2304 are transported and stored separately from one another or in a package where the actuator is separated from the switch by sufficient distance to prevent activation of the switch. Typically, at installation, the module 2304 is affixed to a wall 2320 or mounting surface and the module 2302 is then attached to module 2304. It will be appreciated that there are many arrangements that enable module 2302 to be easily and securely mounted to module 2304. For example, module 2304 may have one or more tracks and, during assembly, the module 2302 may be slid along the tracks as far as a stopper. A detent means may be provided to hold the two modules in position. Such arrangements allow the two modules to be assembled in a predetermined orientation, thus positioning the switch 2310 relative to the magnet 2312.

Only when the modules 2302 and 2304 are assembled is the switch 2301 closed, permitting significant power consumption from the battery to begin.

In another arrangement, module 2304 includes a plurality of magnets 2312. The configuration of magnets 2312 may be used to represent an item of information, such as identifying data for the module 2304. The information may include a serial number or a loop address associated with the location of the module 2304. By providing a pattern of magnets on the base module 2304, the data may effectively be retained permanently at the location where module 2304 is attached to the wall 2320. Thus, even if the module 2302 is replaced, for example after a fault such as a depleted battery, the identifying data is still present.

The module 2302 may include a plurality of switches 2310 or sensors sensitive to the presence of the magnets 2312 in module 2304. For example, an array or predetermined pattern of reed switches may be provided, capable of reading the identification data coded in the pattern of magnets in module 2304.

In a further arrangement, the pattern of magnets 2312 in module 2304 may be provided on a removable device, such as a card. The card with the pattern of magnets may, for example, be inserted into the module 2304 when the module is affixed to the wall 2320.

Figure 24:
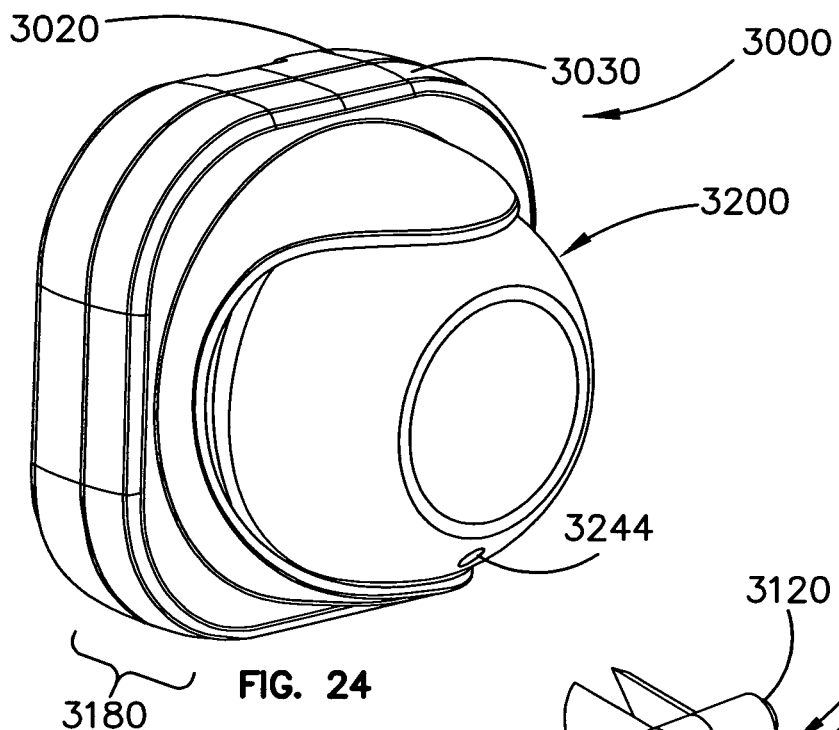
FIG. 24 is a perspective view of a transmitter, in accordance with an embodiment of the present invention.
Figure 25:
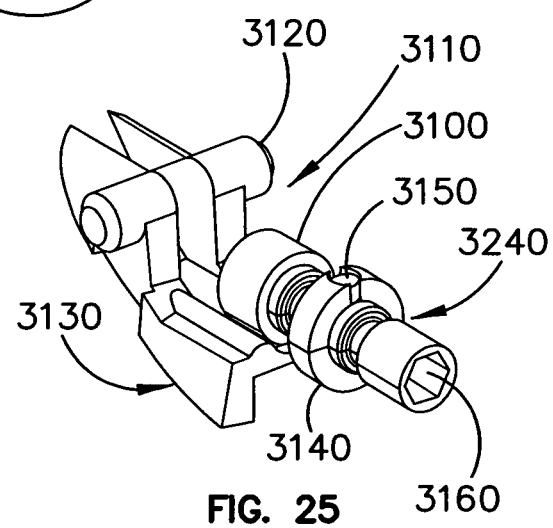
FIG. 25 is a close up perspective view of the brake shoe and spindle of the transmitter of FIG. 24.
Figure 26:
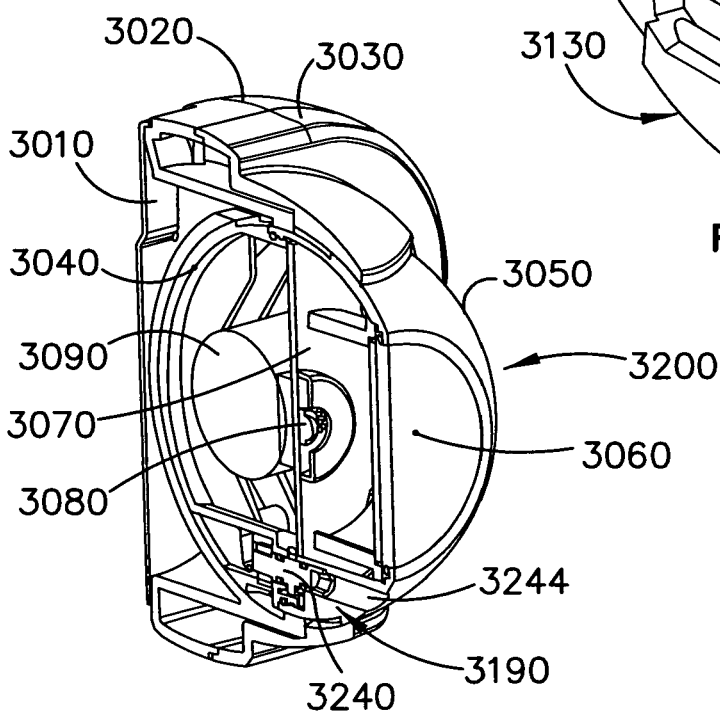
FIG. 26 is a perspective cutaway view of the receiver of FIG. 24.

FIGS. 24 to 26 illustrate an alternative embodiment of the invention. The transmitter unit 3000 includes a housing 3200, forming an optical module. The transmitter further includes a backing plate 3010, rear casing 3020 and forward casing 3030 which together form a mounting portion 3180.

The backing plate 3010 includes screw holes through which it may be mounted to a mounting surface (not shown) such as a wall. The backing plate 3010 is attached to the rear casing 3020 with a simple, releasable, snap fit.

The rear casing 3020 and forward casing 3030 together define a partial spherical cavity in which the housing 3200 is received. The housing 3200 includes a rear housing 3040 and a forward housing 3050. Each of the rear and forward housing 3040, 3050 has a predominantly hollow hemispherical shell like form.

The rear housing 3040 has a lip about its outer periphery. The forward housing 3050 a complementary lip on the interior of its outer periphery. The complementary lips are snap fitted together to define the spherical housing 3200. Adjacent this snap fit a small portion of the rear housing 3040 projects into the forward housing 3050 and defines an annular step thereabouts.

The outer surface of detector housing 3200 is predominantly spherical and complementary to the spherical cavity defined by the rear casing 3020 and the forward casing 3030. There is a close sliding fit between the complementary spherical surfaces so that the housing 3020 may be rotated to a wide range of orientations relative to the mounting portion 3180 and loosely frictionally held in alignment during installation.

A forward end of the forward casing 3030 is open to expose the housing 3200. In this embodiment the opening in the forward casing 3030 is shaped, and curved, to allow the housing 3200 to be articulated to a wider range of angles about a vertical axis than about a horizontal axis: typically such transmitters are wall mounted close to the ceiling, as are the corresponding receivers, it follows that generally less adjustment is required about a horizontal axis, i.e. in the up and down direction.

A forward end of the forward housing 3050 is truncated to define a circular opening in which a lens 3060 is carried. A circular printed circuit board (PCB) 3070 is centrally mounted within and spans the housing 3200. The PCB 3070 is parallel to the lens 3060 and seats against the annular step defined by the rear housing 3040 projecting into the forward housing 3050.

A light source in the form of LED 3080 is centrally mounted on a forward surface of the PCB 3070 and in use projects a beam of light e.g. in one or more wavelength bands, the obscuration of which provides an indication of the presence of particles. The lens 3060 is arranged to collimate the beam projected by the LED 3080. A battery 3090 is carried on a rear face of the PCB 3070.

The illustrated embodiment includes a locking mechanism 3190 including a spindle 3240, a cam 3100 and a brake shoe 3110 illustrated in FIG. 25. The spindle 3240 has at its axial mid point an outwardly projecting collar 3140.

Each of the rear housing 3040 and the forward housing 3050 include a tubular recess for receiving a respective portion of the spindle 3240. The collar 3140 is captured between the rear housing 3040 and the forward housing 3050 when the rear and forward housings are snap fitted together. O-ring seals around the spindle fore and aft of the collar 3040 limit the ingress of debris into the housing 3200 via the tubular recesses.

A hexagonal socket 3160 is formed in a forward end face of the spindle 3240. A cylindrical tubular passageway 3244 passes through the forward housing 3050 and provides access to the socket 3160. The socket 3160 during installation of the transmitter unit receives an Allen key like fitting from the front of the transmitter unit 3000 via the passage 3244 so that an installer may rotate the spindle 3240 about its axis. As will be described, said rotation locks the housing 3200 in a selected orientation relative to the mounting portion 3180.

The rear housing 3040 has a rearward aperture in which is carried a brake shoe 3110. The brake shoe 3110 has an outer surface 3130 which is part spherical and aligned with the spherical outer surface of the rear housing 3040 when in a retracted 'articulating position'. The brake shoe 3110 carries a stud 3120 on each of its sides. The studs 3120 project a short sideways distance, i.e. in directions perpendicular to the up and down and fore and aft directions. The studs 3120 are received within complementary recesses (not shown) in the rear housing 3040 and thereby define a pivot about which the brake shoe 3110 may rotate through a range of motion. The range of motion is limited by contact between the braking surface 3130 and the internal spherical surface defined by rear and/or forward casings 3020, 3030, and by contact with a cam 3100 described below.

As illustrated in FIG. 25 the brake shoe 3110 includes a central longitudinal channel separating two wing portions which each carry a respective stud 3120. The brake shoe 3110 has a degree of compliance so that the brake shoe 3110 and the rear casing 3040 may be assembled by compressing the wing portions, to reduce the overall dimension across the studs 3120, and fitting the brake shoe 3110 to the rear casing 3040 so that the studs 3120 are received into the complementary recesses (not shown) formed in the rear casing 3040. Once released the wing portions return to their uncompressed shape so that the studs 3120 snap into the complementary recesses.

Figure 28:
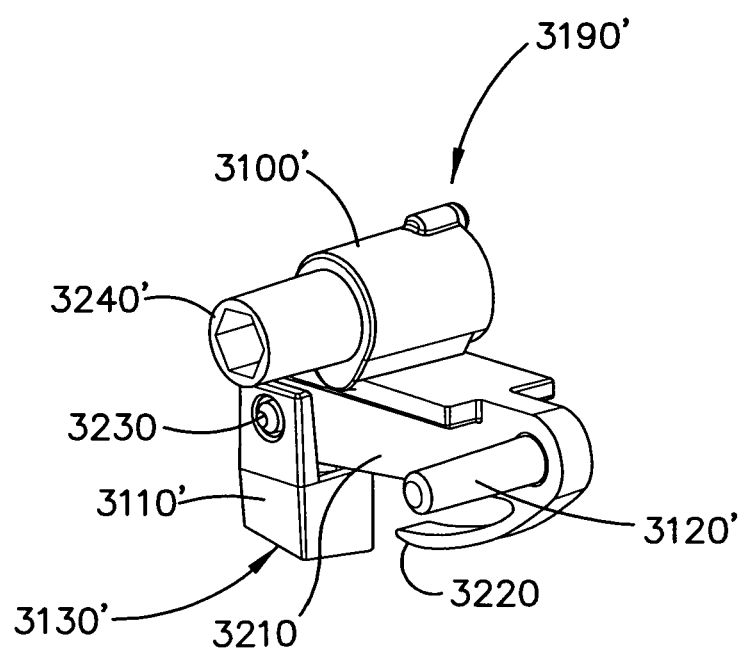
FIG. 28 is a close up perspective view of the brake shoe, lever arm and spindle of the transmitter of FIG. 27.

The cam 3100 is carried by the spindle 3240. Of course another option would be for the cam to be integrally formed with the spindle as illustrated in FIG. 28. The cam 3100 includes a single lobe and is arranged to act downwardly on the brake shoe 3110 at a location forwardly spaced from the studs 3120 (and a pivot axis defined thereby).

During installation of the receiver 3000, after aligning the housing 3200, an installer accesses socket 3160 of spindle 3240 via the passage 3244 with an Allen key like tool. Using the Allen key like tool to rotate the spindle 3240 rotates the cam 3100, which in turn drives the forward portions of the brake shoe 3110 downwardly so that the braking surface 3130 frictionally engages the internal spherical surface defined by rear and forward casings 3020 and 3030. The alignment of the housing 3200 relative to the mounting portion 3180 is thereby locked.

In this embodiment the lens 3060 and LED 3080 are configured to project light in a direction perpendicular to the plane of the lens 3060. The passageway 3244 is also perpendicular to the plane of the lens 3060. During installation an alignment tool, similar to those described above, may be used, wherein the alignment tool has a cylindrical shaft sized for a close sliding fit with the passage 3244 and includes a laser pointer arranged to project a beam coaxial with the shaft. In this embodiment the shaft of the alignment tool terminates in an Allen key fitting complementary to the socket 3160. During installation the tool is inserted into the passage 3244 and engaged with the socket 3160. When engaged, the alignment tool can be used as a lever and may be manipulated until its projected beam is focused on a target, such as a receiver. The passage 3244 thereby provides a convenient means for providing a visual indication of the alignment of the housing 3200. The alignment tool may then be simply rotated about its axis to lock the housing 3200 in the correct alignment.

As previously described, it is desirable that the power supply, in this case the battery 3090, is only connected (to activate the transmitter) upon installation. The collar 3140 of spindle 3240 carries at a point on its circumference a magnet 3150. The relative position of the magnet 3150 and the lobe of the cam 3100 is selected so that when the brake shoe 3110 is in an advanced, 'braking', position the magnet 3150 interacts with a reed switch (not shown) mounted on a rear face of the PCB 3070 to close the switch and thereby connect the power supply and activate the receiver 3000. The location of the magnet about the collar 3140 relative to the lobe of the cam 3100 is selected so that when the brake shoe 3110 is in the retracted, 'articulation', position the magnet 3150 does not act on the reed switch, so that the reed switch remains open, and the receiver remains inactive.

The transmitter unit 3000 is simple to install. The receiver 3000 can be supplied as a preassembled unit—with the locking mechanism in the retracted, articulation, position so that the battery is not connected and does not run down. The backing plate, which is attached to the rear casing 3020 with a simple snap fit is levered off (i.e. unsnapped) and screwed or otherwise fastened to a wall or other mounting surface. The rear casing 3020, and the remainder of the receiver 3000 attached thereto, is then simply snapped onto the backing plate. The housing is then aligned using the aforedescribed alignment tool and then easily and conveniently locked in said alignment and activated with a single motion of the same tool.

Figure 27:
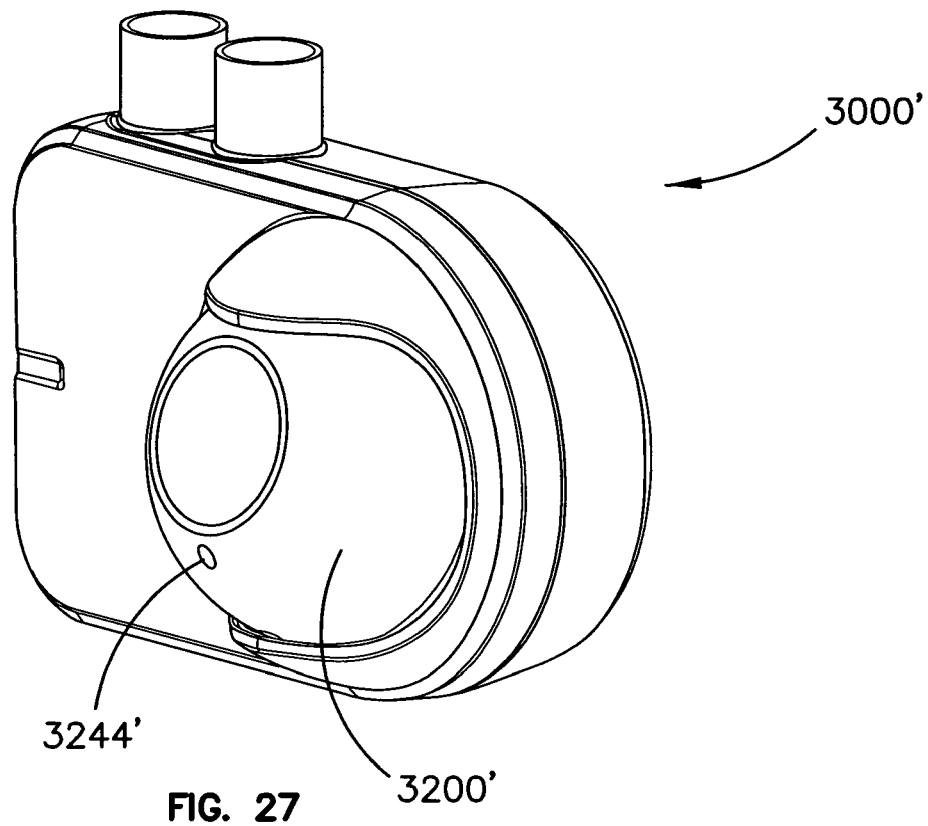
FIG. 27 is a perspective view of a receiver in accordance with an embodiment of the present invention.

FIGS. 27 and 28 illustrate a further alternative embodiment of the invention similar to the embodiment described in FIGS. 24 to 26. FIG. 28 is analogous to FIG. 25 however it illustrates a receiver 3000' useable in an embodiment of the present invention. Receiver 3000' includes a passage 3244' through which a spindle 3240' may be accessed as in the previous embodiment. This embodiment differs from the embodiment of FIG. 24 in the details of the locking mechanism. The spindle 3240' includes an integrally formed cam 3100' arranged to act on a pivotally mounted lever arm 3210.

The lever arm 3210 has a length in the sideways direction, i.e. perpendicular to the up and down and fore and aft directions. A stud at 3120' projects forwardly from one end of the lever arm 3210. The stud 3120' is received within a complementary recess (not shown) defined within the transmitter housing 3200' at which the lever arm 3210 is pivotally supported within the transmitter housing 3200'.

Short studs 3230 project in the fore and aft directions from the other end of the lever arm 3210. The studs 3230 are coaxially aligned. A brake shoe 3110' including an upwardly projecting clevis arrangement embraces the other end of the lever arm and engages with the studs 3230 to pivotally connect the lever arm 3210 and brake shoe 3110'. The brake shoe 3110' projects downwardly from the lever arm 3210, and has a square cross section and determinates in a part spherical braking surface 3130'.

The brake shoe 3110' is seated within and guided by a tubular through hole (not shown), having a complementary square profile, within the transmitter housing 3200'.

During installation of the transmitter 3000' the spindle 3240' is rotated, as in the previous embodiment. As the spindle 3240' is rotated the cam 3100' acts to drive the lever arm 3210 downwardly about its pivot axis (defined by the stud 3120'). The braking shoe 3110' is in turn pushed downwardly to frictionally engage an internal surface of the fixed mounting portion 3180'.

The lever arm 3210 includes an integrally formed finger 3220 projecting downwardly, from the end of the lever arm 3210, at an acute angle from a main body of the arm. The finger 3220 defines a curved path an outer surface of which is complementary to an interior of the transmitter housing 3200'. The finger 3220 is dimensioned to press against said interior and thereby bias the lever arm 3210 to rotate upwardly about its pivot axis (defined by the stud 3120'). The brake shoe 3110' is thereby biased against the cam towards a retracted, non-braking, position.

Figure 29:
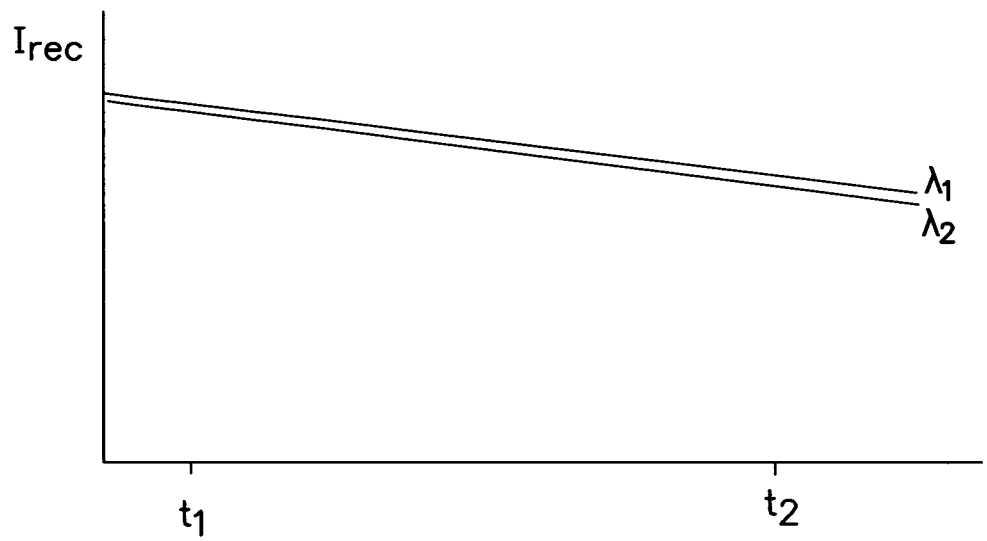
FIG. 29 illustrates a plot of received light at two wavelengths in a beam detector according to an embodiment of the present invention.

As noted previously the soiling of optical surfaces over time can cause problems in beam detectors. To address this problem the inventors have determined that the system can be adapted to compensate for soiling of the optical system over time. FIG. 29 illustrates how the true received light level i.e. the level of light arriving at the system's receiver or light sensor decreases over time. FIG. 29 shows a plot between times t1 and t2 of the true light level arriving at a sensor of a beam detector receiver over time. As can be seen from the plots the received light level at wavelengths $\lambda_1$ and $\lambda_2$ decrease gradually over time due to the build up of contamination on the surfaces of the optical system of the receiver. To compensate for the loss of sensitivity, in one embodiment of the present invention, the system gain is correspondingly increased very slowly over time (as indicated in FIG. 30) such that the detected intensity $\lambda_1$ and $\lambda_2$ remains substantially stable over time.

Figure 30:
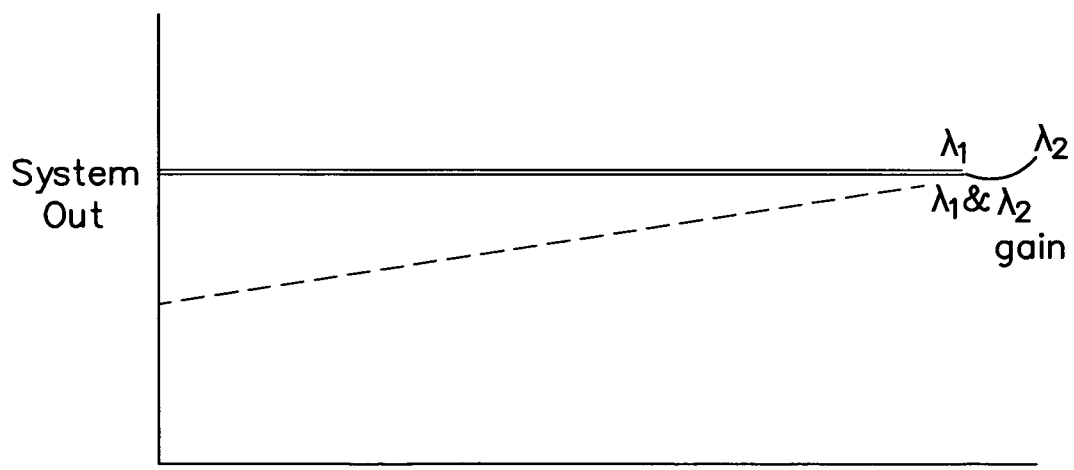
FIG. 30 shows a plot of the gain and corrected output when implementing a method according to an embodiment of the present invention.
Figure 31:
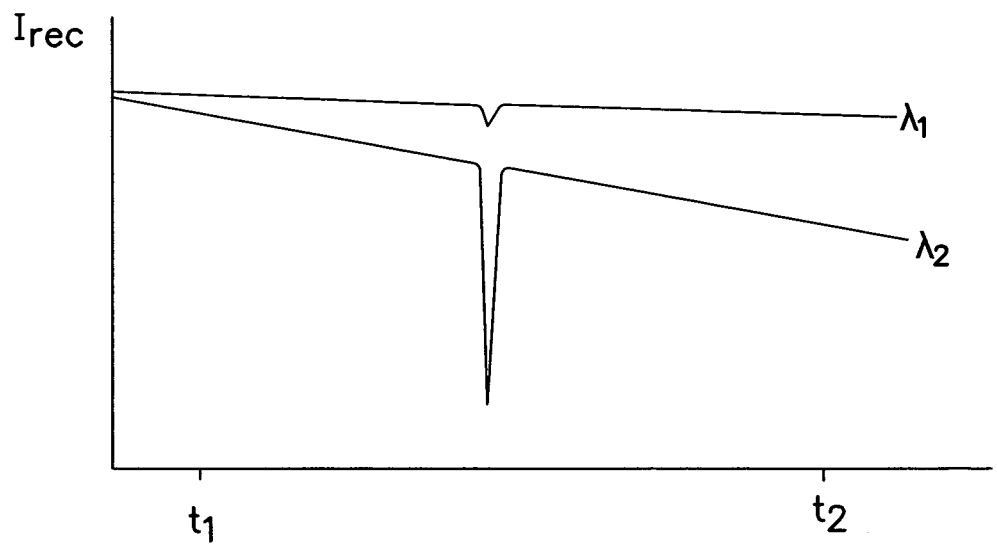
FIG. 31 shows the received light level in two wavelength bands in an embodiment of the present invention.

FIG. 31 is similar to that of FIG. 30 except, as can be seen the degradation in performance in wavelength bands $\lambda_1$ and $\lambda_2$ are different. In this embodiment, the signal at $\lambda_2$ is more greatly influenced by the contamination of the optics than that at $\lambda_1$. In such a scenario, a system which uses a differential, or relative value between the received signals in two wavelength bands as likely to go into a false alarm state as the separation between the received signal at wavelength $\lambda_1$ and $\lambda_2$ increases. To address this problem, the gain is adjusted differently for each wavelength, and as can be seen when the gains are adjusted, as in FIG. 30 the long term average output of the system remains substantially constant.

Figure 32:
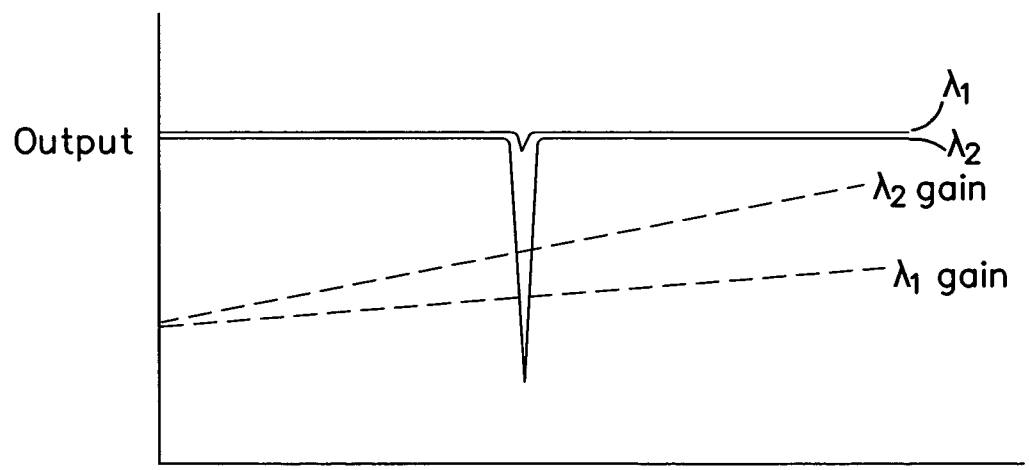
FIG. 32 shows the corrected output level and adjusted gain levels when implementing methods according to an embodiment of the present invention in the conditions described in FIG. 31.

In the examples of FIGS. 31 and 32 a smoke event 3500 occurs approximately midway between times t1 and t2. In this case, because $\lambda_1$ effectively operates as a reference wavelength it undergoes a very minor drop in intensity whereas the received signal at $\lambda_2$ undergoes a very marked drop due to $\lambda_2$'s tendency to be more strongly absorbed by small particles. As can be seen, because the smoke event has such a short duration in comparison to the compensation being applied to the gains the long term compensation for system contamination is not affected by the occurrence of the smoke event 3500 and the smoke event 3500 is also reliably detected by the system.

Figure 33:
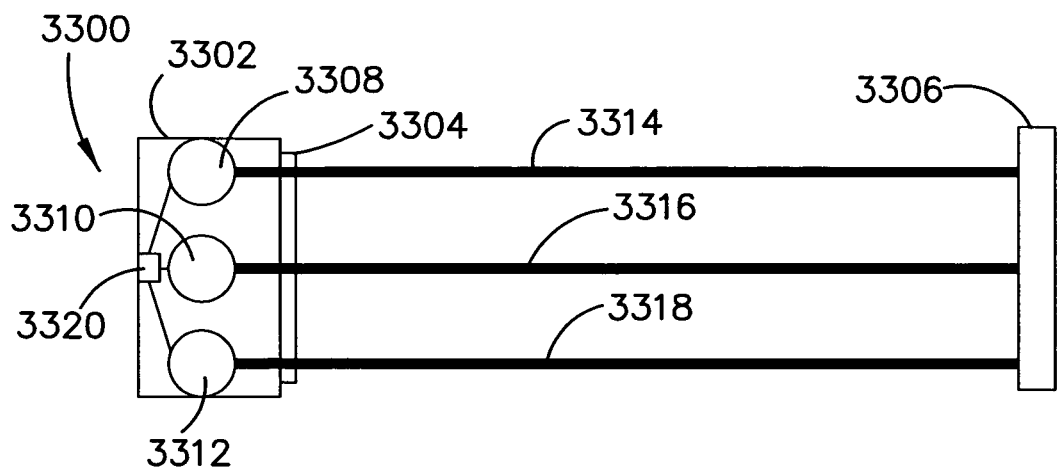
FIG. 33 illustrates a particle detection system incorporating a light source in accordance with an embodiment of the invention.
Figure 34:
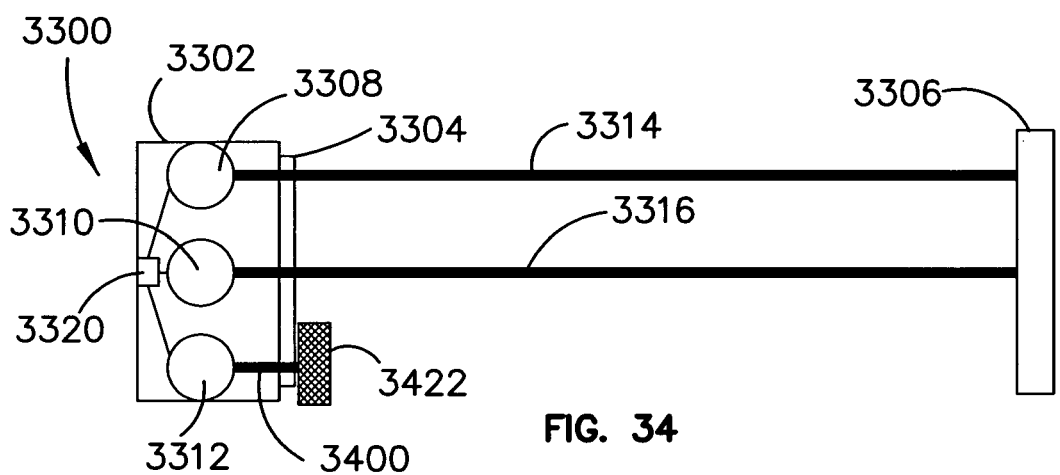
FIG. 34 illustrates the light source of FIG. 33 when partially obstructed by a foreign body.
Figure 35:
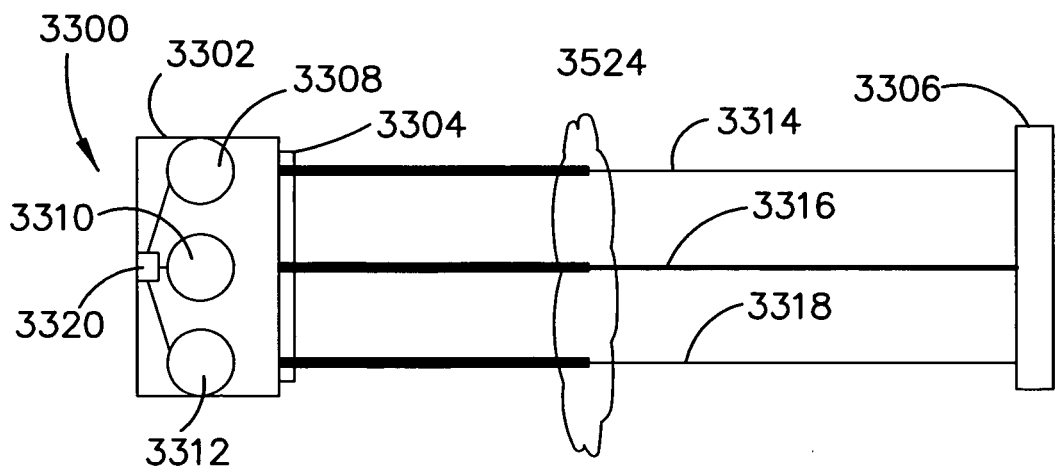
FIG. 35 illustrates the light source of FIG. 33 when obstructed by smoke.

Referring to FIGS. 33 to 35, a light source 3300 according to an embodiment of the present invention is depicted. The light source 3300 includes a housing 3302 with a transmission zone 3304 through which light is transmitted from the light source 3300 to a receiver 3306.

The transmission zone 3304 is in this instance located on the exterior of the housing 3302 and provides the point at which light from within the housing 3302 is transmitted from the light source 3300 towards the receiver 3306. As such, the transmission zone 3304 is accessible from outside the light source 3300 and may be affected by dust/dirt build up, insect/bug activity etc. The transmission zone 3304 may, without limitation, be any optical surface (or part thereof), and while for illustration purposes has been depicted as protruding from the housing 3302 it may, of course, be flush with or recessed within the walls of the housing 3302. The transmission zone 3304 may be integral with the housing 3302 or may be a component part thereof.

In the present embodiment the housing 3302 houses a first light emitter 3308, a second light emitter 3310 and a third light emitter 3312. Each light emitter 3308 to 3312 is an LED and emits a beam of light (3314, 3316 and 3318 respectively) which is transmitted through the transmission zone 3304 to the receiver 3306. The first light emitter 3308 and third light emitter 3312 emit electromagnetic radiation in a first spectral band, e.g. UV light (i.e. light in the ultraviolet portion of the EM spectrum) of substantially equal wavelength, and as such shall be referred to as UV emitters. The second light emitter 3310 emits EM radiation in a second spectral band, e.g. IR light (i.e. in the infrared portion of the EM spectrum) and as such shall be referred to as a IR emitter. Correspondingly, light beams 3314 and 3318 will be referred to UV light beams and light beam 3316 will be referred to as a IR light beam.

The light source 3300 also includes a controller 3320 adapted to control operation of the first, second and third light emitters 3308 to 3312. The controller may be housed within the housing 3302 as shown, or may be remote from the housing and control operation of the light emitters 3308 to 3312 remotely.

As will be appreciated, the specific manner in which the light emitters 3308 to 3312 are operated by the controller 3320 depends on the programming of the system. In this embodiment the controller 3320 alternates operation of the light emitters 3308 to 3312 in a repeating alternating sequence. The processing of these beams as received by the receiver 3306 is discussed in further detail below.

The controller may also be adapted to operate one or more of the light emitters 3308 to 3312 to send a control signal to the receiver 3306. Such a control signal may indicate status information regarding the light source 3300, for example, convey that the light source 3300 is operational, that the light source 3300 is malfunctioning, and/or that the light source 3300 battery is running out. The control signal may be determined by the timing and/or intensity of the light beams 3314, 3316 and/or 3318 as emitted by respective light emitter 3308 to 3312.

As can be seen, the UV light emitters 3308 and 3312 are separated from each other which, in turn, leads to a separation of the point at which the UV light beams 3314 and 3318 leave the transmission zone 3304. The separation between the UV light emitters (and UV light beams 3314 and 3318) is of sufficient distance such that if the transmission zone 3304 is obstructed by a foreign body 3322 only one of the UV light beams 3314 or 3318 may be obstructed. A separation of approximately 50 mm between the first and third light beams 3314 and 3318 has been found suitable for this purpose. Thus, this arrangement effectively provides a redundant light emitter in the UV band.

The term "foreign body" is used here to refer to objects or nuisance particles larger than dust or smoke particles or other particles of interest that may be present in the air. As one example, a foreign body obstructing the transmission zone 3304 may be an insect or bug crawling over the transmission zone 3304.

FIG. 34 shows an example of a single UV light beam 3318 being obstructed, with the remaining IR light beam 3314 unobstructed. In this instance the receiver 3306 recognises a fault condition because it only received every second expected UV pulse rather than an alarm condition.

Should this condition (i.e. the condition where only one of the UV light beams 3314 or 3318 is being received at the receiver 3306 or is received at a significantly lower level than the other due to partial obstruction) persist for a significant time, e.g. 1 minute, the receiver 3306 may be programmed to interpret this as an error/malfunction with the light source 3300 and trigger an appropriate alarm/error message.

In contrast to the obstruction shown in FIG. 34, FIG. 35 depicts the situation where smoke particles 3324 in the air obstruct all three beams 3314 to 3318. In this instance the smoke 3324 attenuates each of the light beams 3314 and 3318 to substantially the same extent, and the usual alarm logic can be applied to determine whether an alarm or fault condition exists.

Figure 36:
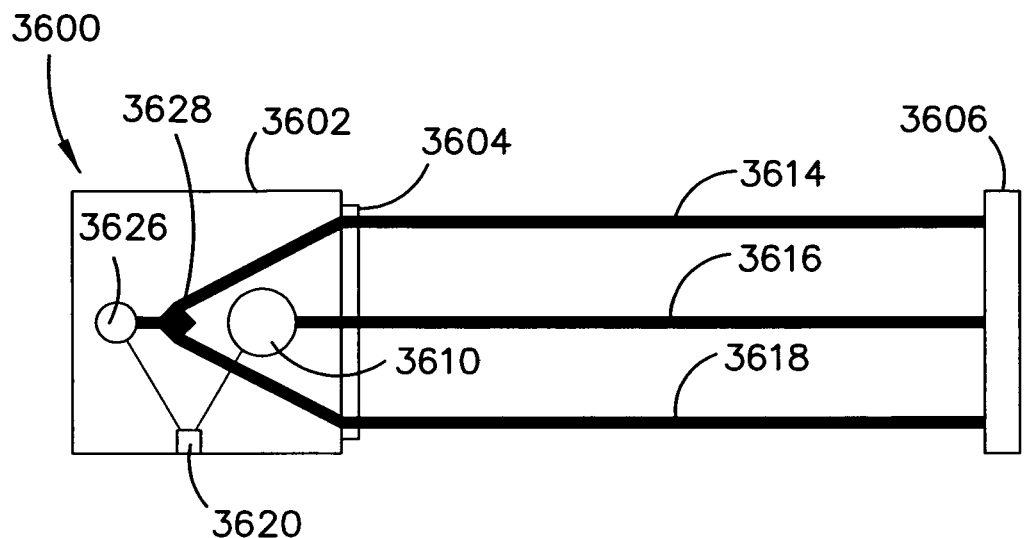
FIG. 36 illustrates an alternative embodiment of the light source depicted in FIGS. 33 to 35.

FIG. 36 provides an alternative to the above embodiment. The light source 3600, similarly to the previous embodiment includes a housing 3602 and a transmission zone (or window) 3604 through which beams 3614, 3616 and 3618 are emitted to a receiver 3606. The operation of the light source 3600 is controlled by a controller 3620. UV light beams 3614 and 3618 are emitted from a single UV light emitter 3626. In this case the light source 3600 includes a beam splitter 3628 which splits the beam from light source 3626 such that the first and third light beams 3614 and 3618 exit the transmission zone 3604 at a sufficient distance from each other as described above.

Turning to FIGS. 37 to 40, a further alternative embodiment of a light source 3700 for use in a particle detection system is provided. Light source 3700 includes a housing 3702 with a transmission zone 3704 through which light is transmitted from the light source 3700 to a receiver 3706. The transmission zone 3704 is as described above in relation to transmission zone 3604, however as can be seen is much smaller.

Housing 3702 houses first and second LED light emitters 3708 and 3710. Light emitter 3708 is a UV light emitter and emits a UV light beam 3712, while light emitter 3710 is an IR light emitter and emits IR light beam 3714. The light source 3700 also includes a controller 3716 adapted to control operation of the first and second light emitters 3708 and 3710. The controller may be housed within the housing 3702 as shown, or may be remote from the housing and control operation of the light emitters 3708 and 3710 remotely.

As can be seen, the light source 3700 is configured (as described below) such that the light beams 3712 and 3714 leave the light source from the transmission zone 3704 along substantially the same path. Most preferably they are co-linear. This arrangement provides the feature that if the transmission zone 3704 is obstructed by a foreign body 3718 as shown in FIG. 38 (again, for example, an insect crawling across the transmission zone) the UV and IR light beams 3712 and 3714 are obstructed to a substantially equivalent degree.

When a foreign body 3718 obstructs the transmission zone 3704 it causes substantially equal obstruction to both the first and second beams 3712 and 3714, and the controller associated with the receiver will apply alarm and or fault logic to determine the cause of the decreased received light level. The fault and alarm logic can be configured to interpret an equivalent and simultaneous drop in received intensity in the following manner. In some cases with a small drop in intensity the system may interpret this as a fault or obstruction. If the condition persists it can be compensated for in software or a fault condition raised. With a large drop in intensity an alarm may be raised, even though the primary alarm criteria are based on differential attenuation of the two wavelength bands as described in our co-pending patent application.

Figure 37:
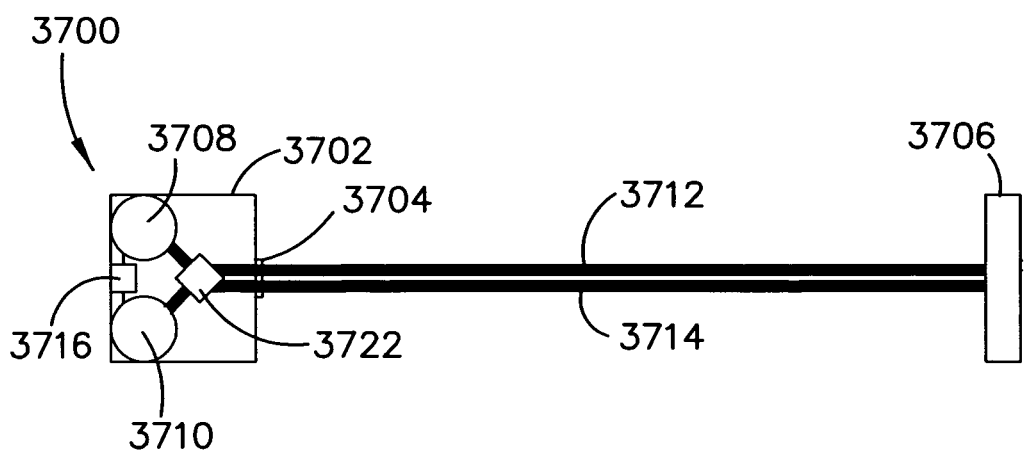
FIG. 37 illustrates a particle detection system incorporating a light source in accordance with an alternative embodiment of the invention.
Figure 38:
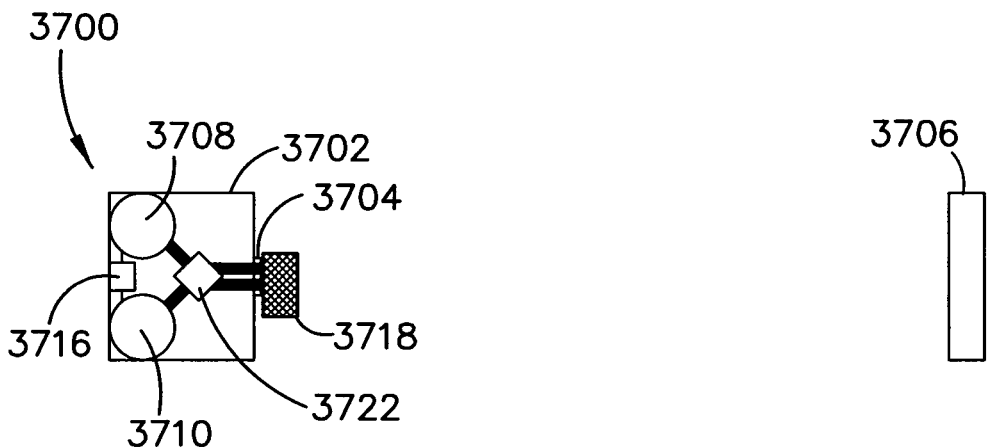
FIG. 38 illustrates the light source of FIG. 37 when partially obstructed by a foreign body.

FIGS. 37 and 38 provide one embodiment of a light source 3700 configured to provide beams 3712 and 3714 that leave the light source 3726 from the transmission zone 3704 along substantially co-linear paths. In this embodiment light beams 3712 and 3714 do not originate from light sources 3708 and 3710 that are physically proximate, but are brought into proximity with each other prior to reaching the transmission zone with light directing optics 3722. Light directing optics 3722 may be any optics suitable for directing light, such as mirrors, lenses (e.g. convex, concave, Fresnel lenses) and/or prisms, or a combination thereof, and may also serve to collimate light beams 3712 and 3714.

Figure 39:
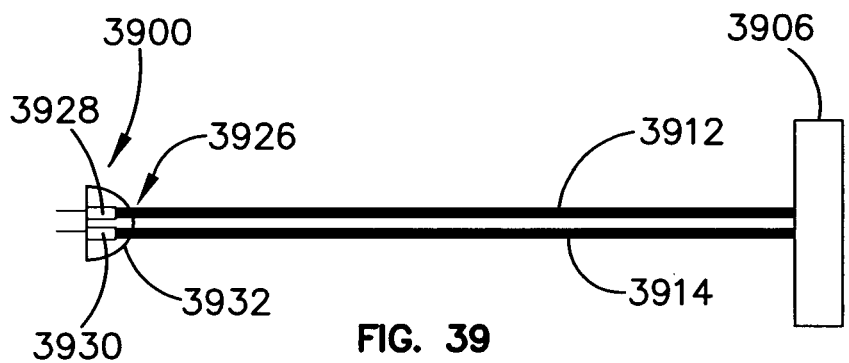
FIG. 39 illustrates an alternative embodiment of the light source depicted in FIGS. 37 and 38.

FIG. 39 provides an alternative embodiment of a light emitter 3724 configured such that the light beams 3712 and 3714 leave the light source from the transmission zone 3726 close together. In this embodiment the first and second light emitters 3728 and 3730 are semiconductor dies housed within a single optical package 3732 (the transmission zone 3726 being the point at which the emitted light beams 3712 and 3714 exit the package 3732). In this embodiment the proximity of light beams 3712 and 3714 is achieved by the physical proximity of the semiconductor dies 3728 and 3730 within the package 3732 and the leasing effect of the package 3732.

Figure 47:
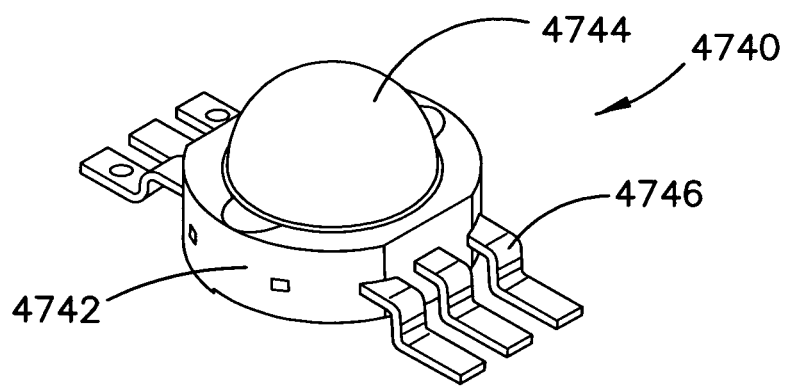
FIG. 47 illustrates a light emitter usable in a first embodiment of the present invention.
Figure 48:
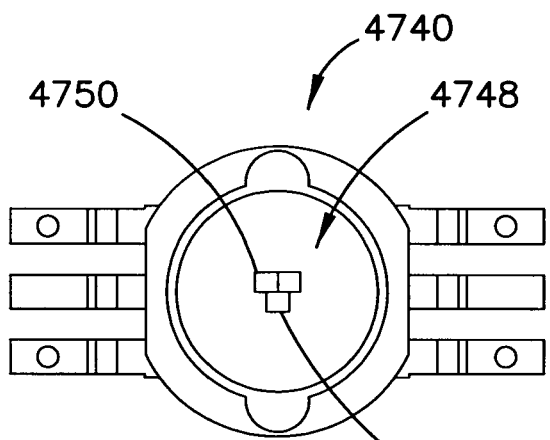
FIG. 48 illustrates further detail of light emitter usable in an embodiment of the present invention.
Figure 49:
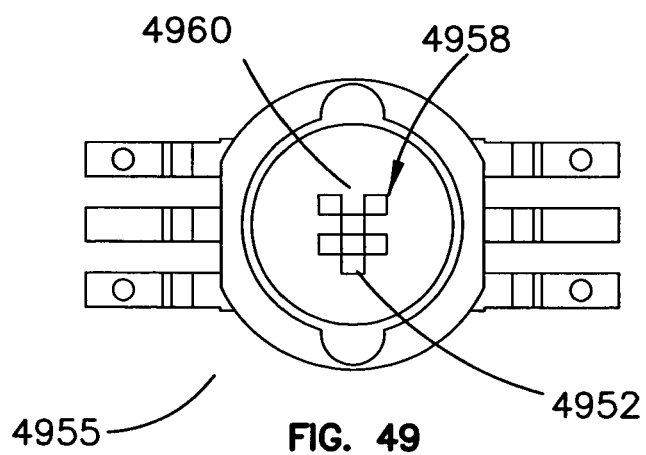
FIG. 49 illustrates a further embodiment of a light emitter usable in an embodiment of the present invention.

This may be achieved by using an LED with multiple semiconductor dies in a common LED package. Examples are depicted in FIGS. 47 to 49. As with typical LED's, the housing is made of a clear material and shaped so as to have a lens effect on the emitted light beams that broadly constrains the beams to a forward direction.

Figure 41:
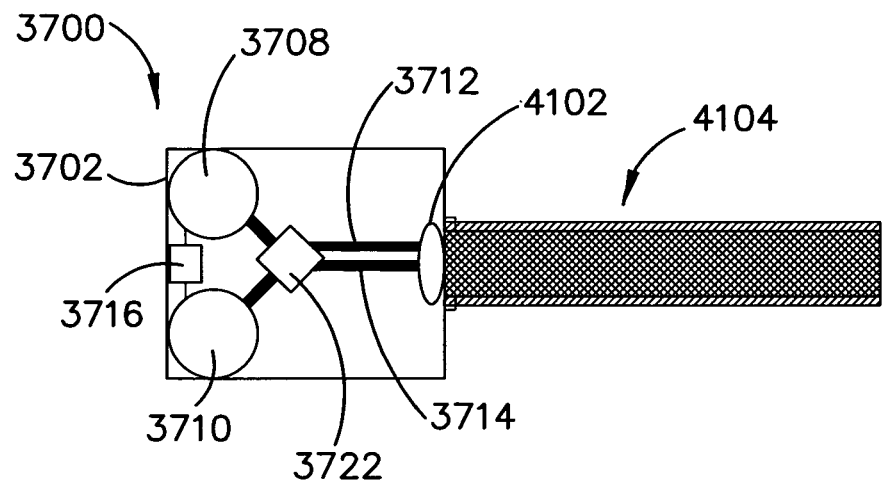
FIGS. 41 and 42 illustrate light sources in accordance with further embodiments of the invention.
Figure 42:
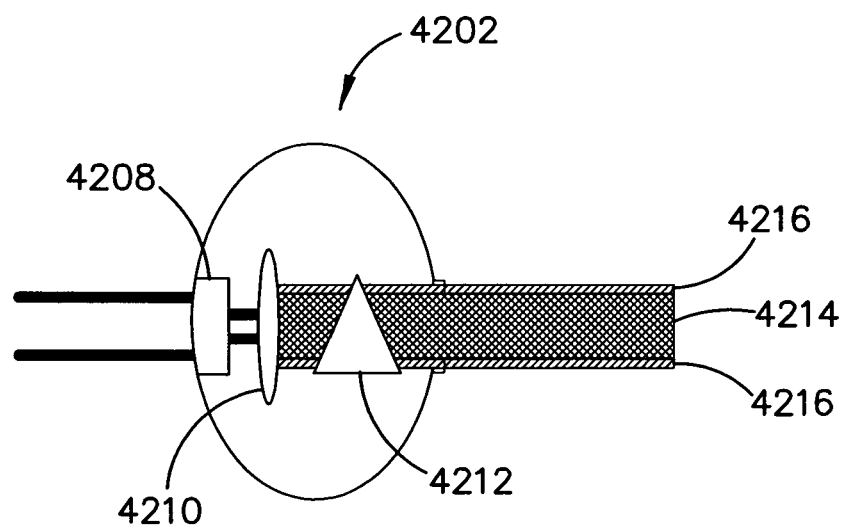

In a further embodiment, and as shown in FIGS. 41 and 42, the light source 3700 is also provided with beam shaping optics 4102 for adjusting the shape of light beams emitted from light emitters 3708 and 3710. Whilst depicted as a single element in FIG. 41, the beam shaping optics 4102 may in practice (and as shown in FIG. 42) include a number of beam adjusting elements serving variously to adjust the beam width and/or beam shape of light transmitted from the light source 3700 to the receiver 3706.

Light beams 3712 and 3714 (from light emitters 3708 and 3710) pass through the beam shaping optics 4202 which function to provide an adjusted beam 4104 with desired characteristics as discussed below.

As will be appreciated a beam will have a spatial intensity profile, or beam profile, in a direction transverse to its axis. Using the beam profile a beam width of a light beam can be defined between two points of equivalent intensity e.g. between the 3 db points either side of a maxima etc. One common measurement of beam width is the "full width at half maximum" (FWHM) of the beam. For example, the adjusted beam 4204 in FIG. 42 is shown as having a wide section 4214 in which the intensity of the beam 4204 is above the predetermined threshold (depicted in black) fringed by lighter beam sections 4216 where the intensity of the beam is below the predetermined threshold.

The beam shaping optics 4102 can be chosen to achieve a desired beam profile, and a collimating element 4208 serving to collimate light beams 3712 and 3714 into a tighter beam shape. The collimating element 4208 may, for example, be a lens such as a Fresnel lens or a convex lens, or may be a reflector.

The beam adjusting optics can also include a diffusing element 4210, selected to "flatten" the beam profile and increase the beam width of the light beams 3712 and 3714. The diffusing element can be for example a ground/etched/smoked glass diffuser. The diffusing element 4210 may, alternatively, be a coating applied to either the transmission zone 3704 or another beam adjusting element.

Figure 40:
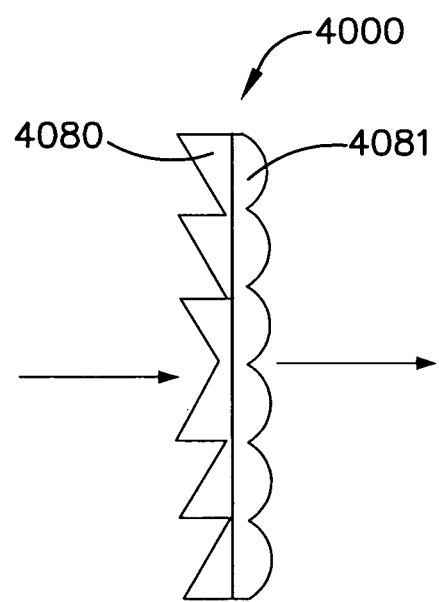
FIG. 40 illustrates an optical subsystem usable in an embodiment of the present invention.

FIG. 40 illustrates an exemplary optical element 4000 that shapes and flattens the beam profile. The optical element 4000 includes a Fresnel lens 4080 placed back to back with a multi-element lens 4081. The Fresnel lens collimates the beam and the multi-element lens 4081 effectively diffuses the beam. In place of the multi-element lens 4081 another diffuser eg. ground, smoked or etched glass or surface could be used.

Providing a diffuser on the transmitter is advantageous as the receiver will "see" an extended spot corresponding to the light source, rather than a point, which would be observed without the diffuser. Consequently, any foreign body (such as an insect) landing on the transmission zone 3702 will cover a smaller proportion of the transmission zone and therefore have a proportionally smaller effect on the total light received at the receiver 3706. Moreover, in a multiple beam system when all light emitters (3708 and 3710, i.e. light at both the UV and IR wavelength) are diffused through a common element any foreign body (such as an insect) landing on the transmission zone 3702 will effect each wavelength of the light (i.e. UV and IR) by substantially the same amount.

Figure 43:
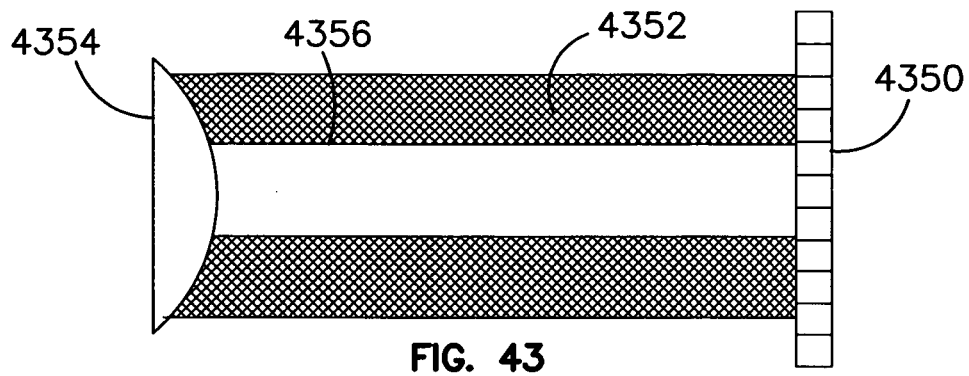
FIGS. 43 and 44 illustrate the effect of modifying the beam width of a light source used in a particle detection system.

Further by providing a greater beam width to the adjusted beam 4204 alignment of the receiver 3706 with the light source 3700 is simplified. FIG. 43 provides a depiction of a receiver 4350 receiving a beam 4352 from a light source 4354. By having a wide beam width the rate of change of intensity across the beam width (near its centre) is reduced. This means that as alignment of the beam and receiver drift over time, the rate of change in received intensity near the centre of the beam, for small relative movements, is reduced compared to a beam with a narrow beam width.

Figure 44:
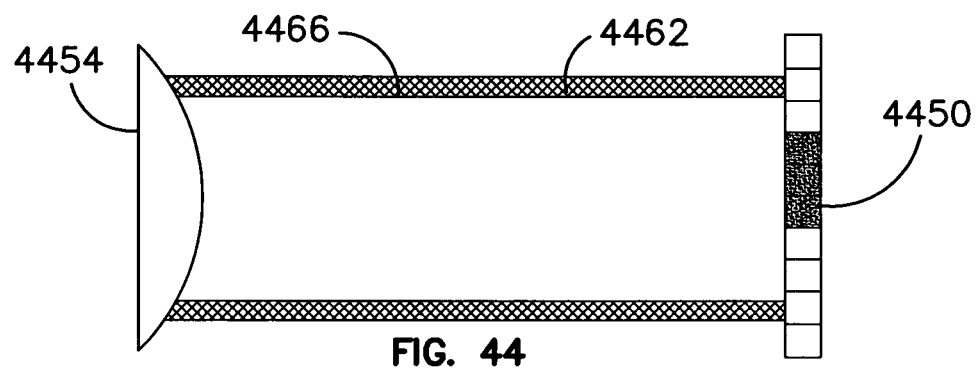

In this case the beam width 4356 of the beam 4352 corresponds to about three sensor elements on the sensor 4350. If the system is configured to average (or aggregate) output these three pixels are used to determine the received beam's strength, a small variation in alignment between the transmitter and received will require either the system to accurately track the beam movement on the sensor's surface or alternatively cause a large variation in measured signal strength from the three pixels. This problem's minimised using a wider beam width as shown in FIG. 44. In this system the beam 4462 emitted by the light surface 4454 has a width 4456 equal to about the size of 6 sensor elements on sensor 4450. As will be appreciated such a system is more tolerant to alignment drift before the central 3 pixels lie outside the central high intensity beam region.

The specific properties of the diffuser used and the beam width provided will depend on the receiver and light emitters. Using LED's, however a beam width of approximately 10 degrees has been found to be a suitable compromise between the preservation of intensity of the adjusted beam and width, so as to accommodate for easy alignment of the receiver with the light source and drift of the receiver and/or light source.

Referring to FIG. 42, the profile adjusting element 4212 is selected such that the beam profile of the adjusted beam 4204 extends further in the horizontal direction than the vertical. This serves to maximise the intensity of the adjusted beam 4204 at the receiver whilst also accommodating for the fact that building movement typically introduces more variation in the horizontal plane than the vertical plane.

The light source can include a wavelength dependent profile adjusting element 4212 for providing a different intensity profile to beams in different wavelength bands. The beam adjustment element may again be a lens, reflector, coating or similar selected to provide the desired beam profile at each wavelength is achieved.

Figure 45:
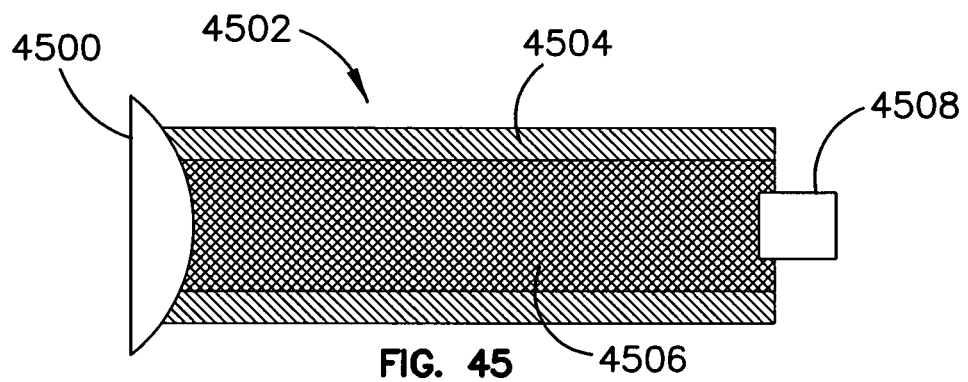
FIGS. 45 and 46 illustrate an advantage of having different spatial profiles for light in different wavelength bands of emitted light used in a particle detection system.
Figure 46:
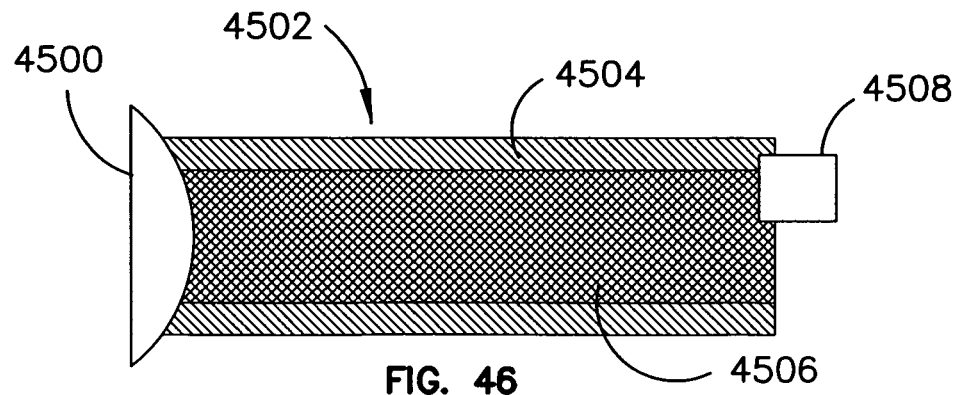

The profile adjusting element 4212 has the effect of producing an adjusted beam 4204 having a beam profile in which the beam width of the UV light (originating from the UV emitter 3708) is wider than the beam width of IR light (originating from the IR emitter 3710). This is depicted in FIGS. 45 and 46 where the light source 4500 transmits a beam 4502 in which the beam width of the UV light 4504 is wider than the beam width of the IR light 4506. This has the advantage that in the event that the light source 4500 or receiver 4508 moves (e.g. due to building movement) and the alignment therebetween is disrupted, the IR light 4506 (having a narrower beam width) will move out of alignment with the receiver 4508 (i.e.

reducing the amount of IR light received at the receiver) before the UV light 4504 does. This produces a decrease in IR light intensity at the receiver, followed by a decrease in UV intensity as alignment become progressively worse. This is the opposite to the effect seen when smoke enters the beam, when UV drops before IR. Hence the misalignment can be distinguished from a smoke event by the fault/alarm logic of the controller.

As an alternative to using a profile adjusting element, a light source may be used with a plurality of UV light emitters surrounding one or more IR light emitters. In this case as the alignment of the light source and receiver is disrupted the receiver will cease to receive IR light before it ceases to receive the UV light beam, thereby allowing the receiver to interpret this as a fault rather than an alarm event.

In some embodiments an exotic intensity profile can be formed, e.g. an intensity profile having a sinc function or similar. In this case if a sensor element or group of sensor elements of the receiver's sensor detects a variation in received beam intensity that matches the spatial intensity profile of the transmitted beam, it can be determined by the controller that the beam is sweeping across the sensor element or group of sensor elements. This can be used by fault logic to detect and signal that the system is drifting out of alignment and either re-alignment is needed or soon will be needed.

FIG. 47 illustrates a light emitter 4740 which may be used in a transmitter of a beam detector according to an embodiment of the present invention. The light emitter 4740 includes a body 4742 in which is housed one or more light emitting elements (not shown). The emitter 4740 includes a lens or window portion 4744 through which the beams of light generated by the light emitting elements are emitted. It also includes a plurality of leads 4746 for making electrical connection to the device. FIG. 47 illustrates a plan view of the same light emitter 4740. The light emitter 4740 includes a plurality of light emitting elements 4748, 4750. In this case the light emitter is a LED and the light emitting elements are two LED dies in the form of a UV LED die 4748 and an IR LED die 4750 which constitute the light emitting elements. The package 4740 also includes a photodiode 4752 within the body 4742. Each of the light emitting elements 4748, 4750 are adapted to emit light through the lens 4744. The photodiode 4752 receives some proportion of the light emitted by the light emitting elements 4748, 4750 and generates an electrical signal which is fed to a feedback circuit. The photodiode output signal is used by the feedback circuit to adjust the output of the light emitting elements to maintain correct operation of the light emitter 4740.

FIG. 49 illustrates a second embodiment of a light source. In this example, the light emitter 4955 includes a plurality of light emitting elements arranged in a checkered pattern. In this case, the light emitter 4955 includes four UV LED dies 4958 arranged around a central IR LED die 4960. As described above, this arrangement may have particular advantages for preventing false alarms caused by a misalignment of the light source with its respective receiver. The package 4955 also includes a photo diode 4952.

Figure 50:
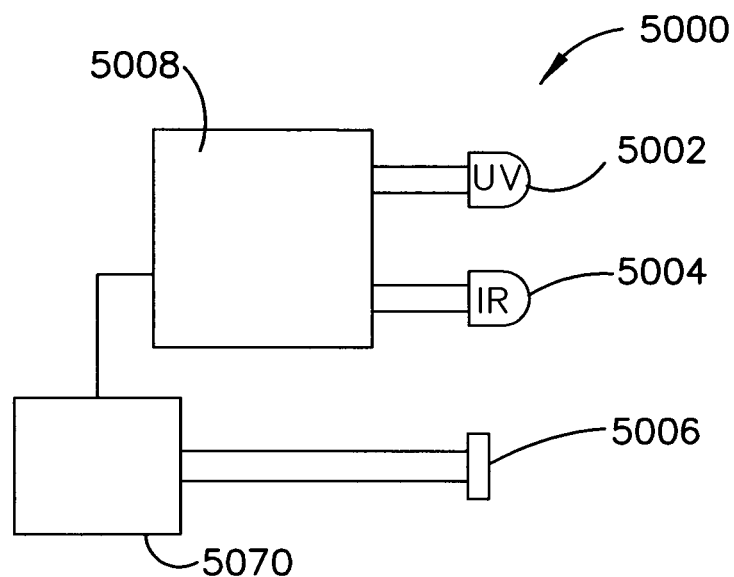
FIG. 50 is a schematic block diagram illustrating a circuit usable in an embodiment of the present invention.
Figure 51:
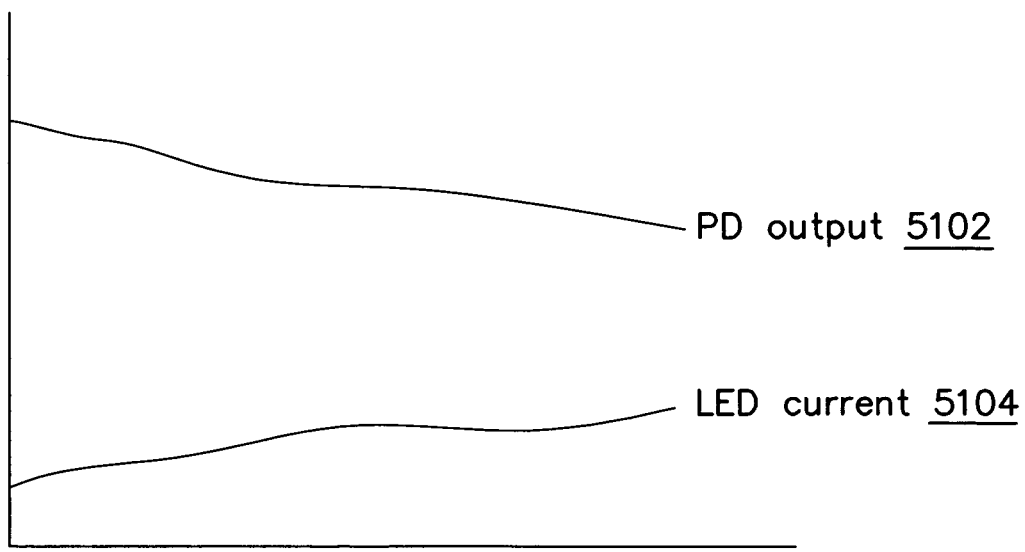
FIG. 51 is a plot illustrating the operation of the circuit of FIG. 50.

FIG. 50 illustrates a schematic block diagram of circuit for a transmitter which may be used in an embodiment of the present invention. The circuit 5000 includes two light emitters 5002, 5004 which e.g. correspond to the infrared and UV LED dies as described above. It also includes a photodiode 5006. As will be apparent from the above description the LEDs and photodiode 5002, 5004, 5006 may be packaged closely adjacent to each other within a single LED package. However, they may also be separately packaged in individual components. The light emitters 5002, 5004 are electrically connected to a current source 5008 and the photodiode 5006 is electrically connected to a feedback circuit 5010. The feedback circuit 5010 is in communication with the current source 5008. In use, the output from the photodiode 5006 which represents the output of LEDs 5002, 5004, is passed to the feedback circuit 5010 which in turn controls the output of the current source 5008 to the light emitters 5002, 5004. As the received light signal at the photodiode 5006 decreases, for example due to decreased light output by the LEDs over time or through decreased light emission of the light emitters 5002, 5004 due to an increase in temperature, the feedback circuit 5010 will apply an output to the current source 5008 which causes an increase in the drive current to the light sources 5002, 5004. In this way, the light output of the light emitters 5002, 5004 can be maintained at an approximately constant level. Because the light emitters may have different characteristics and predetermined illumination characteristics required for correct system operation, the output of the two light emitters 5002, 5004 can be individually controlled and adjusted. This can be achieved by alternatively pulsing their illumination and individually determining their light output using the photodiode 5006. Alternatively, multiple photodiodes could be used in a manner in which their response is wavelength selective, and tuned to a corresponding light emitter. For example this may be achieved by providing different bandpass filters over each of the photodiodes. In this case, the light emitters 5002, 5004 can be simultaneously illuminated and their outputs individually stabilised using a feedback circuit as described herein. FIG. 51 illustrates the feedback procedure of the circuit of FIG. 50 in stabilising the light output of one light emitter which is continuously illuminated. The plot of FIG. 51 includes a first portion 5102 which represents the output of the photodiode over time and represents a decrease in light output from the light source over time. This output is fed into the feedback circuit which controls the drive current output by the current source 5008. The decrease in the photodiode output causes an increase in the LED output current as shown by plot 5104.

Figure 52:
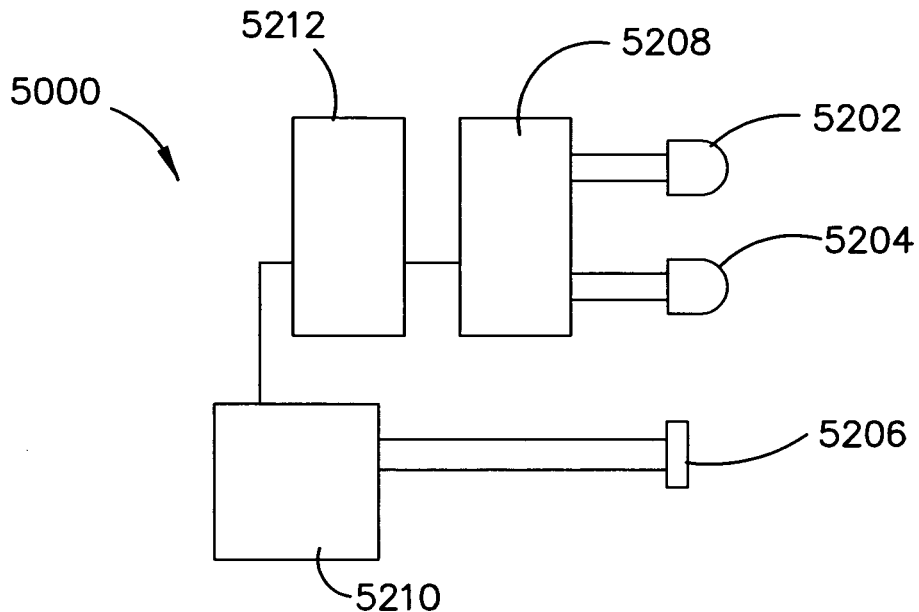
FIG. 52 is a schematic block diagram illustrating a second circuit usable in an embodiment of the present invention.

FIG. 52 illustrates a second circuit in a schematic block diagram form. In this example, rather than controlling the output current of the current source, the duration of output pulses of the light emitters is controlled by the feedback circuit. Accordingly, FIG. 51 includes two light sources 5202, 5204 each of which is connected to a current source 5208. The circuit also includes a photodiode 5206 which is connected to a feedback circuit 5210. This circuit 5200 additionally includes a drive pulse modulation circuit 5212 which controls the timing and duration of the pulses of current applied to the light emitters 5202, 5204 by the current source 5208. In this example, when a decrease in the received light level received by the photodiode 5206 is sensed the feedback circuit 5210 applies a signal to the modulation circuit 5212. In response, the modulation circuit 5212 increases the pulse length produced by the current source 5208 that is applied to the LEDs.

Figure 53:
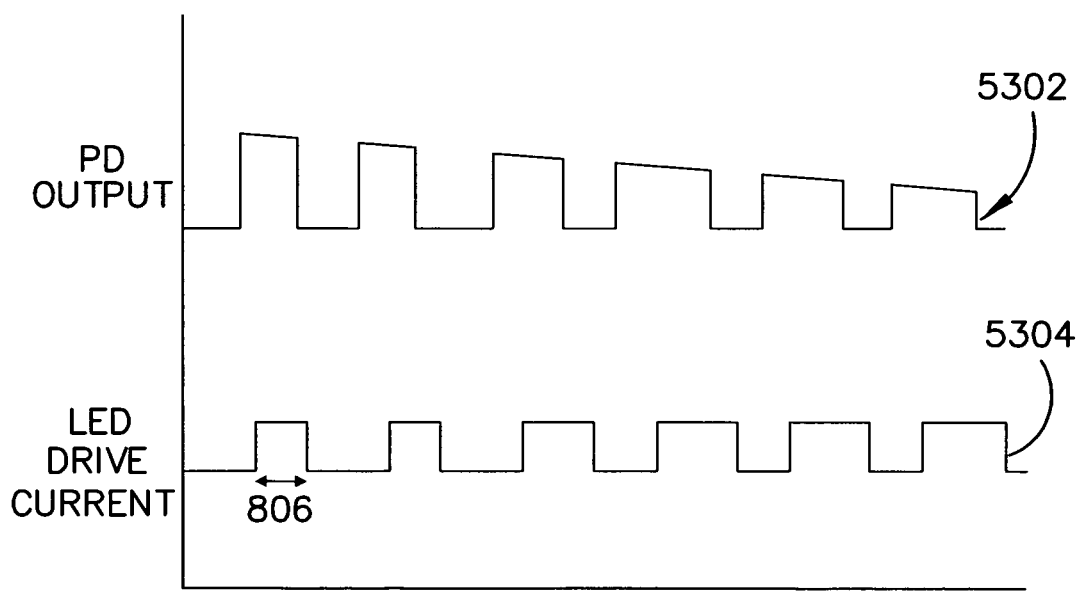
FIG. 53 is a plot illustrating the operation of the circuit of FIG. 52.

FIG. 53 illustrates the method of operation of the circuit of FIG. 52. The top plot illustrates the output of the photodiode 5302, which as can be seen, generally decreases over time. The lower plot 5304 illustrates the drive current applied to the light emitters. In this case, the output current is applied in square wave pulses e.g. 5306. As the output of the photodiode decreases the duration of the pulses increases over time. By adjusting the pulse duration in this manner and maintaining the current at a constant level the effective light intensity transmitted by the light emitters, when integrated over the pulse length remains substantially constant. Advantageously it also results in more accurate reception of the pulses at the receiver since rather than the receiver simply taking a single sample of the light intensity within each pulse the receiver can be operated as an integrator and collects more of the transmitted signal.

The plots of FIGS. 51 and 53 illustrate the photodiode response and drive circuit current for a single light emitting element of the transmitter. A similar plot can be created for the other (or others) light emitting elements.

In another embodiment of the present invention open loop control of the LED intensity may be provided. For example, this may be achieved at low cost by providing a current drive circuit that is temperature stabilised or temperature compensated for the output characteristics of the LED.

In a further embodiment of the present invention the output of the light emitting elements may only be weakly controlled, for example by being driven by a fixed pulse length with a very simple current control circuit. In this case, the averaged output intensity which is measured by the photodiode can be communicated to the receiver. The receiver can then be configured to compensate for the changing LED output in software. In a preferred form the averaged LED output can be communicated to the receiver using an optical communications channel or other wireless communications channel. In a case where an optical communications channel is used, this can be implemented by modulating the output of the light emitters themselves by inserting or omitting pulses in the sequence of illumination pulses of one or the other, or both of the light emitters. This embodiment has the advantage of requiring only a relatively low cost transmitter without complex feedback circuitry. It also takes advantage of the fact that temperature and age related drift of the light emitter outputs is likely to be relatively slow so the bandwidth of the communications only needs to be low.

A further problem that can arise in the methods described above which use one or more photodiodes to measure and control the output intensity of the light emitters is that ambient light may interfere with this measurement. For example, sunlight may be received by the photodiode and erroneously increase the detected output light level of the light emitting element as detected by the photodiode.

To overcome this problem, in one embodiment, the effective ambient light can be greatly reduced by using a band pass filter in conjunction with the photodiode. For example, a photodiode which only passes light in a wavelength band emitted by its corresponding light emitter, but which attenuates all other wavelengths e.g. those commonly occurring in sunlight can be effectively used. Similarly, if artificial lighting such as fluorescent lighting is used, the band pass filter can be adapted to exclude substantially all of the artificial light whilst still transmitting light in a wavelength band transmitted by the corresponding light emitter.

In an alternative embodiment, light absorbing baffles may be positioned around the photodiode e.g. in the LED package such that only light from the light emitting elements can reach the photodiode. The photodiode can be shielded from external light by placing a baffle between the photodiode and the lens of the LED package.

A further mechanism for correcting for background light levels is to take measurements from the photodiode when the light emitters are in 'on' and 'off' conditions. In this case measurements taken during the 'off' periods, between pulses of the light emitters, represent the background light. This background light level can be subtracted from the next (or previous) light level measured during an 'on' period i.e. a time period in which a light emitter element is illuminated. The background light level can be averaged over several 'off' frames and a sliding average of the background level subtracted from the 'on' period data if smoothing of the background light levels is required. For example, this may be needed when the ambient light level varies greatly with a frequency equal to or substantially equal to the pulse frequency of the light emitters.

Figure 54:
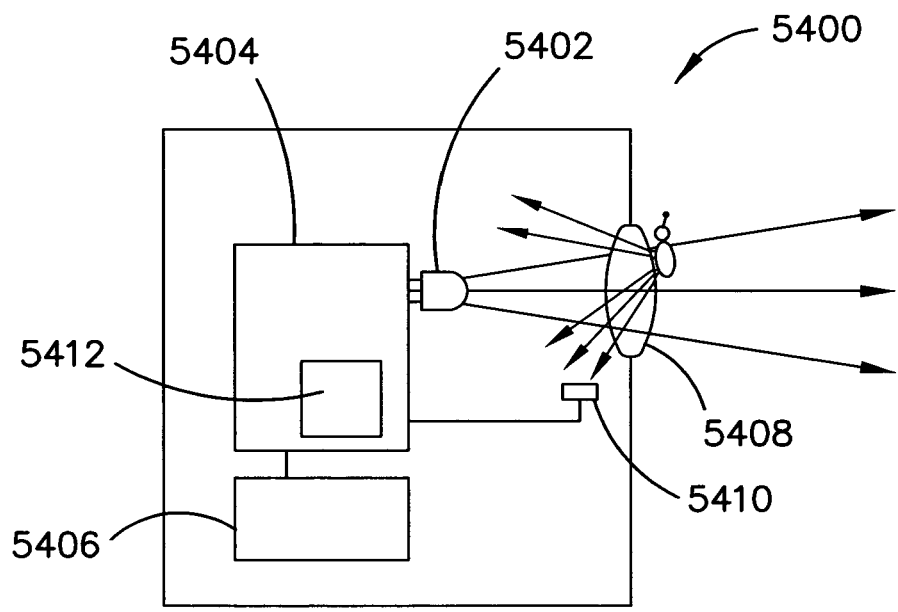
FIG. 54 illustrates a schematic representation of a light source of a beam detector employing an embodiment of the present invention.

FIG. 54 illustrates a light source made in accordance with an embodiment of the present invention. The light source 5400 includes a light emitter 5402 electrically connected to a control circuit 5404 which is powered by a power source 5406. The light emitter 5402 projects a beam (or beams) of light through an optical system 5408 towards a receiver. In some embodiments, the optical system 5408 may simply be a transparent window through which the beam of light is projected in use, but also may be a more complicated optical arrangement e.g. including one or more lenses, mirrors or filters etc. that are adapted to cause the beam of light emitted by the light source 5402 to take on particular beam characteristics. As described above the external surface of the optical component 5408 is prone to temporary occlusion by insects or the like on its outer surface.

In order to detect these foreign bodies, the light source 5400 is provided with a photodiode 5410 or other light sensitive element which is connected to the control circuitry 5404. In use the photo diode 5410 is arranged such that it will receive scattered light from foreign bodies occluding at least part of the outer surface of the optical arrangement 5408. The photo diode 5410 is connected back to the control circuit 5404 which is adapted to determine based on the integrity of the received scattered light by photo diode 5410 whether a fault condition exists. For example the control circuit 5404 can include a micro controller 5412 which is programmed with, inter alia, fault logic which compares the received feedback signal from the photo diode 5410 to a predetermined threshold and if the received intensity is above the predetermined threshold, or some other intensity and/or time based criteria are met by the feedback signal, the fault logic can be adapted to trigger a fault response in the light source 5400. For example, the microcontroller may cause an illumination pattern of the light emitter 5402 to change in response to the fault condition to signal to a receiver of the particle detection system that a fault condition exists. By encoding a particular signal in the light emission patent the type of fault could be signalled back to the receiver. The fault condition could be communicated by modulating the amplitude, duration and/or the timing of the transmitted light pulses in a predetermined fashion. This has the advantage that no wiring or other wireless communication systems are required between the transmitter and receiver of the particle detection system.

Figure 55:
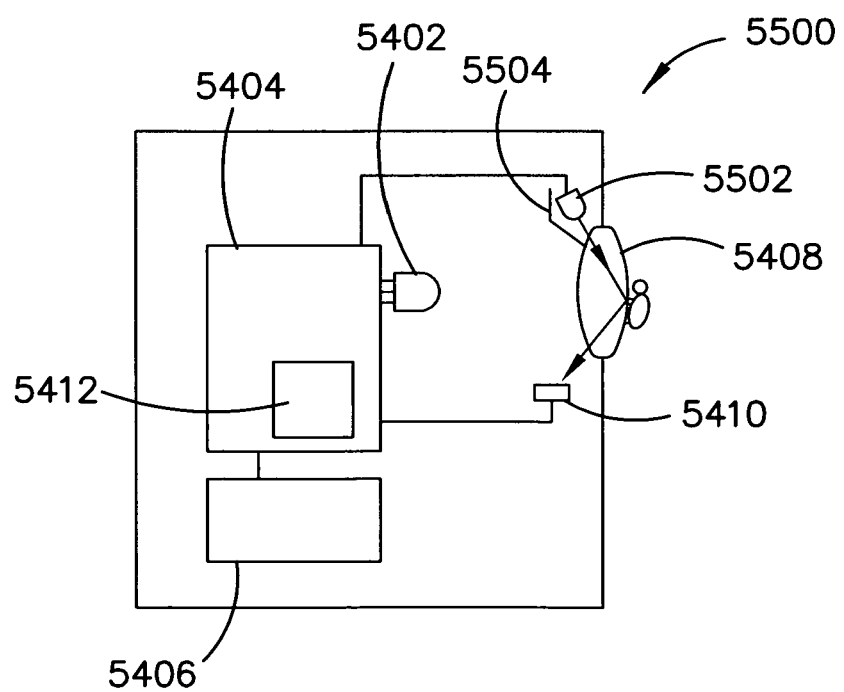
FIG. 55 illustrates a schematic representation of a light source of a beam detector employing an embodiment of the present invention.
Figure 56:
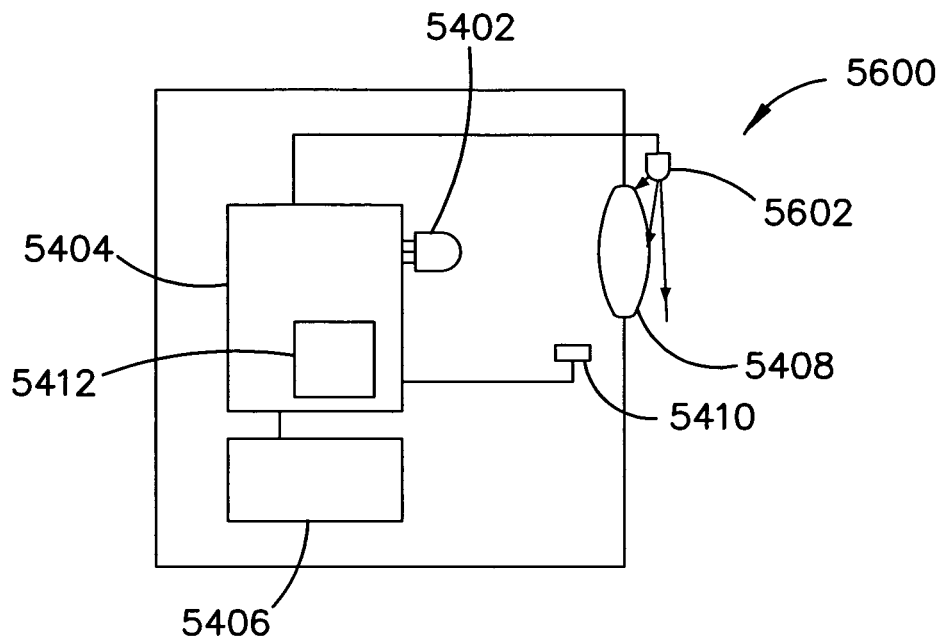
FIG. 56 illustrates a schematic representation of a light source of a beam detector employing an embodiment of the present invention.

FIGS. 55 and 56 illustrate alternative embodiments of this aspect of the present invention, and common parts have been numbered with common reference numerals.

Turning first to FIG. 55 which shows second embodiment of a light source 5500 made in accordance with an embodiment of the present invention. In this embodiment, the light source 5500 has been provided with an additional light emitting device 5502. This light emitting device is placed such that it illuminates the lens from a shallow angle of incidence. This increases the chance that particles or foreign bodies which fall on the external surface of the optical component 5408 will produce a sufficient reflection to be detected by the photo diode 5410. In this embodiment, the photo diode can be shielded by a wall or baffle 5504 to prevent direct illumination of it by the light source 5502.

FIG. 56 illustrates a light source 5600. This embodiment differs from the light sources illustrated in FIGS. 54 and 55 by the inclusion of an externally mounted light emitter 5602. This light emitter 5602 is positioned such that it illuminates the outside surface of the optical component 5408 directly. This may have additional advantages in correctly identifying the presence of foreign bodies such as insects or the like on the external surface.

In some embodiments of the present invention the light source may be provided with an internally mounted feedback photo diode. This feedback photo diode is typically used to monitor the light output of the light source or sources and adjust the emission characteristics of the light source e.g. if a decrease in received light level is measured. However, the internal photo diode could be used with embodiments of this aspect of the invention by applying an upper threshold to its received signal and if the received light level is above the upper threshold (and is not the result of an increase in light output caused by the controller 5404) this may be determined to be the result of a foreign body on the external surface of the optical system 5408.

An embodiment of the present invention may also be able to be used with a receiver of a particle detection system. In this embodiment, the receiver can be fitted with a light emitter such as that in FIG. 14 and photo diode and be configured to implement the method as described herein in relation to a light source. With the receiver, it is clearly advantageous that the transmission of light within the receiver housing does not interfere with the particle detection performance of the system. Accordingly, the light source 5502 can be selected such that it emits light outside the reception band of the receiver, or the receiver can be provided with a band pass filter which excludes the selected wavelength. Alternatively, if the light source of the particle detector is set to flash according to a predetermined pattern with 'off periods' between flashes the foreign body detection function can be performed in these 'off' periods. If foreign body detection in the 'off' periods is to be used the light emitter e.g. emitter 5502, can emit light in the pass band of the receiver and the main receiver could be used to detect the presence of foreign bodies on the external surface of the optical component 5408.

As noted above, it is important for particle detectors to be properly installed and commissioned. Correct installation and commissioning ensures reliable and safe operation of the system. In this regard several processes that can be used in the set-up and commissioning of a particle detection system will now be described.

For the purposes of clarity, the following process description will focus on a particle detector as described in relation to FIG. 2. However, the process may be implemented using the implementations described in relation to FIG. 3 and other implementations, which will be apparent to a person skilled in the relevant art.

In one embodiment, the process includes two stages, comprising a commissioning stage and an operation stage. The commissioning stage is performed on initial installation of the beam detector, whereas the operation stage is performed some time after installation.

Figure 58:
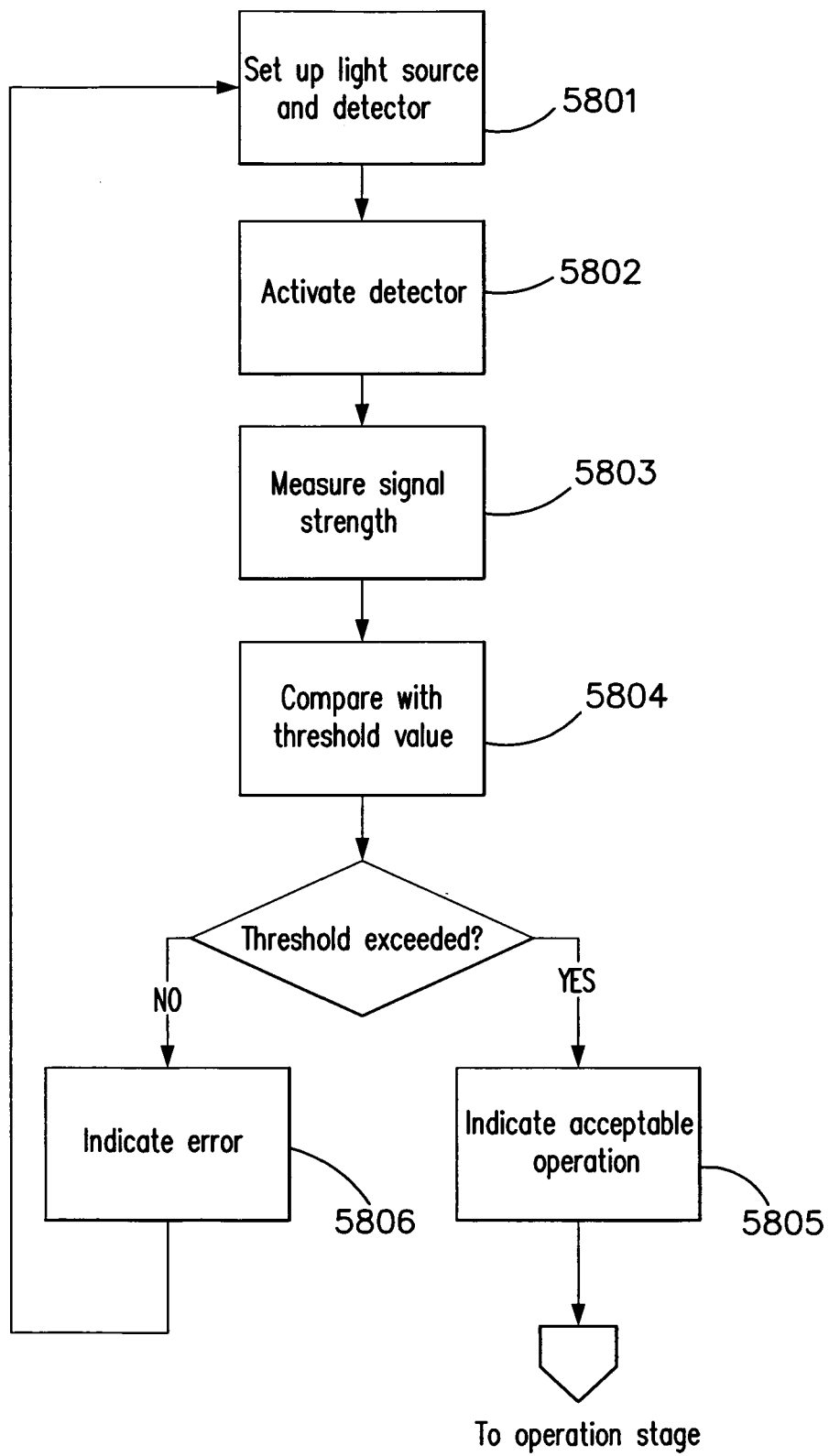
FIG. 58 shows a flow chart of one embodiment of process that may be implemented to install a beam detector operating in accordance with an embodiment of the present invention.

A process for commissioning the particle detector is shown in FIG. 58. A technician or other suitable installer mounts the light source 32, and receiver 34 and target 36 (which is optional in other geometries) in appropriate locations spanning an area requiring monitoring for particles e.g. smoke (step 5801). As discussed, with the use of a receiver 34 in the form of a video camera or other suitable device, the process of installation may be easier and quicker.

Following installation, in step 5802, the technician activates the detector by powering the particle detector. Initially the detector discovers the presence of light sources within its field of view to monitor. As described elsewhere here and in our co-pending application the controller identifies the relevant portion(s) of the detector's field of view that represent light from the light source 32 and then measures the strength of the light signal received from the light source 32, in step 5803. This identification process may be manual, for example with the technician interfacing a portable computer to the receiver 34, viewing the image captured by the camera and indicating using a point and click device or otherwise the relevant portions of the field of view. The identification process may instead be automatic, for example with the controller 44 programmed to identify the parts of the screen illuminated by the light source (e.g. UV and/or infrared light in the case that UV and/or ultraviolet light sources are used).

A detailed description of an exemplary method of target acquisition and timing discovery can be found elsewhere herein.

The level of light received from each identified source is compared to a threshold value to determine if the received light level is within acceptable limits in step 5804. If the controller 54 receives light from the light source 32 above a preset threshold, then it causes the particle detector to indicate acceptable operation (step 5805). Indication of the status of the system can comprise constantly lighting an LED on the receiver 34, although other notification mechanisms may be used such as making a sound and/or transmitting a signal to a PDA or computer in communication with the controller 44, for viewing by the technician.

The detection system will apply alarm and fault logic to determine either whether the detection system is operating correctly or whether particles have been detected. The alarm and fault logic will include alarm criteria based on the intensity of light received at the receiver. This criteria may be based on raw intensity measurements, differential or comparative values at multiple wavelengths or rates of change or other measures known to those skilled in the art. Typically the criteria can be seen as a comparison of received data to a threshold level. The inventors have realised that since Installation and commissioning of the particle detection system is supervised by the technician and during commissioning the system is not relied on to provide a particle detection or life safety function, the usual alarm thresholds may be largely ignored in the commissioning stage. Thus the thresholds applied during commissioning stage can be set very tightly in comparison to one or more of the alarm or fault thresholds that are applied during the operating stage.

In a preferred form at least one threshold used in the commissioning stage will be set substantially above a level that would cause the particle detector to generate an alarm, take other action indicating that smoke has been detected or raise a or fault in the operation phase.

For example the acceptable minimum level of light received during the commissioning stage could be set 20% over a light level that would cause a fault condition during normal operation. Such a threshold requires an installer to ensure that the initial alignment of the system is highly accurate, the optical surfaces are clean and in good condition and that the transmission path length is not outside acceptable ranges, otherwise the system would not achieve the relatively stringent light intensity requirements in place during commissioning.

If during the commissioning stage the controller 44 determines that the intensity of the light received is below the preset threshold, then the controller 44 causes the particle detector to indicate an error (step 5806). This may, for example, comprise flashing an LED or transmitting a signal to a PDA or computer of the technician. If the identification of the relevant portions of the field of view is automatic, the controller 44 may allow a manual identification process to be completed, following which steps 5802 to 5804 may be repeated.

On receipt of the error indication, the technician can perform the necessary action to rectify the problem. For example the technician can reposition the light source 32, receiver 34 and/or target 36, for example to reduce the path length between the light source 32 and the receiver 34. Where a substantial reduction in path length is required and the initial installation used the target 36, the technician may remove the target 36 and place the receiver 34 where the target 36 was previously located, to halve the path length. The technician could otherwise locate a suitable mid-point on which to mount the components of the particle detector.

The controller 44 may be programmed to complete its part of the process shown in FIG. 58 automatically on each power up. Alternatively, the process may be completed only on command, for example by the pressing of a button associated with the receiver 34, or on receipt of a command through a communication port of the receiver 34.

If the commissioning stage has been successfully completed, the receiver 34 is in condition to start operating. Two embodiments of this 'operation stage' are described below, the first in relation to FIG. 59 and the second in relation to FIG. 60. During the operation stage, the receiver 34 measures the intensity of light received from the light source(s) 32. This data is processed, and if the signal(s) received indicates smoke is present in the light path between the light source(s) 32 and the receiver 34, the controller 44 generates an alarm condition in the particle detector, and/or communicates a signal to cause another device (e.g. a fire panel) or system such as an automated evacuation system, to generate an alarm.

In the preferred embodiments of the present invention, which operate a multiple wavelengths, the primary alarm thresholds are based on a differential measure of received light intensity at more than one wavelength, e.g. the ratio or difference between received light intensity at two wavelength, or rates of change of such measures. A secondary "fallback" threshold can be set on the basis of the absolute or corrected received light intensity at one or more wavelengths independently. The detection of correct operation and fault conditions can also be based on both differential or absolute received light level.

Figure 59:
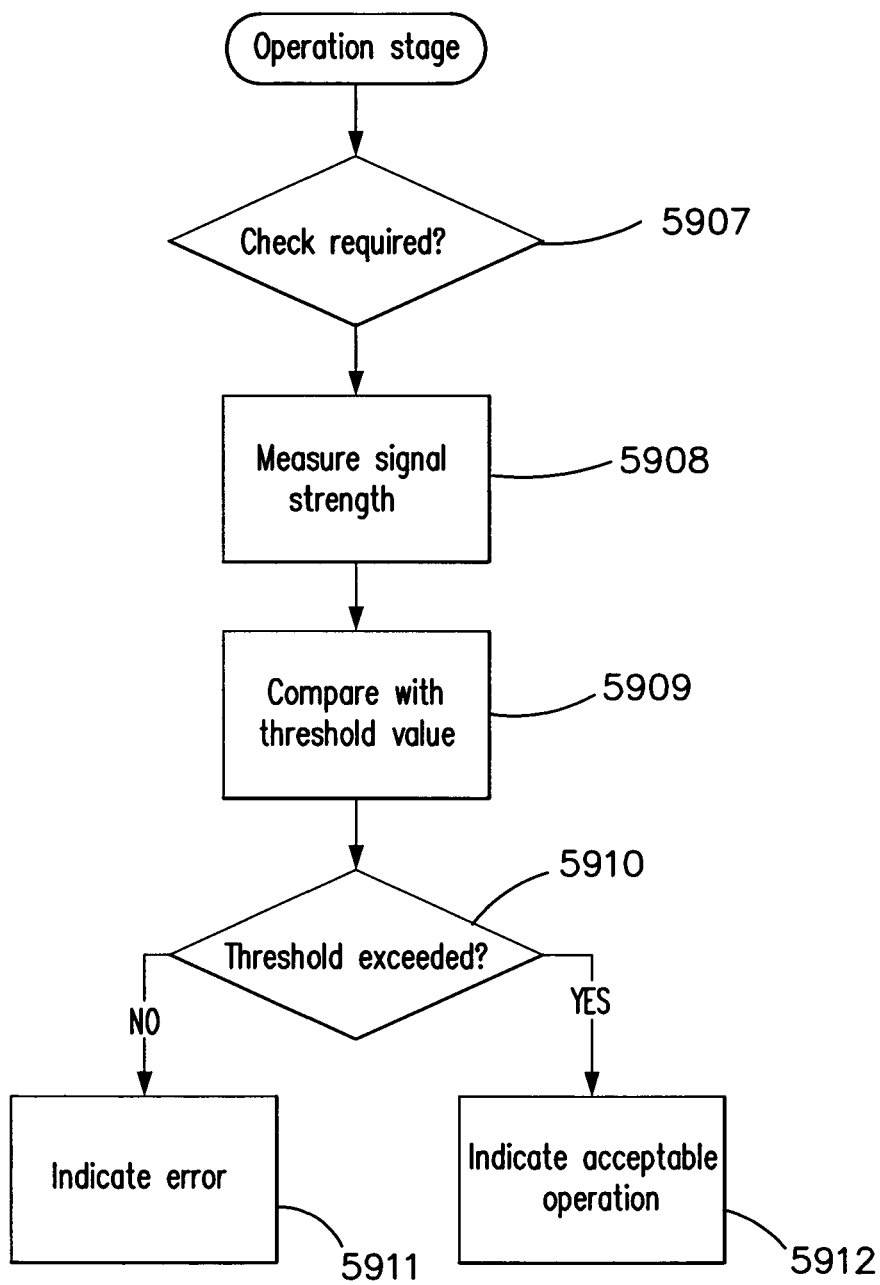
FIG. 59 shows a flow chart of one embodiment of a process that may be performed by a controller of a beam detector according to an embodiment of the present invention after installation.

Referring to FIG. 59, the controller 44 is programmed to re-check the signal strength received from the light source 32, or each light source 32 (if there is more than one) against an absolute signal strength threshold. This check may be performed continuously or periodically, for example, once a day, two or more times a day, or at a lesser frequency, depending on requirements. The check may also be performed on command, for example on receipt of a command to check the signal strength received at a communication port of the receiver 34, or on actuation of a button provided in association with the receiver 34. If the controller 44 determines in step 5907 that no check is required, the receiver 34 continues to monitor for smoke in the light path.

If a check is required, then in step 5908 the controller 44 evaluates the signal strength of the light from the light source(s) 32 and in step 5909 compares this to a threshold value. This threshold value may be the same as that used in step 5803, or may alternatively be another set value, determined to indicate a required level of reliability of operation.

In step 5910, the result of the comparison is evaluated and if the threshold value for minimum required intensity has not been exceeded, an error is indicated/generated (step 5911), which error may be the same as or different to the error indicated in step 5806, depending on the particular implementation. For example, the error indicated in step 5911 may be an audible signal generated at the site of the particle detector, and/or at a control station, such as a security station for a building, and/or a remote monitoring station by communicating the error over a wired and/or wireless public and/or proprietary network.

If the threshold value for minimum required intensity has been exceeded, then in step 5912, the particle detector indicates acceptable operation, which may be indicated in the same was as described for step 5805.

Figure 60:
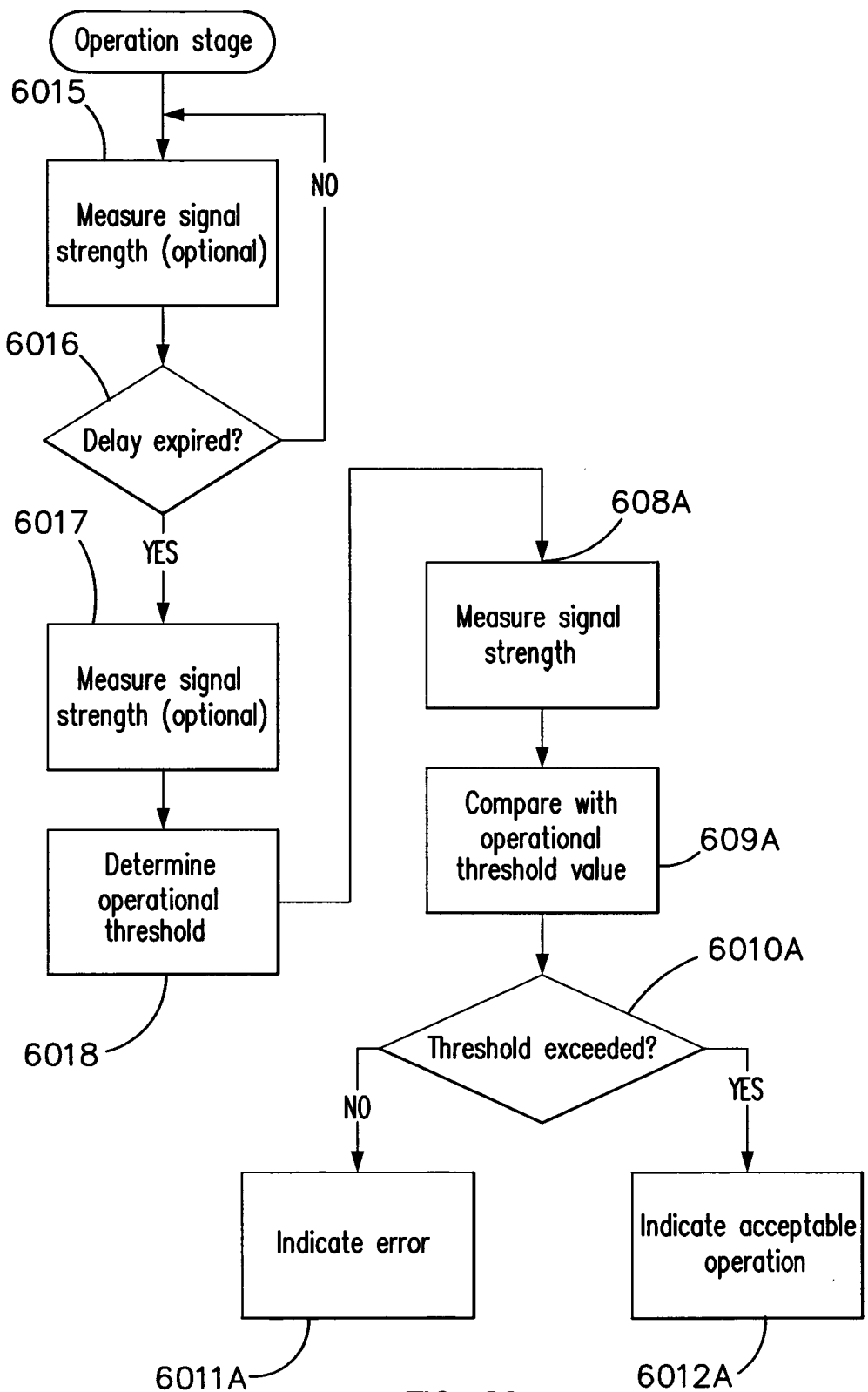
FIG. 60 shows a flow chart of another embodiment of a process that may be performed by a controller of a beam detector according to an embodiment of the present invention following installation.

Referring to FIG. 60, a flow chart of a process that may be completed by the controller 44 to implement an alternative operation stage is shown.

Following commissioning (i.e. following step 5805), the controller 44 in step 6016 determines if a delay period has expired. This delay period may, for example, be 24 hours, after which time it would be expected that the particle detector is operating in a stable condition. Other non-zero delay periods may be used in other embodiments. Preferably during the delay period the detector is not used for essential particle detection purposes, and is only being monitored for correct operation.

When the delay period has expired, the controller 44 re-sets its thresholds (in step 6018). Preferably the new thresholds to be used are based on either the measured signal strength (or parameter derived therefrom) that was measured in (optional step) 6015. Alternatively, it could be based on a measurement(s) made upon the expiry of the delay (step 6017). The operational threshold intensity could also have a preset minimum value. Alternatively an acceptable threshold can be determined by looking at the performance of the system during the delay period, e.g. by analysing the variation of received light intensity at one or more wavelengths during the delay period. For example if the variation in received light intensity over the period caused by things other than the impingement of particles of interest into the beam (e.g. mounting drift, temperature dependent light output variations of the light sources etc.) is 2% then an acceptable minimum received light level could be set at 2% below the average received light level, or at some other level. The operational intensity may be a function of both the measured intensity at the end of the delay period and a preset minimum value, for example determined as the average of the two values. The operational threshold and present minimum value, if any, may be determined/set independently for each light path if there is more than one light path.

Next the controller evaluates the intensity of the light received from the light source(s) 32 (step 6088A) and compares it to the new operational threshold in step 609A.

Steps 600A to 602A may then proceed as described herein above in relation to FIG. 59, using the operational threshold value determined in step 689A.

Where there are multiple light sources and/or multiple light paths from a single light source, the error may be indicated when the intensity of light received along any one of the monitored light paths falls below the threshold. Alternatively, there may be different levels of error condition, with one level indicating when light along one of the light paths falls below the threshold and another level indicating when light alone more than one or all paths falls below the threshold. The threshold may be different for each light path, reflecting for example differences in the intensity of light generated by the light source 32 for that path.

In the foregoing description, reference has been made to individual light paths from the light source(s) 32 to the receiver 34. Those skilled in the relevant art will appreciate that light may be reflected off various structures, such as a ceiling, and as a result there may be more than one light path between a light source and a particular point on a receiver. Implementations where light from a source is received by the receiver by multiple paths and where light from one light source is reflected onto the part of the receiver receiving light from another light source are intended to be within the scope of the present invention.

Figure 57:
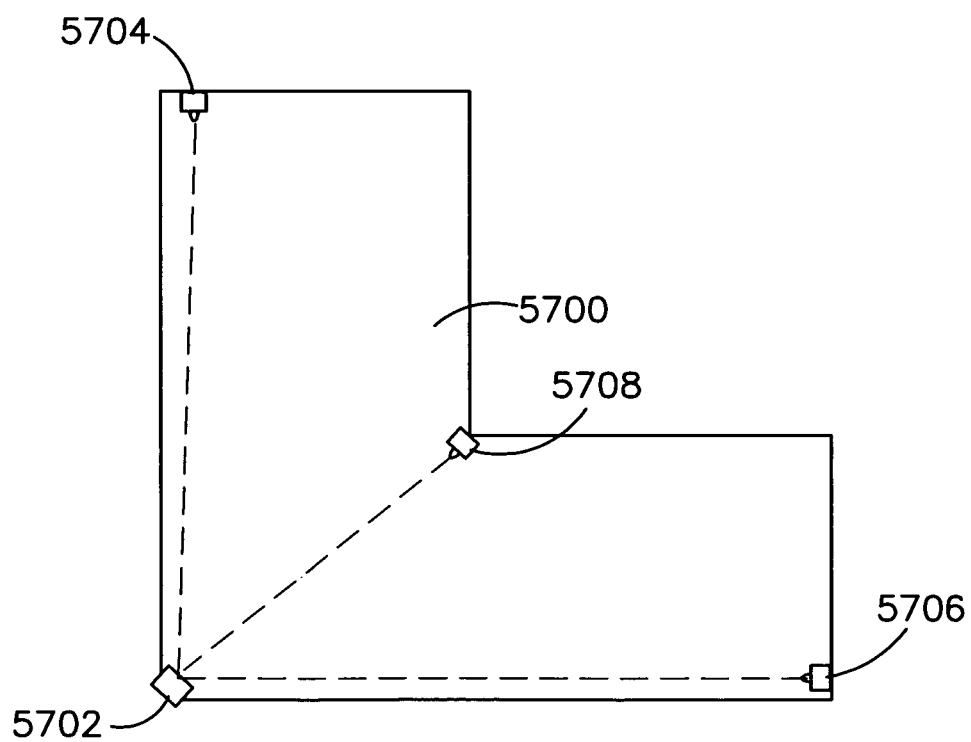
FIG. 57 illustrates a room in which a particle detection system according to an embodiment of the present invention is installed.
Figure 61:
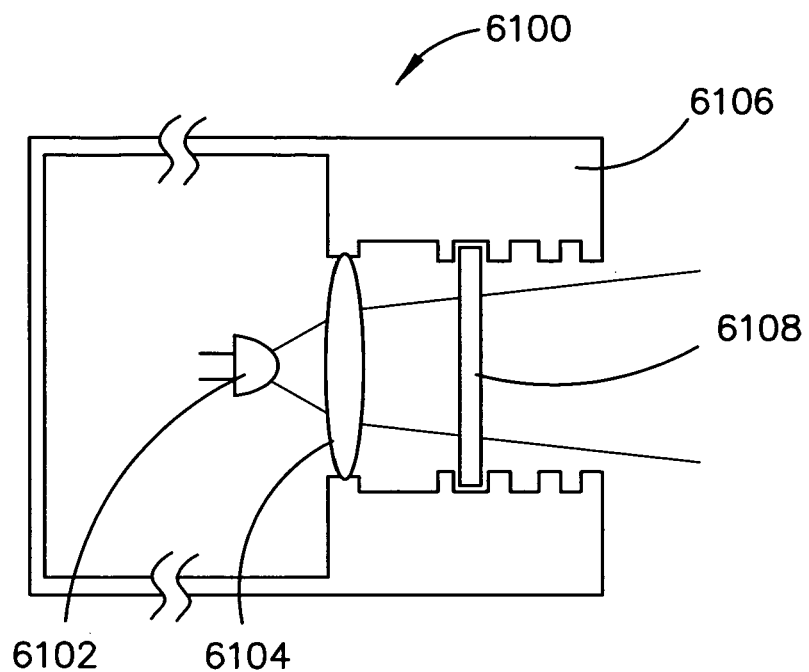
FIG. 61 illustrates schematically part of a transmitter according to an embodiment of the present invention.
Figure 62:
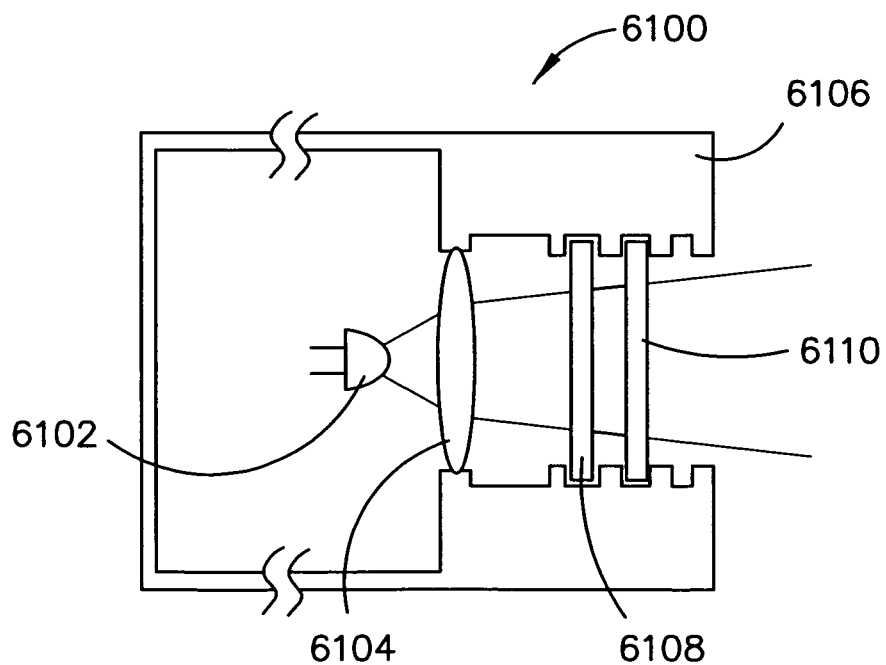
FIG. 62 shows a second embodiment of the transmitter illustrated in FIG. 61.

Turning again to FIG. 57, in an installation such as this, the difference in the intensity of light arriving at the receiver 5702 from the transmitters 5704, 5706, 5708 can be adjusted in an embodiment of a further aspect of the invention by applying an optical attenuator to the optical path of each transmitter in the system, or at least those transmitters in the system which are located at a distance likely to cause saturation of the receiver 5702. FIG. 61 shows exemplary housing which may be used to implement this mechanism. FIG. 61 shows a cross sectional view through a transmitter housing 6100. Within the housing there is located a light source such as an LED 6102. This is connected to appropriate circuitry (not shown) and is used to generate a beam of light for use in particle detection. The light emitted by the light source 6102 may pass through one or more optical elements 6104 for focusing the beam into an appropriate shape eg a narrowly diverging column or broad divergent beam, or some other shape as discussed herein. The transmitter 6100 additional includes one or more optical attenuators 6108 for attenuating the beam emitted from the transmitter 6100. The level of attenuation can be selected and set at an appropriate level for the separation between the transmitter and its corresponding receiver by using one or more filters 6108 having suitable ???? characteristics. Multiple filtering elements can be added in series to achieve the appropriate attenuation level. An example of a system with multiple filters is shown in FIG. 62. In FIG. 62 like components have been numbered to correspond to FIG. 61. In a preferred embodiment the housing 6106 of the transmitter 6100 can be configured to have structures 6112 for receiving the filters 6108 (and 6110) in the appropriate position. Most preferably, the receiving mechanism enables selectable filters to be attached and removed by the installer during commissioning of the system. For example, the housing can include a plurality of grooves, e.g. grooves 6112, which are each adapted to receive an individual filter element.

Figure 63:
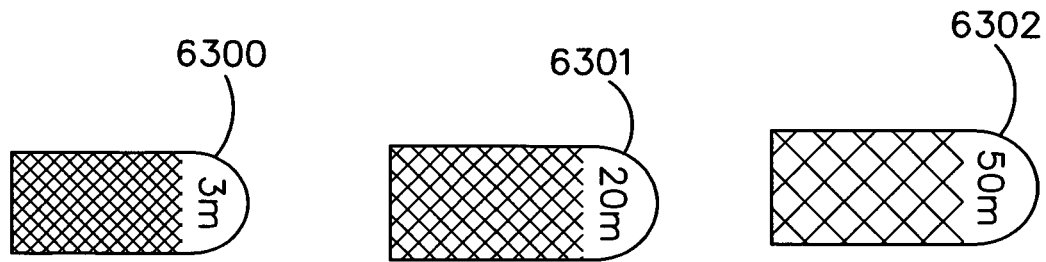
FIG. 63 illustrates exemplary attenuators able to be used with an embodiment of the present invention.

FIG. 63 shows three exemplary filter elements which may be used with an embodiment of the present invention such as that illustrated in FIG. 61 or 62. The filters 6300, 6301, 6302 are preferably neutral density filters and can be made of an attenuating material, such as a plastic film. Attenuators for different distances can be made by increasing the level of absorption of the material e.g. by changing material properties or increasing thickness of the material.

Preferably each filter has indicia indicating the strength of the filter. For example, an indication of a preferred distance or distance range between the transmitter and receiver can be printed, embossed or otherwise displayed on the filter. Alternatively, a fractional attenuation level can be displayed. This information displayed on the filters can be used by the installers to determine the appropriate filter or group of filters to use with a transmitter for the particular system geometry being installed.

Figure 64:
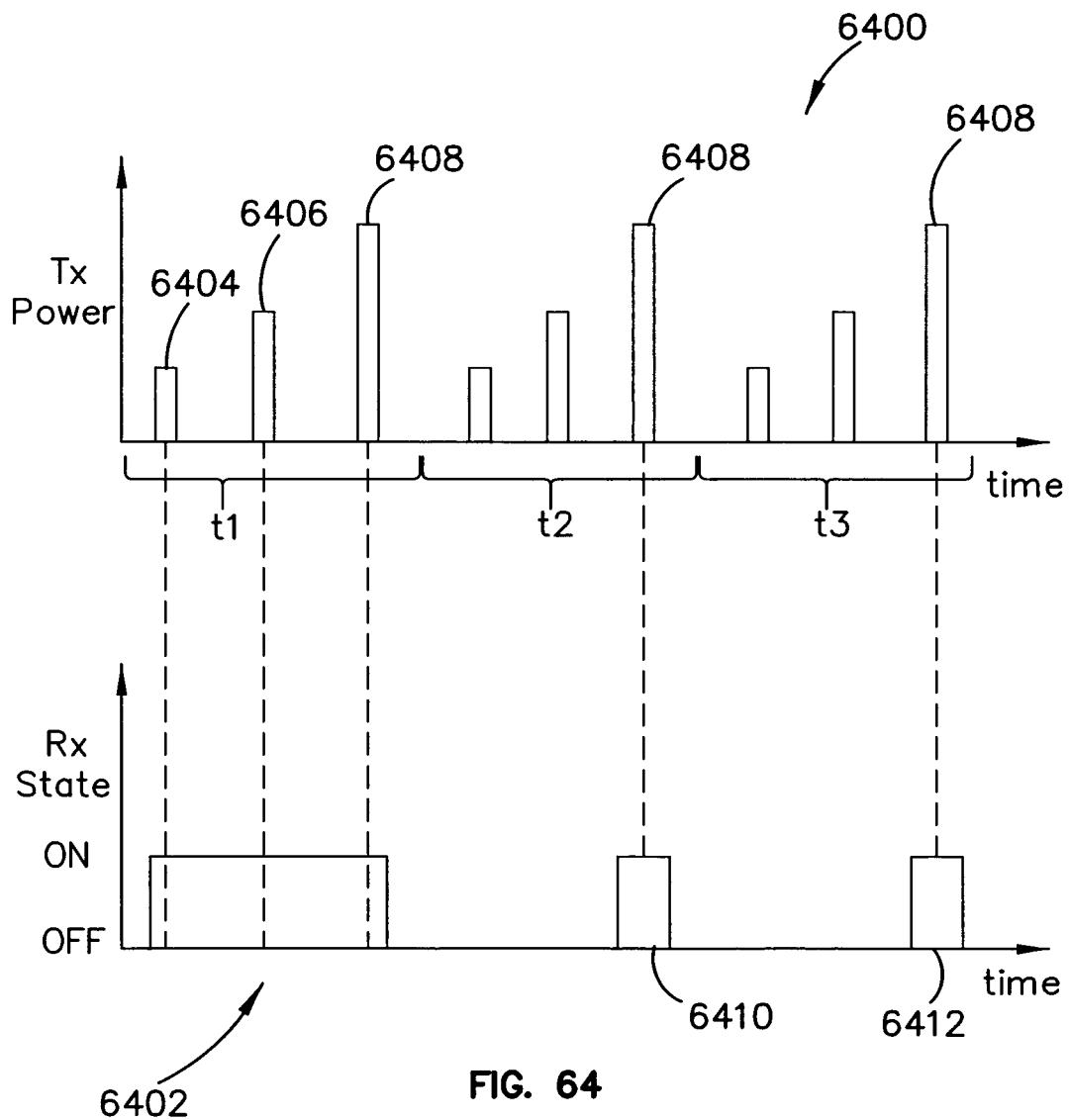
FIG. 64 is a timing diagram illustrating graph of transmission power and corresponding receiver state illustrating another embodiment of the present invention.

An alternative (or complimentary) embodiment of this aspect of the invention will now be described. In this embodiment the system is adapted to enable the receiver to avoid saturation without the use of a filter, although filters could be used with this embodiment if necessary. FIG. 64 is a timing diagram illustrating a second solution to the abovementioned problem according to an aspect of the present invention.

In this aspect of the invention a transmitter can be configured to emit a sequence of pulses of differing intensity and to repeat this sequence during operation. The receiver can then determine which of the received pulses falls within an acceptable light level at the receiver and from that time forward choose to receive only those pulses which have an acceptable light level.

Turning now to FIG. 64 the uppermost plot 6400 is a timing diagram showing the transmission power of a sequence of pulses emitted by a transmitter over time. The lower plot shows the reception state of the receiver. In an initial time period $t_1$ the transmitter cycles through a sequence of transmission pulses 6404, 6406 and 6408 of progressively increasing transmission power. This sequence is repeated in time periods $t_2$ and $t_3$ and continuously thereafter. In the first time period $t_1$ the receiver does not know which transmission pulse is going to be at the appropriate level so as not to saturate the receiver but also be high enough to have adequate signal to noise ratio. Therefore, for time period $t_1$ the receiver is continuously in an "on" state and is able to receive each of the transmitted pulses 6404, 6406 and 6408. On the basis of measured intensity of the three received pulses the receiver can determine which pulse should be received from then on. In this case, the pulse 6408 is determined to have the correct intensity and the receiver is configured to be activated at times 6410 and 6412 which correspond to the time of transmission of pulse 6408 in the successive transmission periods T2 and T3.

As described above the receiver and transmitter are generally not in communication with each other, and the transmitter will continue to emit three different level pulses throughout its operation. Alternatively, in an embodiment where the receiver may communicate back to the transmitter, the receiver can signal to the transmitter which of the pulses to continue emitting and which of the pulses to omit. Such a system will reduce the power consumption of the transmitter as fewer pulses will be emitted.

The initial period of monitoring the various transmission pulses may be extended beyond the single transmission time period as it may be necessary for the receiver to discover the pattern of illumination of the transmitter over several transmission time periods.

In a third solution for ameliorating or addressing this problem a further aspect of the present invention uses electronic means to control the transmission power of the transmitter. In this example a DIP switch can be incorporated into the transmitter which during installation is set to the appropriate transmission level by the installer. The setting on the DIP switch can be chosen to either reduce the current through the LED and thus dim the LED or reduce the duration of the pulse "on period" to avoid saturation of the receiver. In this case it may be advantageous to have an installation mode in which the transmitter emits light at differing power levels initially. During this period the receiver can determine the appropriate transmission level and indicate to the installer the appropriate DIP switch setting (or settings) to be made to set the transmission level to the most preferable value. For example, the receiver may be provided with a display or other interface that can be used to indicate the DIP switch settings for the transmitter. It should also be appreciated that in a system with a plurality of transmitters any process can be repeated for each transmitter.

In a further embodiment of this aspect of the present invention a system having multiple transmitters may include transmitters of different types in it. Each transmitter type can be optimised for use at a particular distance or range of distances and in this case is up to the installer to select what type of transmitter should be installed.

Figure 65:
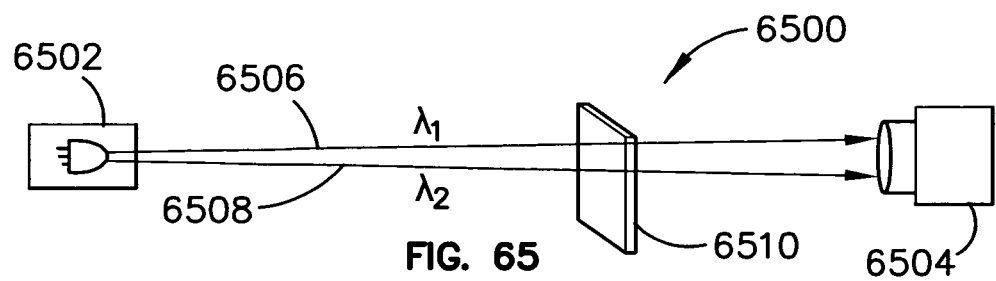
FIG. 65 illustrates schematically a particle detection system employing a test filter in accordance with an aspect of the present invention.

FIG. 65 illustrates an embodiment of a particle detection system 6500 being tested using a test filter according to an embodiment of another aspect of the present invention. The particle detection system 6500 includes a light source 6502 a light receiver 6504. The light source 6502 generates one or more beams of light including light in a first wavelength band 6506 which is in a wavelength band centred at $\lambda 1$ and a second wavelength band 6508 centred at $\lambda 2$. Preferably, $\lambda 1$ is a shorter wavelength band, for example in the ultraviolet part of the electromagnetic spectrum, and $\lambda 2$ is a longer wavelength band e.g. centred in the near infrared. The light beams 6506 and 6508 pass through a test filter 6510 which mimics the effect of smoke on the beam by alternating the beams 6506, 6508. The operation of the receiver 6504 can then be checked to determine if its behaviour is correct given the extent of beam attenuation being caused by test filter 6510. Because the light emitted by light source 6502 includes light in two wavelength bands $\lambda 1$ and $\lambda 2$ the filter 6510 needs absorption characteristics which treat these two wavelength bands in an appropriate manner. In a preferred form of particle detector 6500, as described above, a differential measure of light intensity in the two wavelength bands $\lambda 1$ and $\lambda 2$ (e.g. ratio of measured intensities at each wavelength or a rate of change of these values etc.) is used to determine the presence of particles of a predetermined size range within the beams 6506 and 6508. Most preferably, if the ratio of the received light intensities varies in a predetermined manner then a particle detection event may be indicated. Accordingly, in most cases the test filter 6510 does not attenuate both wavelength bands evenly but must provide a differential attenuation in the two wavelength bands $\lambda 1$ and $\lambda 2$ to mimic the effect of smoke. In this example, the test filter 6510 absorbs the shorter wavelength $\lambda 1$ significantly more than the longer wavelength $\lambda 2$. For example, the test filter can absorb twice as much of the light in $\lambda 1$ as it does in $\lambda 2$, which may be determined to look like a particular type of particle.

Thus the test filter characteristics are chosen to set both the ratio of light transmitted (or attenuated) in different wavelength bands and to also to vary the absolute level of light transmitted (attenuated) by the test filter. These two variables can be adapted to produce a suitable test filter to mimic different smoke or particle types as well as different smoke or particle densities.

Figure 66:
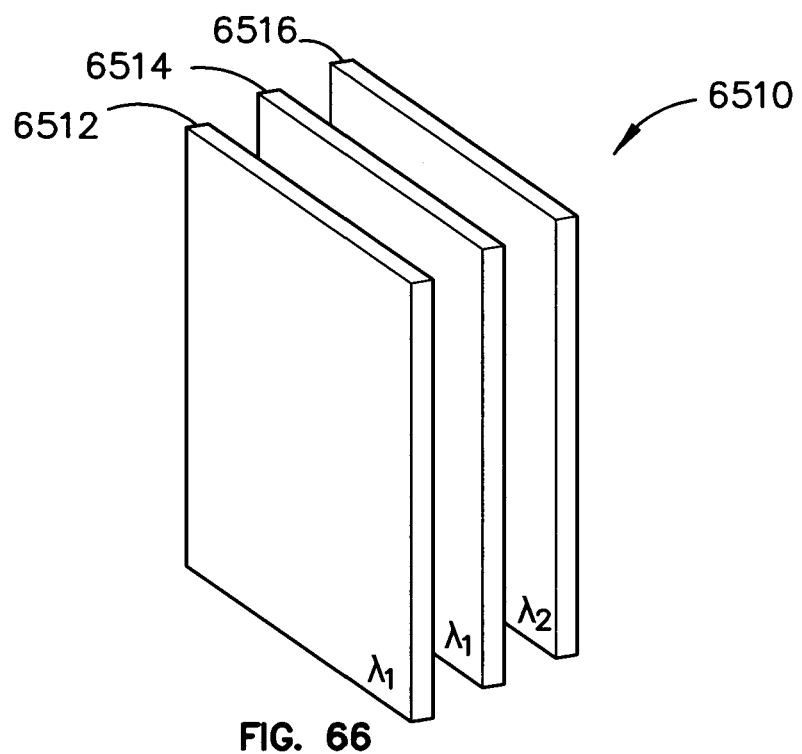
FIG. 66 illustrates an exemplary test filter made in accordance with an embodiment of the present invention.

FIG. 66 illustrates a first exemplary test filter comprising three filter elements 6512, 6514 and 6516. The test filter 6510 is a generally sheet like material formed by three layers of filter material. In this example, the first two filter elements 6512 and 6514 attenuate light in wavelength band $\lambda 1$ and the third filter element 6516 absorbs light in wavelength band $\lambda 2$. In this example each of the filter elements 6512 to 6516 making up the test filter 6510 are configured to provide the same amount of attenuation of light passing through it. Accordingly, the test filter 6510 attenuates light in wavelength band $\lambda 1$ twice as strongly as it does light in wavelength band $\lambda 2$.

Figure 67:
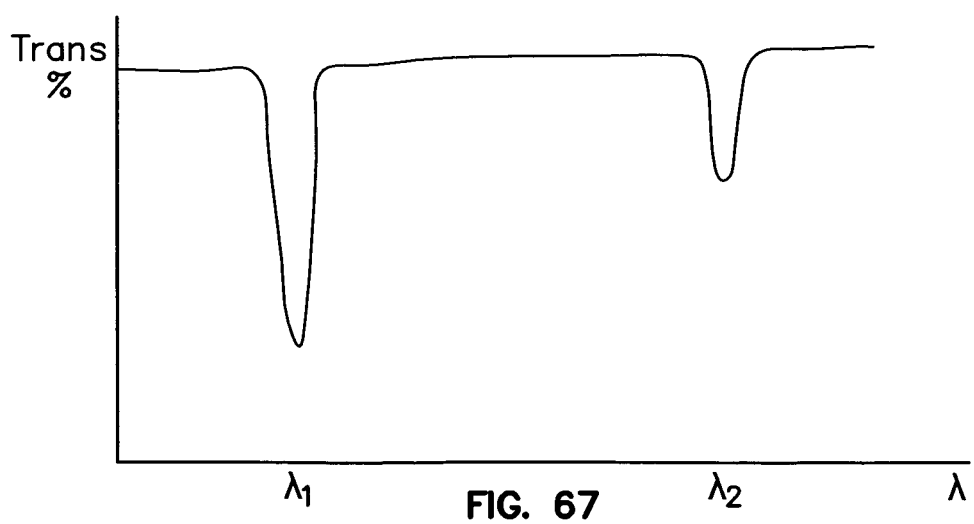
FIG. 67 is a plot of the transmission spectrum of a filter made in accordance with an embodiment of the present invention.

FIG. 67 illustrates a transmission spectrum for the test filter 6570. As can be seen, the test filter transmits substantially all of the light outside wavelength bands $\lambda 1$ and $\lambda 2$ but attenuates about twice as much of the light in wavelength band $\lambda 1$ as it does light in wavelength band $\lambda 2$. In other embodiments transmission outside wavelength bands $\lambda 1$ and $\lambda 2$ can be any level and need not be uniform over all wavelengths.

The absorption characteristics described above can be achieved in a wide variety of ways. FIGS. 68 to 75 illustrate a range of these techniques. Others may be apparent to those skilled in the art.

Figure 68:
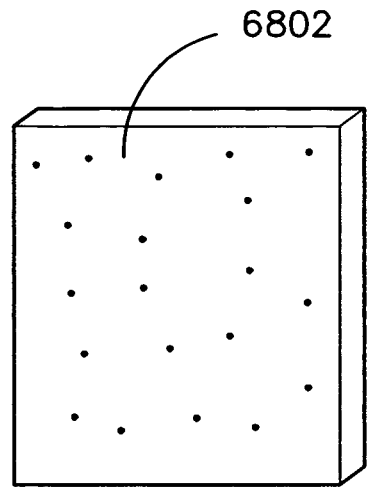
FIG. 68 to FIG. 75 illustrates various embodiments of filters made in accordance with an aspect of the present invention.
Figure 69:
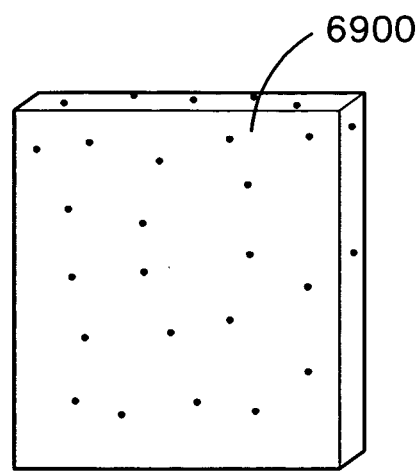

FIG. 68 illustrates a filter element. The filter element has a front face 6802 to which is adhered a plurality of particles having a particle size distribution substantially equal to the particles to be detected using the particle detector to be tested using the filter element. Such particles can be manufactured using a number of well known processes or selected by filtration and separation from powder such as aluminium oxide. FIG. 69B illustrates a variant on this mechanism. The filter element 6900 of FIG. 15B includes particles similar to those used in the embodiment of FIG. 68, but distributed through the bulk of the filter element.

Figure 70:
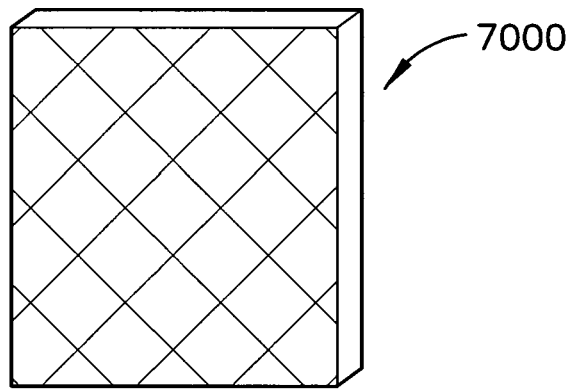

FIG. 70 shows a filter element 7000 on which one or both surfaces has had a surface treatment to cause defects on the surface of the material. Surface defects can be generated for example by mechanical abrasion, particle blasting, chemical or laser etching or the like. Alternatively defects may be created through the bulk of the filter element in FIG. 70 using for example 3D laser etching.

Figure 71:
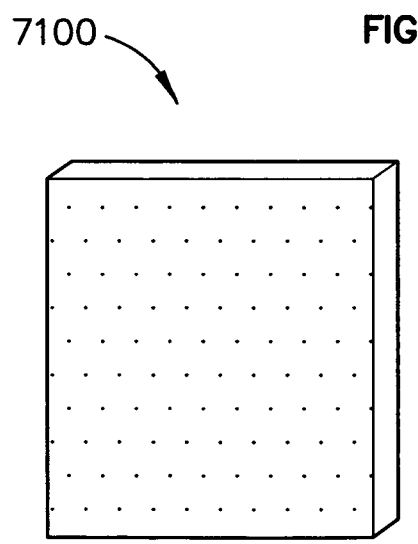
Figure 72:
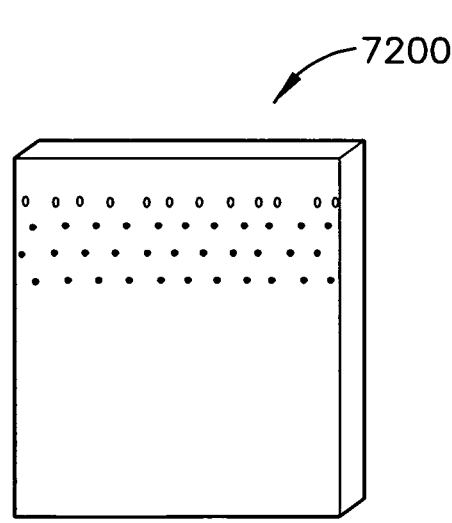

FIGS. 71 and 72 illustrate further surface treatments that can be performed on filter element 7100, 7200 to achieve predetermined attenuation characteristics. In these examples the filter element is formed of a substantially transparent material and is modified by the application of surface printing. For example, an inkjet or laser printer can be used to print a pattern on one or both surfaces of the filter element sheet. Preferably, a pattern of dots is printed over the entire surface of the filter element. Most preferably the dots of a uniform size are printed at a predetermined separation which is determined by the level of attenuation to be achieved by the filter element. FIGS. 71 and 72 are substantially identical apart from the number of dots printed on the filter element. As can be seen, FIG. 71 has far less dots printed on it than FIG. 72 and accordingly will be less absorptive than the filter element of FIG. 15E.

Obviously other patterns can be used to achieve a predetermined attenuation.

Figure 73:
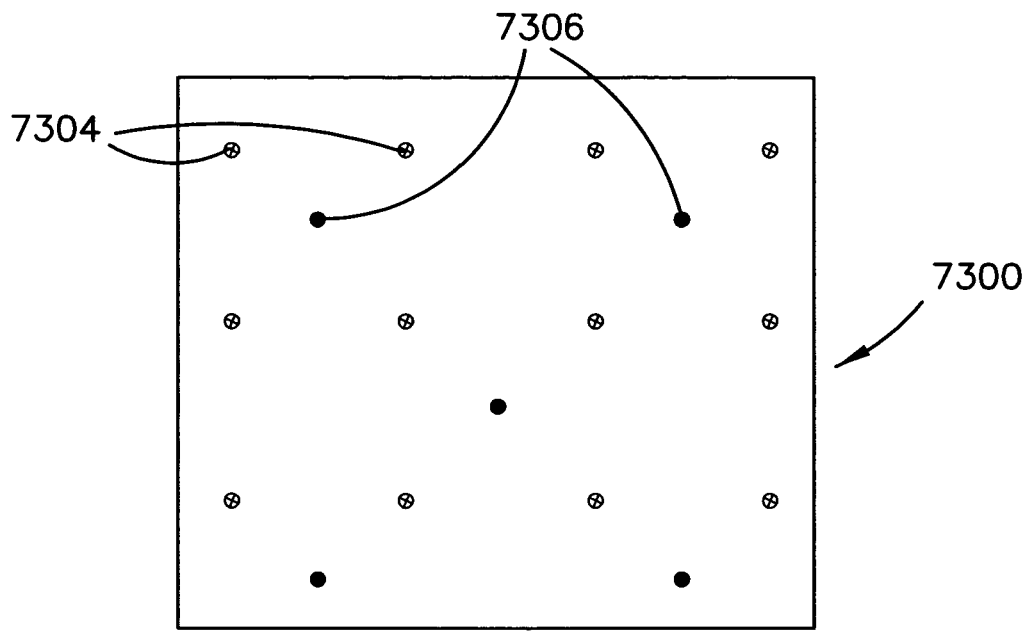

FIG. 73 illustrates a printing pattern which can be implemented on a surface of a filter element 7300. This filter element 7300 is printed with two colour printing process and includes a dot pattern which has dots of a first colour 7304 and dots of a second colour 7306. As can be seen there are more dots of colour 6804 than of colour 6806 and accordingly the filter element will attenuate more light in one wavelength band than the other. Alternatively, a dot pattern in one colour, could be printed on one side of the filter element and a dot pattern on the other side can be printed in the second colour.

Figure 74:
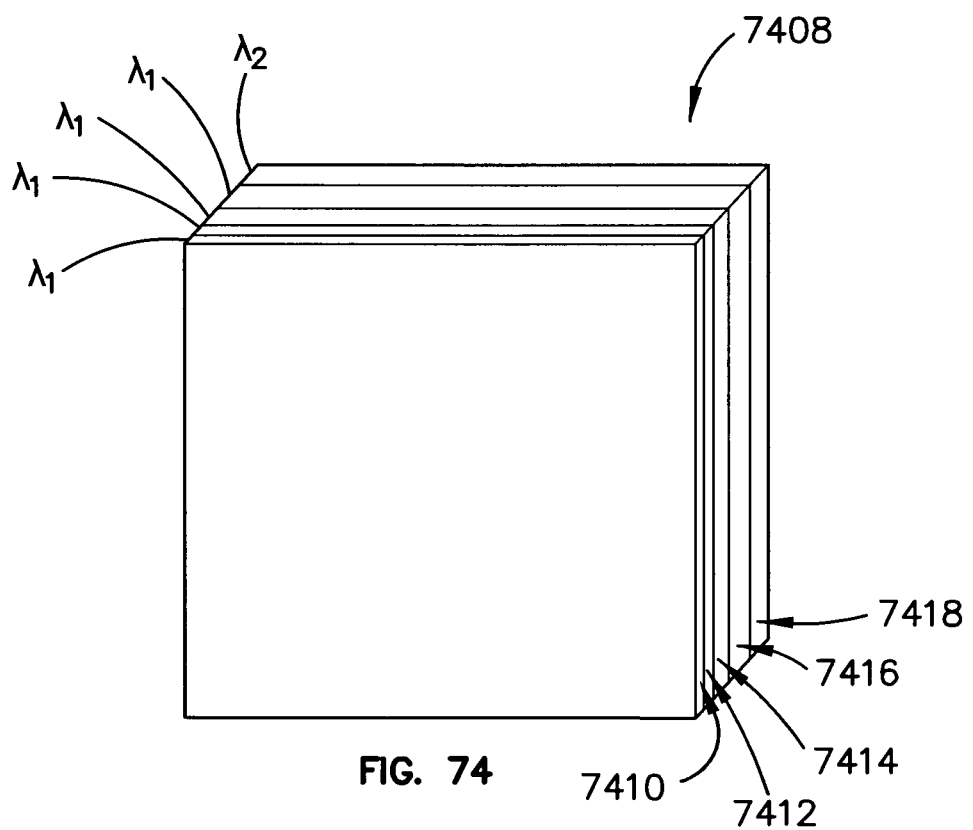

FIG. 74 illustrates a test filter having a more complex structure. This test filter element 7408 is made of five layers 7410 to 7418. Four of the layers 7410 to 7416 attenuate light in wavelength band $\lambda 1$ but are transmissive to all other wavelength bands, and the last layer 6818 absorbs at wavelength band $\lambda 2$.

Figure 75:
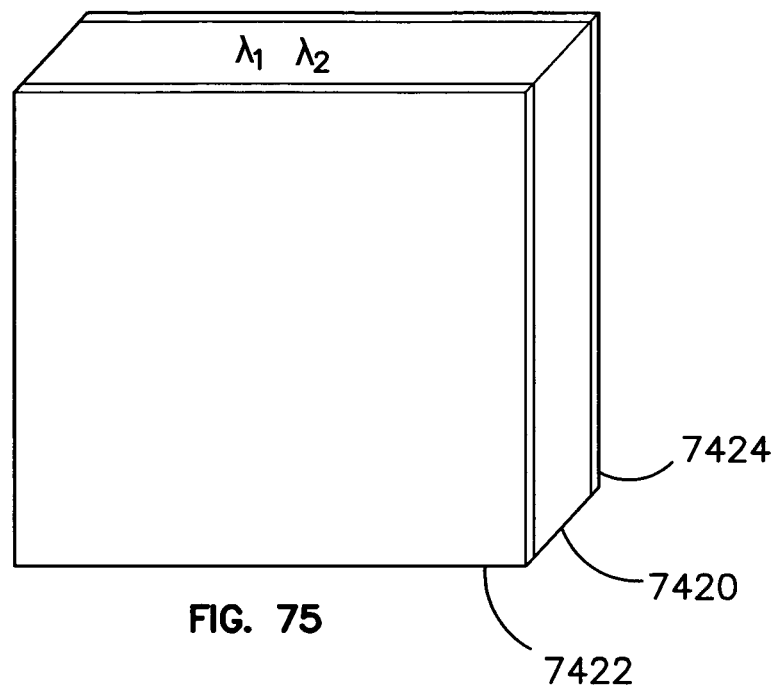

FIG. 75 illustrates another test filter. This test filter has a central portion 7420 which has characteristics chosen to achieve a predetermined attenuation of light in wavelength bands $\lambda 1$ and $\lambda 2$ but it is laminated with transparent layer 7422 and 7424 to protect the attenuating layers forming the core 7420. This can be particularly advantageous where the attenuating layers use a surface treatment which may be damaged by contact with other objects or substances.

In another embodiment one or both of the surfaces of the test filter can be treated with a plurality of thin films to create a predetermined wavelength selective attenuation profile.

Moreover, the filter elements can be reflective rather than absorptive, to achieve the desired attenuation profile.

Figure 76:
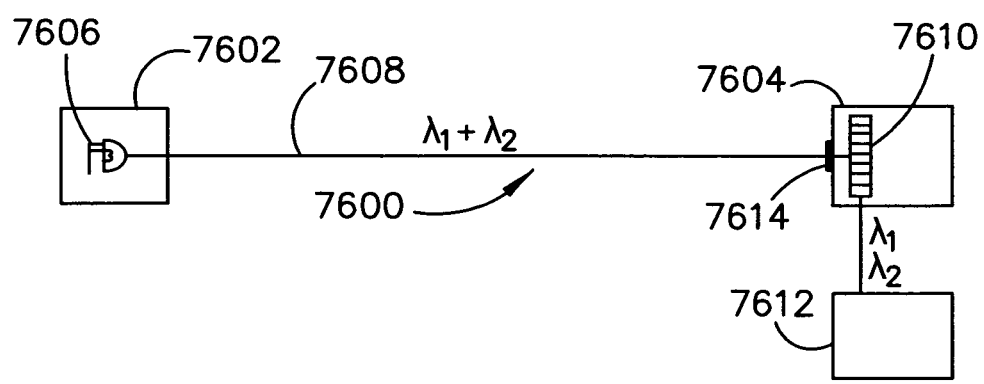
FIG. 76 illustrates schematically a particle detection system made in accordance with an embodiment of the present invention.

FIG. 76 illustrates a beam detector 7600 which includes a transmitter or light source 7602 and receiver 7604. The transmitter 7602 includes one or more light emitters 7606 which are adapted to generate one or more beams of light 7608. At least a portion of the one or more beams are received by the receiver 7604. Preferably, the light emitter 7606 is adapted to simultaneously generate light within two wavelength bands centered at different wavelengths $\lambda_1$ and $\lambda_2$ hereinafter termed "wavelength bands $\lambda_1$ and $\lambda_2$" for transmission to the receiver 7604. The receiver 7604 includes a light sensor 7610 which is adapted to output a signal representing the received light intensity at a plurality of positions on its surface in the two wavelength bands. The output in the two wavelength bands is passed to a controller 7612 which performs analysis on the output of the light receiver 7604 and applies alarm and/or fault logic to determine whether an action needs to be performed in response to the received signal or signals. The receiver 7604 may additionally include optical system 7614 for forming an image or otherwise controlling the received beam 7608.

In an embodiment of the present invention where the light emitter 7606 simultaneously emits in two wavelength bands $\lambda_1$ and $\lambda_2$ the sensor 7610 of the receiver 7604 is preferably adapted to simultaneously and distinguishably receive light in each of the wavelength bands. In order to achieve this aim, the receiver 7604 can be provided with wavelength selective component which is adapted to split light in wavelength band $\lambda_1$ from light and wavelength band $\lambda_2$ and differentially direct them to the sensor 7610 in a manner which enables the two wavelength components to be separately measured.

Figure 77:
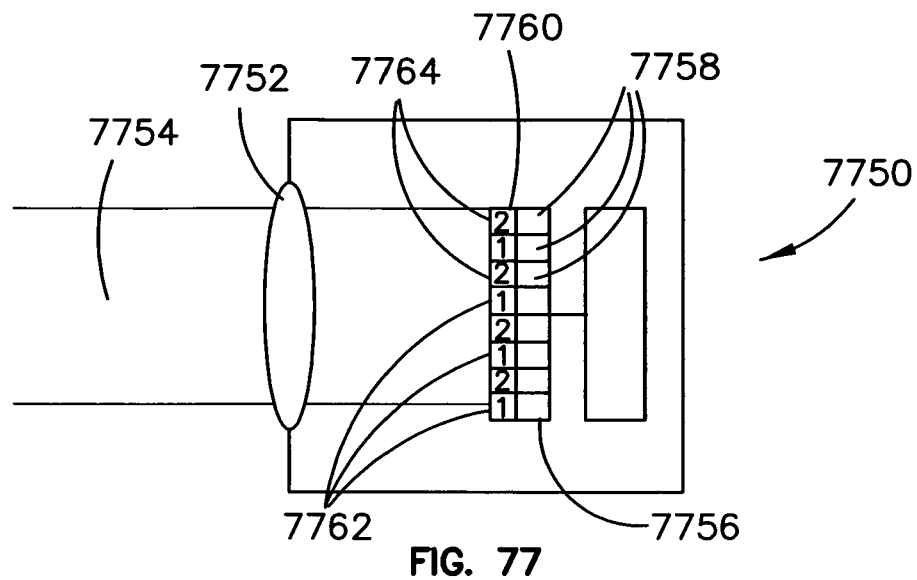
FIG. 77 illustrates an exemplary receiver made in accordance with an embodiment of the present invention.

FIG. 77 illustrates a first example of a receiver 7750 which enables this technique to be performed. The receiver 7750 includes a window 7752 through which a light beam 7754 enters the receiver 7750. The window 7752 may be a flat piece of glass or similar or alternatively may be part of an optical arrangement (e.g. a lens or series of lenses) adapted to form an image on or near the light receiver. The receiver 7750 includes a sensor 7756 which includes a plurality of sensor elements 7758. A wavelength selective component 7760 is mounted adjacent the front face of the light sensor 7756 and comprises for example, a mosaic dye filter. The dye filter 7760 includes a plurality of cells 7762 and 7764. The cells 7762 are adapted to be transmissive in a first wavelength band $\lambda_1$ and the cells 7764 are adapted to be transmissive in a second wavelength band $\lambda_2$. The combination of mosaic dye filter 7760 and light sensor array 7756 enables a first group of sensor elements or pixels of the sensor 7756 to receive light in the first wavelength band whilst other pixels of the sensor array 7756 simultaneously receive and record light intensity use in a second wavelength band $\lambda_2$.

The controller can then be configured to separate the intensity values in one group (i.e. relating to one wavelength band) from the other, e.g. the outputs of the sensor elements can be selectively "read out" to obtain the two wavelength band signals.

Figure 78:
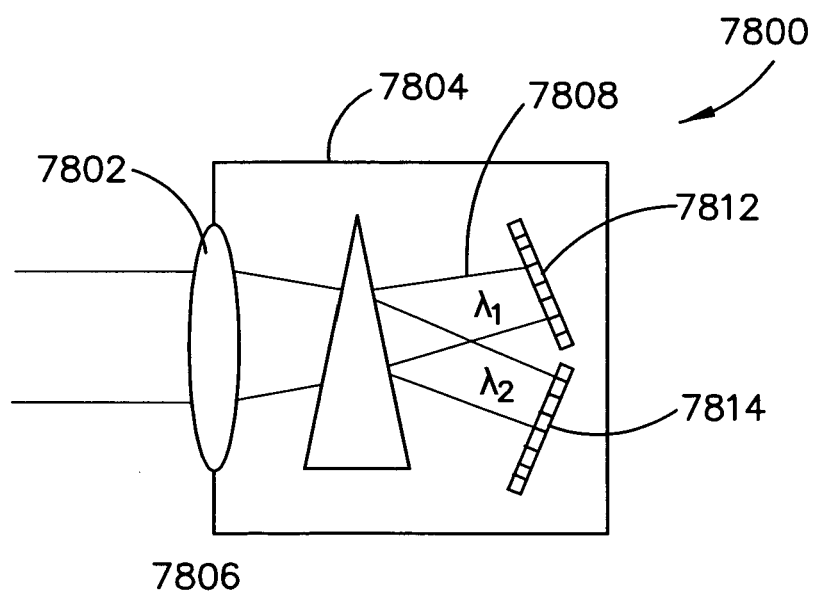
FIG. 78 illustrates a further illustrative embodiment of a light receiver according to the present invention.

FIG. 78 shows an alternative embodiment which achieves a similar result. In this embodiment the receiver 7800 is similar to that of FIG. 77 in that it includes an optical component 7802 which may comprise a window or focusing optics through which light enters the receiver housing 7804. After passing through the optical component 7802 the beam enters a wavelength selective prism 7806 which is adapted to divert light in different directions depending upon the wavelength of the incident light. Accordingly, light in wavelength band $\lambda_1$ is transmitted into a first beam 7808 whereas light in wavelength band $\lambda_2$ is transmitted in a second beam 7810. The beam in wavelength band $\lambda_1$ falls on a first sensor array 7812 and light in the second wavelength band $\lambda_2$ falls on a second sensor array 7814. As previously described in relation to earlier embodiments, the sensor arrays 7812 and 7814 are adapted to record the intensity of light at a plurality of points on its surface simultaneously.

Figure 79:
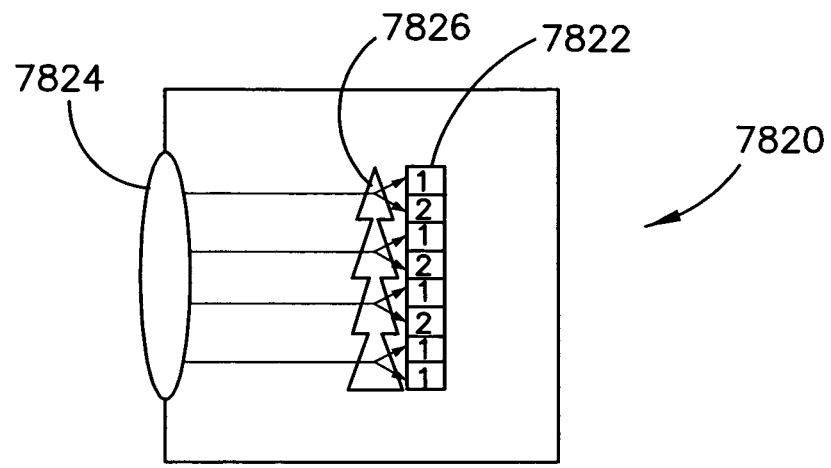
FIG. 79 illustrates a further light receiver made in accordance with an embodiment of the present invention.

FIG. 79 shows a second embodiment using a prism to split a beam into its wavelength components. In this embodiment the receiver 7820 includes a single sensor array 7822 adapted to receive light via an optical component 7824 and a beam splitting component 7826. The beam splitting component is adapted to split light in a first wavelength band from light in a second wavelength band and to direct these in different directions. This embodiment differs to that of FIG. 78 in that rather than forming images in each of the wavelength bands $\lambda_1$ and $\lambda_2$ on separate sensor arrays the beam splitting component 7826 is mounted very close to the sensor array 7822. In this way, as the beam splitting takes place very close to the surface of the sensor array 7822. Effectively, this provides a separate wavelength selective beam splitter for a subset of pixels of the sensor element 7822.

Figure 80:
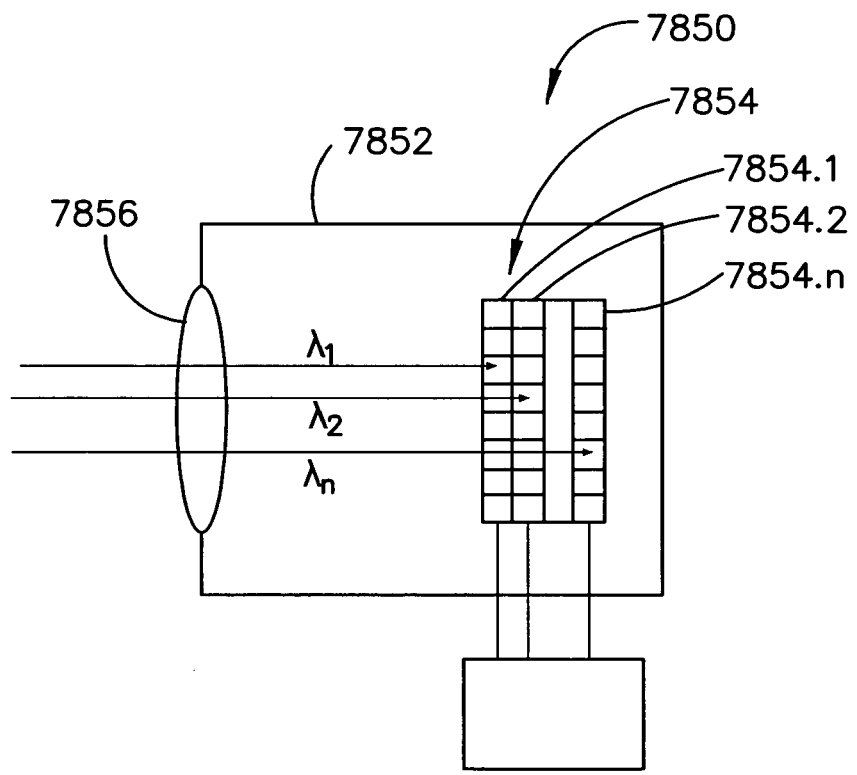
FIG. 80 illustrates a fourth embodiment of the light receiver made in accordance with an embodiment of the present invention.

FIG. 80 illustrates a further embodiment of the present invention. This embodiment illustrates a light receiver 7850 including a housing 7852 in which is mounted a sensor element 7854. Light enters the housing through an optical system 7856 and is transmitted to the light sensor 7854. In this embodiment, the sensor 7854 is a multi-layered sensor and includes n sensor layers 7854.1, 7854.2 through 7854.n. Each sensor layer 7854.1 through 7854.n is adapted to receive light at a different energy. This energy separation is achieved by taking advantage of the phenomenon that different energy photons will penetrate at different depths into the sensor device 7854. In this case the sensor device can be a silicon light sensing element. In each layer of the sensor 7854 a spatially distinct measure of light intensity can be determined at its corresponding wavelength.

In each of the embodiments described above the signals at a plurality of wavelengths can be processed in accordance with the aforementioned methods to produce a particle detection or fault condition output.

It should be appreciated that although the preferred embodiments were described in connection with the two wavelength system, three or more wavelengths may be used in some embodiments.

Figure 81:
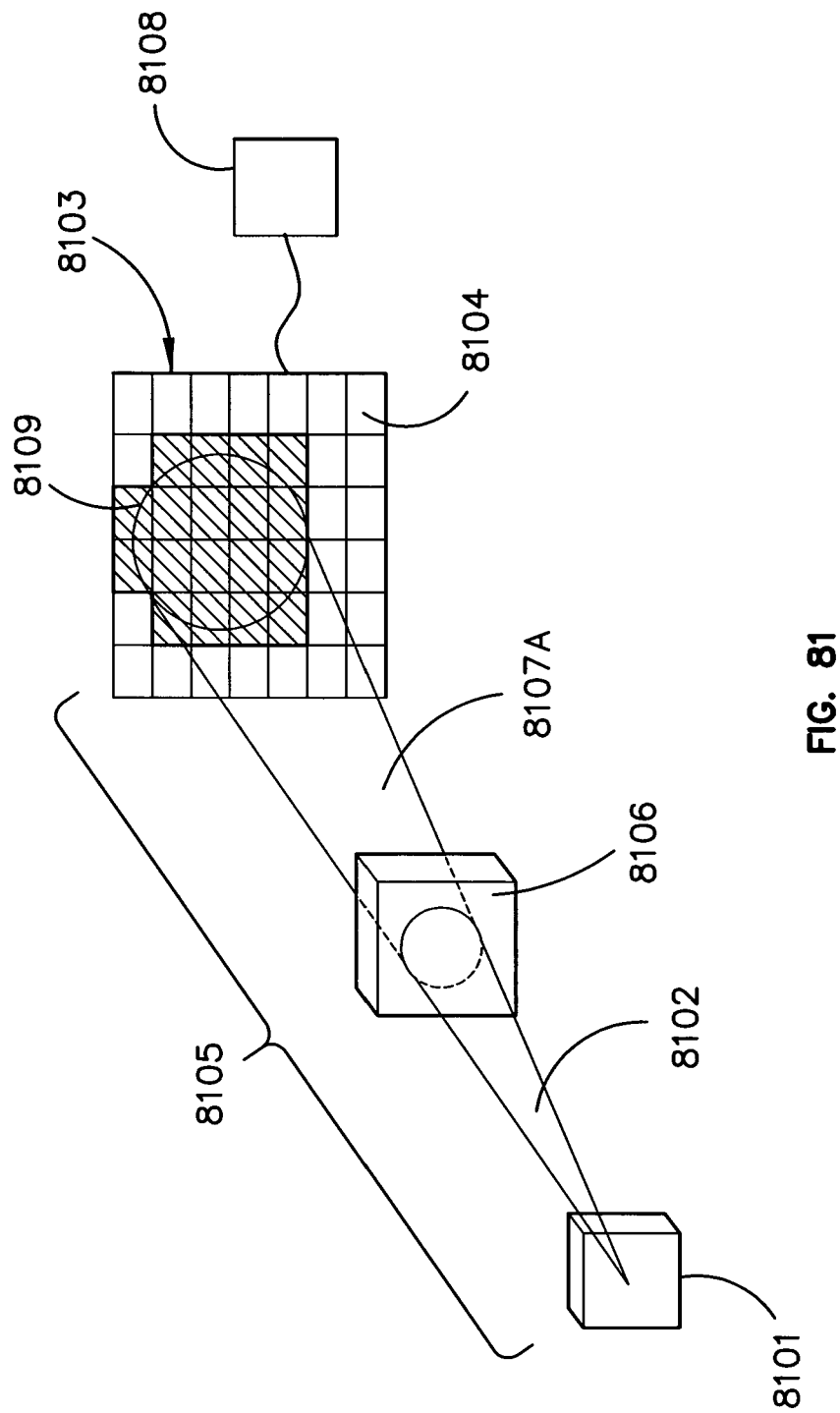
FIG. 81 is a schematic representation of a beam detector that utilises an embodiment of the present invention.
Figure 82:
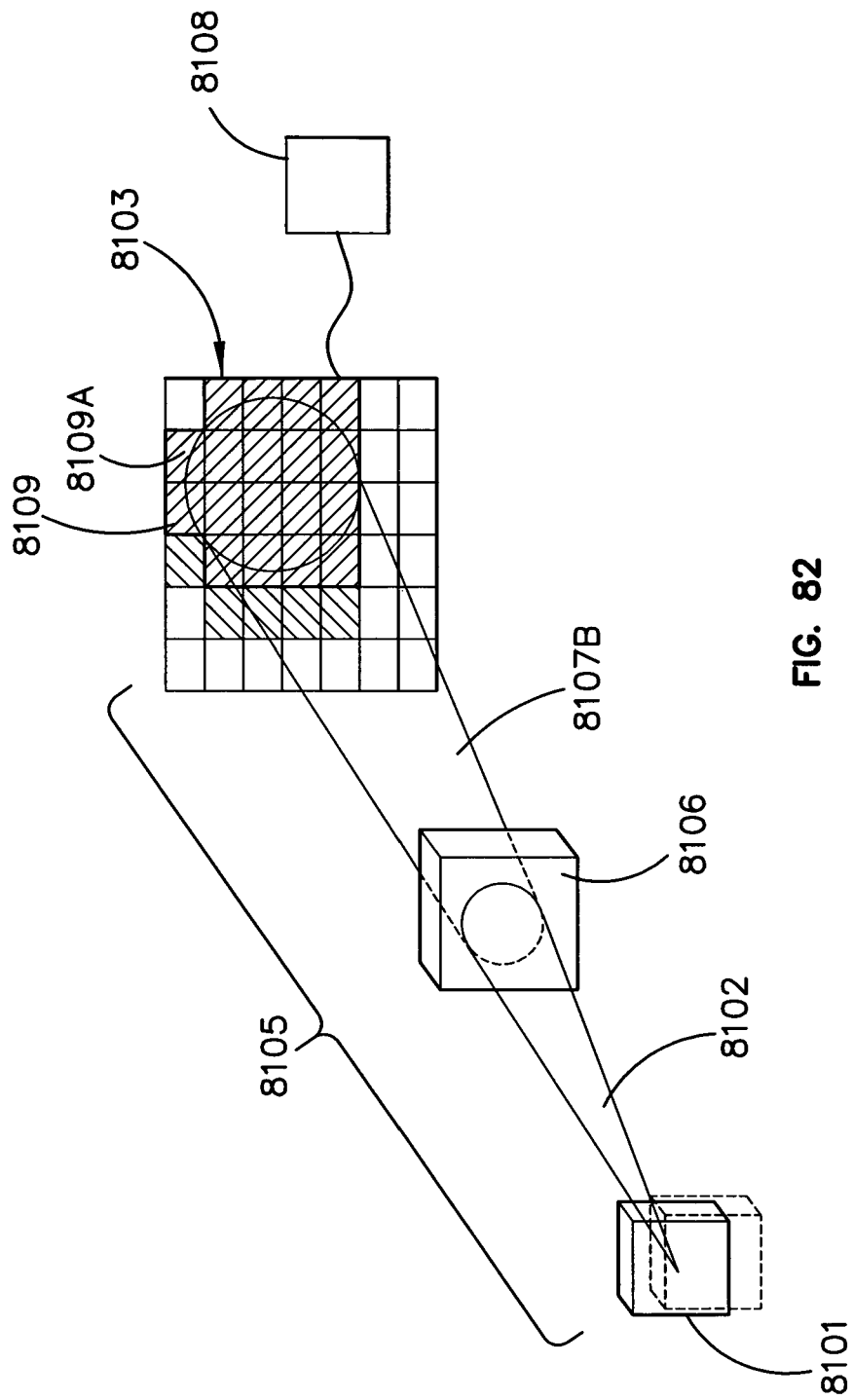
FIG. 82 is a schematic representation of the beam detector represented in FIG. 81, showing a different transmitter position.

FIGS. 81 and 82 show one embodiment of the present invention that includes a transmitter 8101 for emitting at least one beam of light 8102, and a receiver 8103 for receiving the beam. The receiver 8103 has a light sensor having multiple photosensitive elements 8104. An example of a suitable receiver is a video imager whose sensors are arranged into a matrix of pixels. Each sensor element produces an electric signal that is related e.g. proportionally, to the intensity of the light detected by that sensor.

In FIG. 81, the transmitter 8101 is shown as being positioned opposite the receiver 8103 across a monitored space 8105. However it should be understood that the transmitter 8101 can be otherwise located (i.e. not directly aiming the emitted beam toward the receiver 8103) as long as the emitted beam 8102 crosses the monitored space 8105. The emitted beam 8102 can be directed toward the receiver 8103 by an arrangement such as an optical reflector.

A diffusing means 8106 is provided in the path of the emitted beam 8102, so as to produce a deliberately diffused image of the beam on the receiver's sensor 8107A. Signals from the sensor elements 8104 are transmitted to a controller 8108, such as a processor.

The controller 8108 combines the signals from at least some of the sensor elements e.g. only those on which the beam falls, group 8109 to determine the intensity of the received beam 8107A. Each sensor element in the CCD 8103 can have a different inherent noise level, and a different light conversion efficiency. Therefore, in its calculations, the controller 8108 takes into account information regarding the sensor elements 8109A that are initially in alignment with the beam 8107A. Based on the determined intensity, the controller 8108 applies alarm logic and decides whether any action, such as signalling an alarm, or dispatching an alert or a message to an administrator or another user, should be taken. In previously described systems, the decision has been made based on whether the determined intensity is lower than a threshold value that corresponds to a presence of smoke particles.

In FIG. 82, the position of the transmitter 8101 is shown as being slightly removed from its position as shown in FIG. 81. This change results in a change in the position of the diffused beam image 8107B, relative to the receiver 8103. Some of the sensor elements onto which the diffused beam 8107B is incident are outside the initial subgroup of sensor elements 8109 whose signals are initially read by the controller 8108. The controller 8108 is adapted to track the position of the image of the beam across the surface of the sensor 8103 and consequently integrates the received light over sensors in a new region 8109A. As would be appreciated the group of sensors within the region 8109A is different to that which was originally used as group 8109, but the two groups (8109, 8109A) include the same number of sensors.

The sensor elements in the new region 8109A theoretically can have a different inherent signal error than the sensor elements in the original region 8109. However, this difference is not significant. In this example the average inherent noise level of the four newly integrated sensor elements will be about the same as that of the four sensor elements that are no longer used. Moreover, the spacing (i.e. number and size of gaps) between sensor elements remains substantially constant and thus no additional light is lost in the gaps between sensors elements.

This can be contrasted to the case of a sharply focused beam image where the error related to the received beam strength will change dramatically as the sharply focused beam moves from one sensor element to the next because the two sensors have different light conversion efficiencies and the difference is not ameliorated by averaging (as in the case of a more diffused beam image). Further, as the focused beam moves from one sensor element to the next it will scan past the space between the sensor elements, and there will be an intervening period where a substantial amount of the beam power will be lost in the space between the sensors. As described above, these problems are mitigated by use of a defocused image.

The following paragraphs describe examples of how the optics (i.e. imaging system) used in the receiver can be arranged so as to produce a deliberately defocused target. In this specification, the term 'diffusing means' should be read broadly to refer to any arrangement or component that produces a diffused image of the beam on the sensor.

Figure 83:
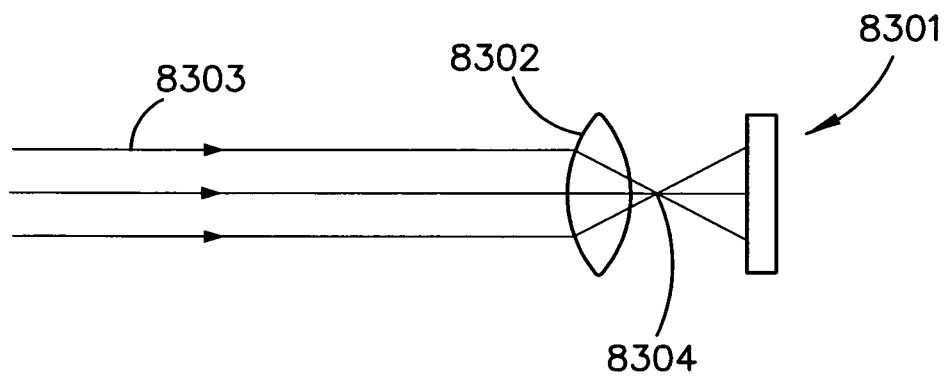
FIG. 83 is a schematic diagram depicting one embodiment of a diffusing means, of an embodiment of the present invention where the transmitter is sufficiently far away that the beam rays entering the lens are essentially parallel.

In the embodiment illustrated in FIG. 83, the diffusing means 8301 includes a focusing lens 8302 that is located in the emitted beam's path.

The focusing lens 8302 has an associated focal point 8304. The emitted beam 8303 is either transmitted directly by the transmitter (not shown) toward the lens 8302 or toward a reflector (not shown) that reflects the beam toward the lens 8302. In this embodiment, the relative positions of the lens 8302 and the sensor 8305 are such that the sensor is displaced from the position where the focused beam image 8306 is located. The sensors 8305 therefore receive a beam image that is deliberately slightly defocused. The amount of focus and the amount of diffusion are controlled so that the signal to noise ratio can be obtained (achieved with a more tightly focused beam) while achieving a system that is relatively stable (achieved with a diffused or blurred image) even when there are movements in the system.

Figure 84:
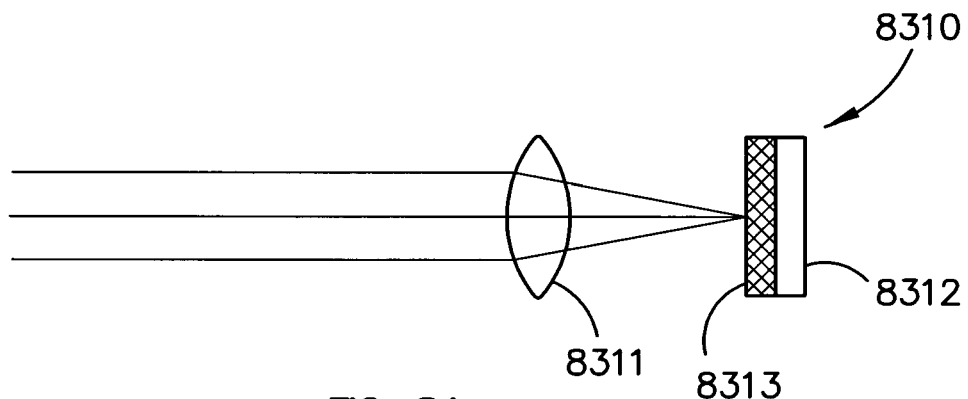
FIG. 84 is a schematic diagram depicting another embodiment of the diffusing means of the present invention.

In a further embodiment (FIG. 84), the receiver 8310 includes a focusing lens 8311. The light sensor 8312 is placed at the spot where the focused image is located. The diffusing means in this embodiment includes a diffuser 8313 that is placed somewhere between the lens 8311 and the light sensor 8312 (e.g. directly over the sensors). The received image is therefore deliberately blurred. The diffuser 8313 can be a piece of ground or etched glass or simply comprise an etched face on the sensor itself.

In some cases, the diffusing means 8313 can be located somewhere in the emitted beam's path to the sensor 8312.

In some embodiments the transmitter may output a light beam having components in two (or more) wavelength bands, for example infrared (IR) and ultraviolet (UV) light bands, both emitted along a substantially collinear path. The two wavelengths are chosen such that they display different behaviour in the presence of particles to be detected, e.g. smoke particles. In this way the relative change in the received light at the two (or more) wavelengths can be used to give an indication of what has caused attenuation of the beam.

In some embodiments, the receiver may receive multiple beams, or multiple transmitters may emit beams to be received. The multiple beams are used together for the purpose of smoke detection in the monitored space. As with the previous embodiments, the sensors receive the beams and send signals to the controller. The controller analyses the signals, and determines which portion of the signals contains information most strongly related to the respective beams. At the conclusion of this decision process, the controller will have selected two portions of signals that are produced by respective individual sensors or groups of sensors, so the selected signal can most reliably be used to measure the intensity of beams. One way of selecting the sensors whose data can be most reliably used is to view the image generated by the receiver at the time of commissioning the smoke detector and selecting the appropriate sensors.

A further mechanism of ensuring that the calculated received beam intensity is as close to the actual intensity of the received beam as possible, may be performed by the controller. The controller may decide whether to use the value corresponding to a certain sensor element, according to that element's contribution to the overall image strength. For example, from the sensor element outputs, the controller can determine a 'centre-of-signal' position of the beam. The centre-of-signal position is analogous to the centre of mass position, except that instead of mass, it is the signal value contributed by each pixel (i.e. sensor element) that is used in the calculation. For example, the following equation may be used:

Centre-of-signal position vector={sum of (position vector of each pixel)*(value of each pixel)}/{sum of values from all the pixels}.

After the centre-of-signal position is determined, the controller may weight the signal contributed to the received beam intensity value by each sensor element (i.e. corresponding to the electrical signal generated by each sensor) according to the distance between that sensor element and the centre-ofsignal position. In this way, the controller determines the sensor elements whose signals best represent the target image and that are least likely to be dropped from subsequent measurements due to drift in the beam image's position on the sensor.

Figure 85:
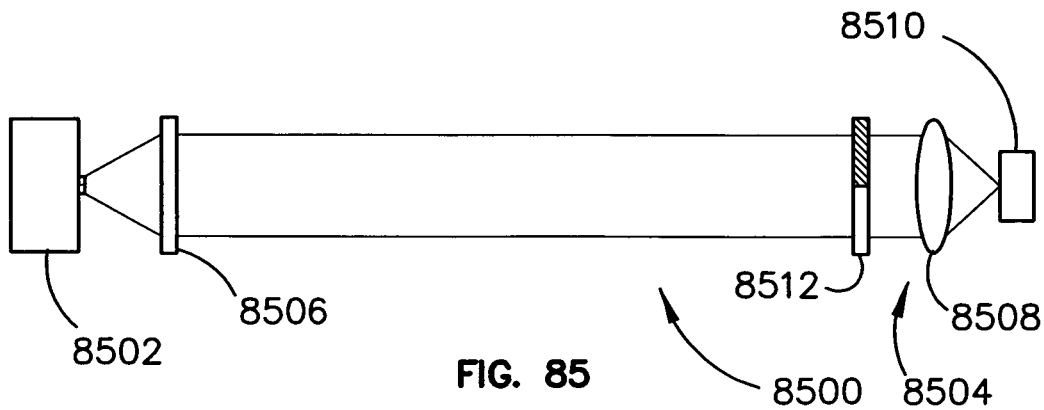
FIG. 85 illustrates a further embodiment of an aspect of the present invention.
Figure 86:
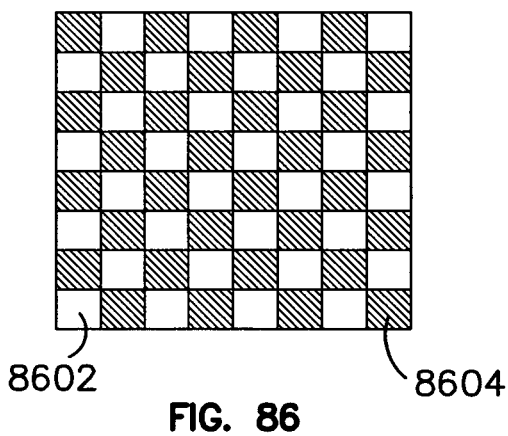
FIGS. 86 through 89 illustrate multiple wavelength filter arrangements which are able to be used in an embodiment of the present invention, such as that illustrated in FIG. 85.
Figure 87:
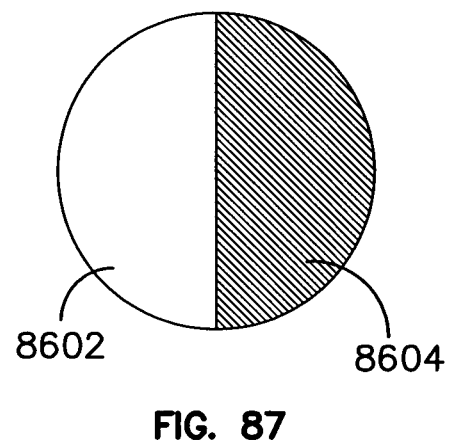

FIG. 85 illustrates an embodiment of a further aspect of the present invention. In this embodiment, the particle detection system 8500 includes a transmitter 8502 and a receiver 8504. The transmitter 8502 includes a light source or light sources adapted to emit light including light into wavelength bands $\lambda_1$ and $\lambda_2$. The light source 8502 can include a plurality of light emitting elements each adapted to emit in a different wavelength band, or a wide band light source. The transmitter 8502 can additionally include one or more optical components e.g. 8506 for forming a beam of light of desired beam profile or dispersion characteristics. The receiver 8504 can also include a light directing or image forming optics 8508 which are adapted to form an image of the beam on a sensor array 8510 of the receiver 8504. In order to minimise the interference of ambient light with the receiver 8504 the receiver 8504 is also provided with a multiple passband filter arrangement 8512. For example, the multiple passband filter can be an interference filter which is arranged to selectively transmit light of the first passband and second passband corresponding to emission bands of the light source 8502. Most preferably, the filter arrangement 8512 is a multiple passband interference filter which has a passband at a long wavelength and one or more harmonics of that wavelength. In such an embodiment, the light source 8502 must be configured to emit light at similarly related harmonics. For example, a single interference filter can be designed to transmit substantially all light at 800 nanometers and also at 400 nanometers while blocking a large majority of light at other wavelengths. When using such a filter the light source can be adapted to emit at 800 nanometers and 400 nanometers.

Figure 88:
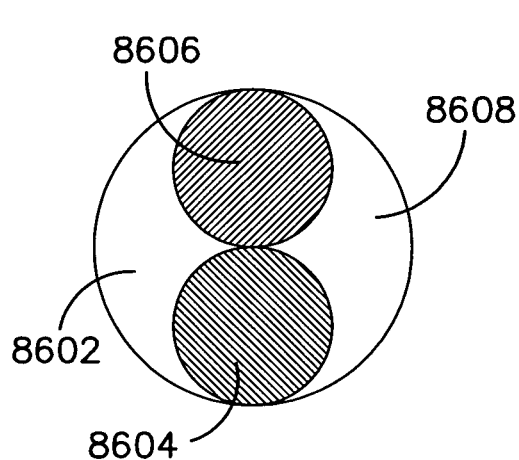
Figure 89:
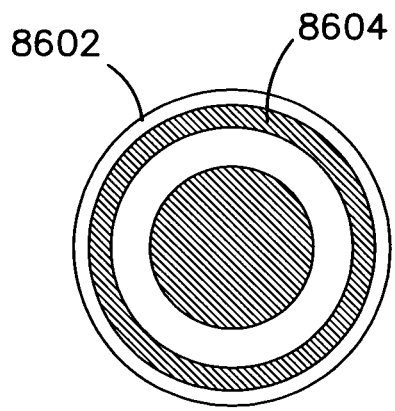

In a further embodiment of the present invention the filter arrangement 8512 can include more than one interference filter or dye filter or other similar type of filter used in parallel. For example, two, or more filters, corresponding to the number of wavelength bands in which the system is configured to operate, may be placed in side by side relationship in the imaging path of the receiver. FIGS. 86 to 89 illustrate examples of such filter arrangements. In this regard, the filter arrangements of FIGS. 86 to 89 include portions adapted to transmit light in a first passband indicated by reference symbol 8602 and shaded white, and alternate portions shaded grey and indicated with reference numeral 8604, which are adapted to transmit light in a second passband. FIG. 88 is adapted for use in a four wave length system and therefore additionally includes portions indicated with reference numeral 8606 and 8608 which are adapted to transmit light in a third and fourth wavelength bands. In each of the filter arrangements, the surface of the filter is approximately equally divided between the different wavelength components and thus transmit substantially even amounts of light in each wavelength band to the receiver. Such an arrangement has a disadvantage compared to the abovementioned multiple passband filter arrangement in that the effective receiver lens diameter is reduced e.g. by approximately one half for each wavelength in FIGS. 86, 87 and 89, thus reducing the effective signal strength. However this is to some extent compensated for by the fact that the light source LED need not be at harmonics of each other but can be selected on other merits such as cost of goods. Moreover, the filters used in such an arrangement may be of lower cost and not require such accurate wavelengths centring and therefore will not be so sensitive to variations in transmitter output with temperature fluctuation.

Figure 90:
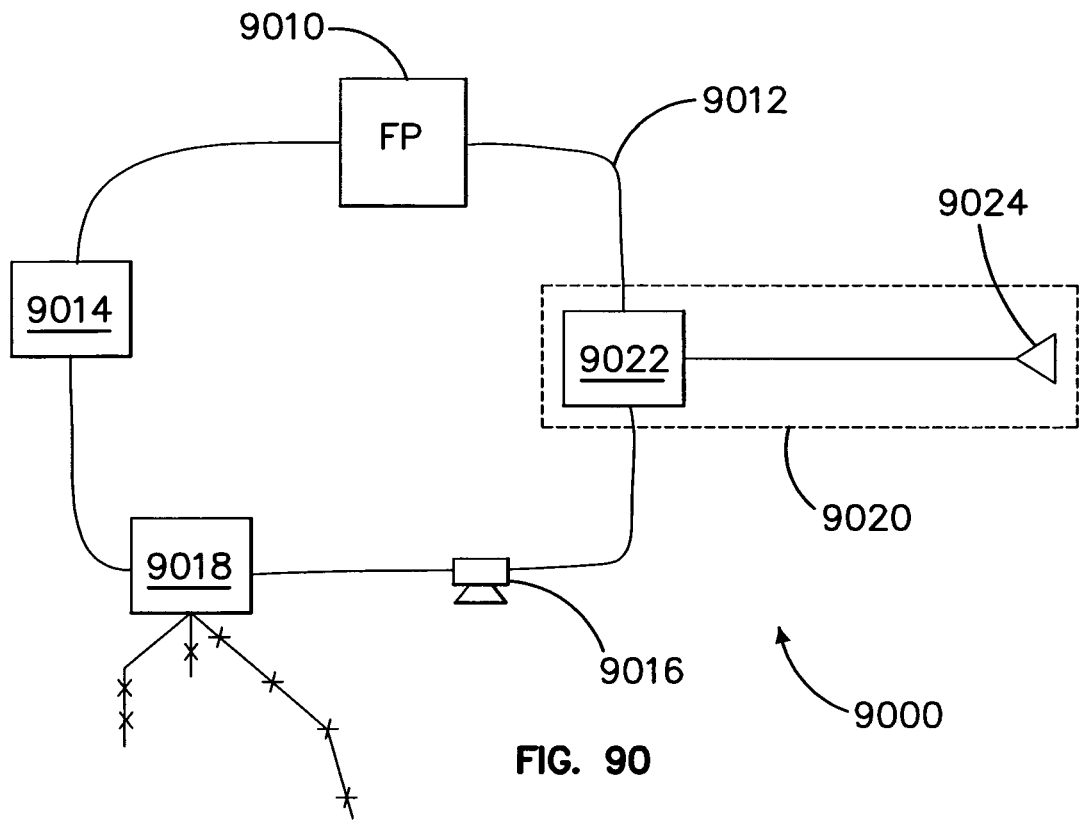
FIG. 90 is a schematic illustration of a fire alarm system which may be adapted to operate in accordance with an embodiment of the present invention.

FIG. 90 illustrates a schematic representation of a fire alarm system in which an embodiment of the present invention can be used. The fire alarm system 9000 includes a fire panel 9010 to which is connected a fire alarm loop 9012. The fire alarm loop 9012 delivers power and communication from the fire panel to various pieces of fire alarm equipment attached to the system 9000. For example, the fire alarm loop 9012 can be used to communicate with, and power, one or more point detectors 9014 and alarm sirens 9016. It can also be used to communicate with one or more aspirated particle detectors such as detector 9018. Additionally, a beam detector system 9020 can also be attached to the fire alarm loop 9012. In the present invention the beam detector system 9020 can be of the type described above in relation to any of the embodiments herein and include a receiver 9022 at a first end and at a transmitter 9024 located remotely to the receiver. Preferably, the transmitter 9024 is a battery powered device and does not require power to be drawn from the fire alarm loop 9012. Alternatively, it can be powered e.g. off separate mains power or loop. The receiver 9022 is connected to the fire alarm loop 9012 and draws power from the loop and communicates with the fire panel 9010 via the loop. The means of communication will be known to those skilled in the art and allow the beam detector 9020 to indicate a fire or fault condition or other condition back to the fire panel 9010.

The present inventors have realised that since smoke detectors do not need to respond instantaneously, acceptable average power consumption could be obtained by activating the video capture and/or video processing subsystems of the smoke detector intermittently, interspersed with periods when processing and capture is suspended. Thus the system can enter a "freeze" state in which it is designed to consume very little or no power.

A first way of achieving this solution is to provide the video processing subsystem of the particle detector with a simple timer unit which operates to activate the video capture and processing subsystems intermittently.

However, in the preferred form of the system the transmitter 9024 is not powered from the loop or other mains power, but is battery powered and is preferably not connected to the receiver 9022 or in high speed communication with it. Consequently the transmitter 9024 must emit light at only very low duty cycle to conserve power. In such a system the timing of each transmitted burst of light may neither, be controlled by the receiver or synchronised with any other receiver which may also be communicating with the same transmitter 9022.

Furthermore, during the video processor "freeze" period the receiver 9022 may still be required to manage other functions such as servicing polls from the fire alarm loop, or blinking display LEDs or the like. Therefore, using a simple timer mechanism to activate the system processor and awake it from its "freeze" state is not the preferred solution to this problem.

In a preferred form of the present invention the receiver 9022 employs a secondary processor, having much lower power consumption than primary processor, which is used to activate the primary processor and to deal with other functions that must continue without interruption when the primary processor is in its "freeze" state.

Figure 91:
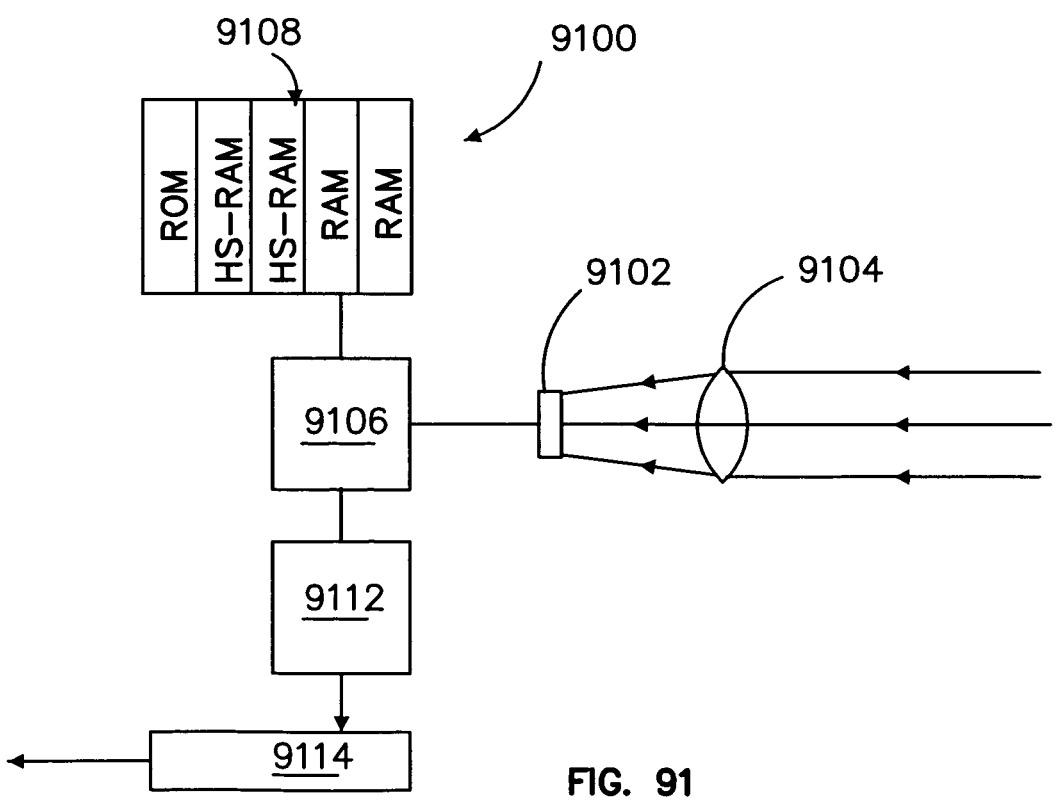
FIG. 91 illustrates a schematic block diagram of a receiver component of beam detector according to an embodiment of the present invention.

FIG. 91 illustrates a schematic block diagram of a receiver 9100 embodying this aspect of the present invention.

The receiver 9100 includes an imaging chip 9102, e.g., a CMOS sensor manufactured by Aptina Inc, part number MT9V034, for receiving optical signals from a transmitter 9024.

It may optionally include an optical system 9104 e.g. a focusing lens, such as a standard 4.5 mm, f1.4 c-mount lens, for focusing the received electro magnetic radiation onto the imaging chip in the desired manner.

The imaging chip 9102 is in data communication with a controller 9106 which preferably is an Actel M1AGL600-V2 field programmable gate array (FPGA), and an associated memory 9108 including a PC28F256P33 flash ROM for program storage, two IS61LV51216 high-speed RAMs for image storage and two CY621777DV30L RAMs for program execution and data storage. The controller's function is to control the image chip 9102 and perform the required sequence of data manipulations to carry out the functions required by the detection system. The control means has sundry additional components as required for correct operation as well understood by those skilled in digital electronics design.

A second processor 9112 is also provided. This processor 9112 can be a Texas Instruments MSP430F2122 microcontroller or similar, and performs functions such as checking the health of the control means and if needed signalling fault to external monitoring equipment if the control means fails or if the control means, for any other reason, cannot perform its required tasks. It is also responsible for the timely control of power to the control and imaging means in order to minimize power consumption. This is performed by processor 9112 de-activating the main processor 9106 when it is not needed and waking it up intermittently when it is required.

Processor 9112 is also in data communication with interface means 9114 such as a display or user interlace and is also connected to the fire alarm loop to enable data communication with other equipment connected to the fire alarm loop e.g. a fire panel.

In the preferred embodiment the interface 9114 means is used to notify external monitoring equipment if an alarm or fault condition exists. If it is determined by the receiver that a fault exists, the interface means notifies this to the monitoring equipment (e.g. fire panel 9010 of FIG. 3) by opening a switch thereby interrupting the current flow out of the aforementioned monitoring equipment. In the preferred embodiment the switch is a solid state arrangement employing MOSFET transistors which has the benefit of being activated and deactivated with very low power consumption. If it is determined by the receiver that an alarm condition exists, the interface means notifies this to the monitoring equipment by drawing current in excess of a predetermined threshold value from the monitoring equipment. In the preferred embodiment the excess current draw is achieved by the positioning of a bipolar-transistor, current-limited shunt across the interface wires from the monitoring equipment. A total current draw of approximately 50 mA is used to signal the alarm condition. In the preferred embodiment, power for normal operation is drawn from the connecting wires to the monitoring equipment at a constant current of 3 mA under non-alarm conditions.

In the preferred embodiment of the present invention the transmitter 9024 includes a controller to control its illumination pattern, illumination time, sequence and intensity for each of the light sources, e.g. infrared and ultra-violet. For example this could be a Texas Instruments MSP430F2122 microcontroller. The microcontroller also detects activation of the device when first installed. In the preferred embodiment of the transmitter, the power source is a Lithium Thionyl Chloride battery.

In a preferred form of the present invention, during commissioning of the system the main processor 9106 can be programmed to discover the illumination pattern of each of the light sources (eg light source 9024 of FIG. 3) and over a period of preferably several minutes e.g. 10 minutes, determine its activation pattern. This process can be repeated for all light sources associated with the receiver. The low power processor 9112 can use the discovered light source sequencing information to activate the primary processor 9106 at the correct time.

As will be appreciated, by using a system of this structure the function of the system which must operate at all times can be controlled by the very low power consumption processor 9112 whilst the highly intensive processing can be performed intermittently by the main video processor 9106, and in doing so the average power can be maintained at a relatively low level.

The inventors have determined that, there are various and often competing constraints associated with practical embodiments that must be dealt with when choosing the illumination pattern of the transmitter and corresponding receiver operation to accurately acquire and track a transmitter output. For example, in some systems it is desirable to use the rate of change of attenuation to distinguish fault conditions from particulate detection events. This complicates the use of long integration times discussed in the background. The preferred embodiment uses an integration period of 10 seconds for normal measurements, and a shorter integration period of one second is used for rate of change based fault detection.

Another constraint on system performance is the scene lighting level. For a practical system it is usually necessary to assume the scene may be lit by sunlight for at least part of its operational life. There may also be limitations on the ability to use wavelength selective filters on the camera (e.g. at least cost limitations). Therefore. it will be necessary to use short exposures to avoid saturation, and still leave sufficient head room for the signal. In preferred implementations of the system the exposure duration is 100 μs, but the optimum value will depend on the choice of sensor, filter, lens, worst case scene lighting and the amount of headroom required for the signal.

A means of synchronising the receiver with the transmitter is also required. It is preferable to achieve this without the use of additional hardware such as a radio system. Instead in one desirable implementation the synchronisation is performed optically using the same imaging and processing hardware that is used for particle detection. However, as a person skilled in the art will appreciate, the use of the same hardware for particle detection as for synchronisation links two concerns within the system, an thereby imposes a further constraint on the possible solutions.

Another constraint within the system is due to the presence of noise. The prime noise sources in the system are camera shot noise and noise from light variations in the scene. Dark noise is generally not a significant contribution for systems that must deal with full sunlight. Scene noise is dealt with very effectively by the background subtraction method described in our earlier patent applications. Shot noise cannot be totally removed, as it is fundamental to the quantum detection process. However, shot noise can be reduced by reducing exposure time, and also by summing fewer exposures. In the preferred embodiment, substantially all transmitter power is put into very brief flashes, with a repetition rate that still allows an adequate system response time.

For example, a flash rate of 1 per second will satisfy the response time requirement, and a flash duration of less than 1 μs and an exposure time of 2 μs could (in principle) be used. In practice this would be very difficult to synchronise. In addition, the transmitter LEDs would need to handle a very high peak current to deliver the energy in such a short time, which in turn would increase cost. Another limitation is the dynamic range of the sensor. Putting all the power into one flash per second could result in saturation in the sensor.

In consideration of the above factors the preferred embodiment uses an exposure of 100 μs, a flash duration of 50 μs, and a period of 9000 ms. An integration length of 3 samples is used for rate of change based fault detection. An integration length of 30 samples is used for smoke measurements.

To perform the background cancellation techniques, the receiver also needs to capture images just before and just after the flash that are used to eliminate the contribution from the scene. Ideally these "off" exposures would occur as close to the "on" exposure as possible to optimise cancellation in the case of a time varying background. With the receiver system used in the preferred implementation, the maximum practical frame rate is 1000 fps, so the "off" exposures are spaced 1 ms either side of the "on" exposure.

Figure 92:
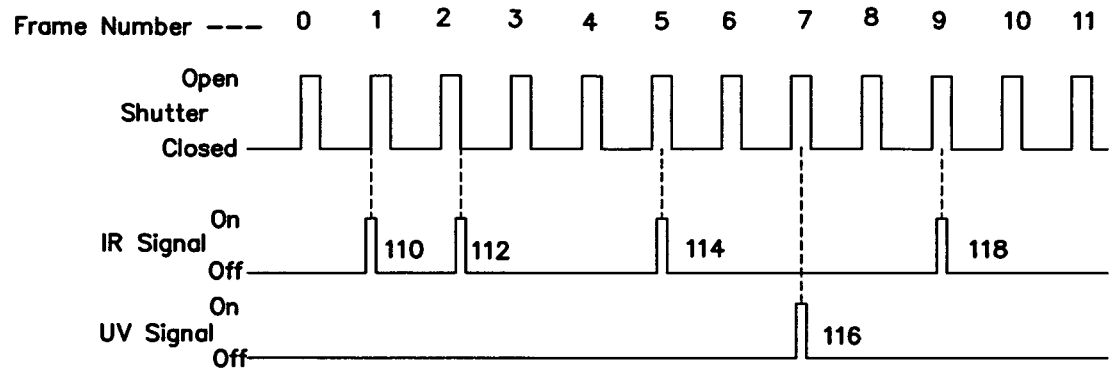
FIG. 92 illustrates an exemplary pulse train used in an embodiment of the present invention.

In one form, the transmitter optical output consists of a series of short pulses, with a very low duty cycle. The pulses are placed to match the frame rate of the imaging system (e.g. 1000 fps). FIG. 92 shows an exemplary pulse sequence in relation to the sensor exposures in the receiver. In this case the transmitter is adapted to emit light in an IR wavelength band and an μv wavelength band. This series of pulses is repeated with a period of 9000 ms.

In the example, there are 5 pulses, as follows:

Sync 1 (frame 1) 110 and Sync 2 (frame 2) 112: Sync pulses are used to maintain synchronisation (discussed more fully later) between the transmitter and receiver. These are pulses are preferably made in the wavelength band which is most power efficient. In this case the IR light source is used because it results in lower power consumption. Moreover the longer wavelength is more able to penetrate smoke, so synchronisation can be maintained in a greater range of conditions. The Sync pulses are 50 μs long.

Ideally each synch pulse is centred in time on the leading (sync 1) and trailing edges (sync 2) of the receiver's shutter open period. This makes their received intensity vary with small synchronisation errors.

IR (frame 5) 114 and UV (frame 7) 116. The IR and UV pulses are used for signal level measurement (and in turn used to measure attenuation and smoke level). They are 50 μs long, which allows for up to 25 μs timing error between transmitter and receiver without influencing the received intensity.

Data (frame 9) 118: The data pulse is used to transfer a small amount of data to the receiver. The data is encoded by a either transmitting or not transmitting the data pulse. The data pulse has reduced amplitude to save power, and is IR for the same reason. They are 50 μs long. This system provides a 3 bps data channel. The data may include serial number, date of manufacture, total running time, battery status and fault conditions. Those skilled in the art would be aware of many alternative ways to send data in this system. These could include pulse position encoding, pulse width encoding, and multi level encoding schemes. Greater data rates could readily be achieved, however the simple scheme used in the preferred implementation is sufficient for the small amount of data needed.

In FIG. 92, the data from the receiver during "off" frames (i.e. frames with no corresponding transmitter output) are used for the following purposes:

Frame 0 & 3 are used for background cancellation of the sync pulses

Frame 4 & 6 are used for background cancellation of the IR pulse

Frame 6 & 8 are used for background cancellation of the UV pulse

Frame 8 & 10 are used for background cancellation of the Data pulse (a) Spatial Search As described above, the receiver receives each of the transmitted pulses in the form of one or more pixels within an image frame.

However, during commissioning when the system commences operation (at least the first time) the locations of the transmitter(s) within the image frame must be established. This could be performed for example, by a manual process involving an operator inspecting the image, and programming in the co-ordinates. However, the need for special training, special tools, and long complex installation processes for installation is undesirable. In the preferred embodiment determining the location of the transmitters within the image frame is automated. The preformed process for locating transmitters operates as follows:

The system first captures a number of images at a high frame rate and for a time sufficient to ensure that transmitter pulses, if the transmitter is within the field of view of the camera and pulses are transmitted during the period of capture, will be present in one or more images.

The system then subtracts each pair of (temporally) adjacent images, and takes the modulus of each pixel and then tests each against a threshold to detect locations of large variation, at which a transmitter may be present.

The system then condenses the candidate list of transmitter locations by merging candidate points that are adjacent or nearby. (e.g. <3 pixels apart) A centre of gravity method can be used to find the centre of a set of candidate points.

The system then performs a trial synchronisation (using the process described below) at each of the candidate centres to verify that the received value at a candidate centre corresponds to a real transmitter.

The system then checks that the number of transmitters matches the expected number of transmitters. This number may be set by pre-programming the receiver prior to installation, or by a switch or switches mounted on, in, or connected to the receiver unit. In the preferred implementation, there is a set of configuration DIP Switches incorporated into the receiver unit and easily accessible only while the system is not mounted to the wall.

The set of transmitter locations within the image is stored in non-volatile memory. The locations can be cleared by placing the receiver into a particular mode, e.g. by setting the DIP switches to a particular setting and powering/de-powering the receiver, or by the use of a special tool, such as a notebook PC. This is only required if a transmitter is moved from its original location or the system is to be re-installed elsewhere.

Performance limitations in the imaging system may limit the number of pixels or lines that can be read out when operating at a high frame rate. In one implementation, a maximum of 30 lines of 640 pixels can be read out in 1 ms. Therefore the first few steps of the above method need to be repeated 16 times to cover the entire 640*480 image frame. Alternatively, some embodiments employ only part of the image frame. Similarly, some embodiments use a slower frame rate. However, the possibility of sensor saturation in bright lighting conditions generally limits exposure time, and variations in background lighting conditions generally introduce more noise if a lower frame rate is used.

The frame rate must be chosen to ensure that the transmitter pulses do not always occur in period where the shutter is closed. For example, if the frame rate is exactly 1000 fps, with an exposure of 100 us, and the transmitter produces pulses on exact 1 ms boundaries, the pulses may all be generated at times when the shutter is closed. The receiver frame rate is chosen so that there is a slight difference causing a gradual phase shift, ensuring that sooner or later the pulses will fall sufficiently within a shutter open period.

In some embodiments, processing speed limitations are managed by not analysing all of the pixels, instead only every $n^{th}$ (eg. 4th) horizontal and vertical pixel are subtracted and checked, reducing processing effort (eg. by a factor of 16). Provided that the received image i.e. the image of each transmitter on the sensor, is spread over a sufficiently larger area (e.g. a spot having a diameter of 5 pixels), then the transmitter will still be found reliably.

Whenever the system is powered up, either with a known set of transmitter locations or as a part of the Spatial Search described above, with a set of candidate locations, a phase search and lock method is used to establish initial synchronisation.

The major steps of this method are:

The system captures images at a high frame rate (at least a partial image in the expected location).

The system waits for the expected pattern of pulses to appear at the candidate centre locations.

The system uses the time of arrival of a selected pulse within the expected pattern as a starting phase for the phase locked loop.

The system waits for stabilisation of the PLL. If no PLL lock is made, then in the case of testing candidate locations, the location is marked as spurious, otherwise when re-establishing synchronisation with a known transmitter location the receiver can re-try continually and assert a fault until it is successful.

As with the spatial search, a small offset in the receiver frame rate is used to cause a gradual phase shift, ensuring that sooner or later the pulses will fall sufficiently within a shutter open period.

For each frame, the total intensity is calculated within a small region of the image centred on the known or candidate location. This sequence of intensity values is then checked for the expected pattern from the transmitter.

The test for the expected pattern operates as follows:

After at least 9 frame intensity values have been collected, they can be tested for the presence of the expected transmitter pulse sequence in the following manner.

Given the intensity values I(n), 0<n<N,

Test for a possible transmitter signal starting with its frame 0 at frame n received First, compute an "off frame" reference level $I_0 = (I_R(n+0)+I_R(n+3)+I_R(n+4)+I_R(n+6)+I_R(n+8))/5$
{mean of "off frames"}

Compute relative intensities $I_R(n+m) = I(n+m) - I_0$ for $m=0$ to 8

Compare with pre-determined thresholds to determine the presence or absence of a tranmitter pulse in each frame Found={$(I_R(n+1) > I_{ON})$ or $(I_R(n+2) > I_{ON})$} and {Sync 1 or Sync 2 pulse}

$(I_R(n+5) > I_{ON})$ and {IR pulse}

$(I_R(n+7) > I_{ON})$ and {UV pulse}

$(I_R(n+0) < I_{OFF})$ and {off frame}

$(I_R(n+3) < I_{OFF})$ and {off frame}

$(I_R(n+4) < I_{OFF})$ and {off frame}

$(I_R(n+6) < I_{OFF})$ and {off frame}

$(I_R(n+8) < I_{OFF})$ and {off frame}

Due to the random phase errors, either of the sync pulses may be completely missing, hence the "or" in the above expression. Alternatively, the tests for the sync pulses can be omitted entirely, and the tests for the off frames can also be reduced. However, care must be taken to ensure that the position of the transmitter pulse sequence is not falsely identified.

Following a positive detection, the time corresponding to the frame n is recorded in a variable. The amplitudes of the phase pulses can be used to trim the recorded time value to more closely represent the start of the sequence. This helps reduce the initial phase error that the phased locked loop has to deal with, and may not be required if frequency errors are sufficiently small.

In the preferred implementation the image capture rate 1000 fps which matches the transmitter timing as previously described. A shutter time of 1000 is used.

This completes the initial synchronisation. The arrival time of the next set of pulses can now be predicted by simply adding the known transmitter period to the time recorded in the previous step.

Although the transmitter period is known to the receiver (300 ms in the preferred implementation), there will be small errors in the clock frequencies at each end. This will inevitably cause the transmitted pulses to become misaligned with the receiver shutter open time. A Phase Locked Loop system is used to maintain the correct phase or timing. The PLL concept is well known so will not be described in detail. In the preferred implementation the PLL control equations are implemented in software. The Phase Comparator function is based on measuring the amplitude of the phase pulses. These amplitude are calculated by subtracting the mean of the intensities measured in the nearest off frames (frames 0 & 3). The phase error is then computed with the following formula:

$$\varepsilon = \frac{I_R(1) - I_R(2)}{2(I_R(1) + I_R(2))} \cdot T$$

where T is the width of the phase pulses.

In the case that the phase pulse amplitudes fall below a pre-determined threshold, the phase error is assigned a value of zero. This way noisy data is permitted into the PLL, and in practice the system is able to maintain adequate synchronisation for at least a few minutes. Therefore, high smoke levels do not cause a synchronisation failure before an alarm can be signalled. In the case of an obstruction, this feature allows the system to recover rapidly when the blockage is removed.

The PLL control equations include proportional and integral terms. It was not found necessary to use a differential term. In the preferred implementation proportional gain and integrator gains of 0.3 and 0.01 respectively were found to produce acceptable results. In a further variation, the gains can be set to larger values initially, and reduced after the phase error is below a pre-determined threshold, thus reducing overall lock time for a given loop bandwidth.

Phase error below +/−10 μs can be used to indicate phase lock, both for the purpose of verifying a candidate transmitter location and also for allowing normal smoke detection operation to commence.

Figure 93:
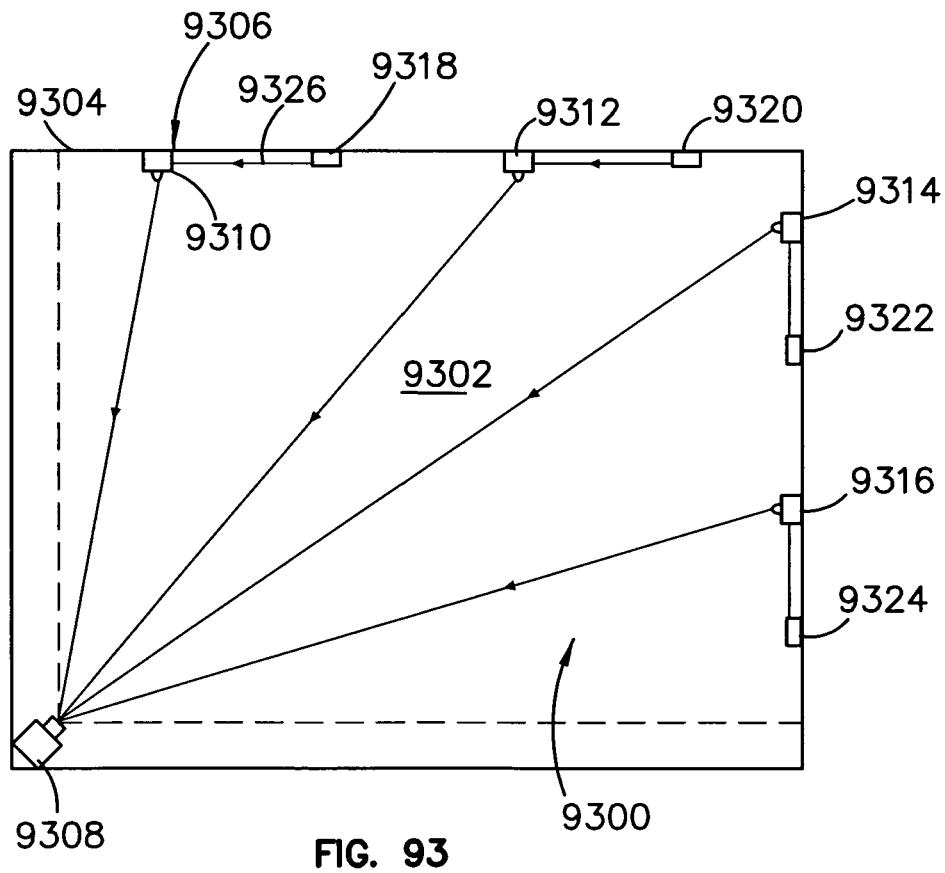
FIG. 93 illustrates schematically an environmental monitoring system in accordance with a first embodiment of the present invention.

FIG. 93 illustrates an environmental monitoring system 9300 adapted to monitor a region 9302 within a room 9304. The environmental monitoring system includes a beam detection subsystem 9306 which includes a receiver 9308 and four transmitters 9310, 9312, 9314, 9316. The beam detection subsystem operates in accordance with an embodiment of any one of the systems described above.

The environmental monitoring system 9300 additionally includes four additional environmental monitors 9318, 9320, 9322, 9324. Each of the additional environmental monitors 9318 to 9324 may be of the same type but alternatively each may be of a different type i.e. sense a different environmental condition or the same condition by a different mechanism. The environmental monitors can include, for example, carbon dioxide, carbon monoxide, temperature, flame, other gas sensors or the like. Each of the additional environmental monitors 9318 to 9324 is connected by a communications channel to a nearby transmitter of the beam detection subsystem. For example, the additional environmental monitor 9318 is connected via wire 9326 to corresponding transmitter 9310 of the beam detection subsystem 9306. Similarly, environmental monitor 9320 is in data communication with transmitter 9312, environmental monitor 9322 is data communication with transmitter 9314 and the environmental monitor 9324 is in data communication with transmitter 9316. The data communications channel between each environmental monitor and its respective transmitter may be hard wired connection or may be via a wireless connection e.g. radio, optical etc. communications link. In most embodiments the communications link need only be unidirectional, however it may in some embodiments be bidirectional. In the unidirectional case, the communications channel is adapted such that the environmental monitor can communicate an alarm and/or fault condition detected by it, or other output, e.g. a raw or processed sensor output to the transmitter of the beam detection subsystem 9606.

As will be appreciated the environmental sensors can be housed within the transmitters rather than located remotely and connected by a long wire or communications link.

The transmitter of the beam detection subsystem 9306 is adapted to receive signals from the environmental monitor and re-transmit these, with or without additional encoding, via an optical communications channel, back to the receiver 9308. The optical communications channel may be implemented by modulating either the particle detection beam or a secondary beam transmitted by the transmitter to the receiver 9308. The communications channel can be alternately or intermittently transmitted between pulses of the particle detection beam generated by the transmitter. Alternatively, it may be continuously illuminated, possibly simultaneously with a particle detection beam. In this case, the wavelength used for the particle detection beam or beams can be different to that on which the optical communications channel is implemented.

Using such a system, a network of environmental monitors may be placed around the region being monitored 9302, and the environmental conditions sensed by these monitors can be communicated back to the receiver of the beam detection subsystem. The receiver 9308 is in data communication with a fire alarm control panel e.g. via a fire alarm loop or proprietary network or other notification system without the need for complicated dedicated wiring system between the environmental monitor network and the fire alarm system. In a preferred embodiment, a plurality of optical communications channels can be differently encoded such that a receiver of the beam detection subsystem can distinguish each optical communications channel from each other. For example, each optical communications channel may be modulated differently or may be scheduled to operate in a different time period. Thus effectively a time division multiplexing arrangement can be implemented for the different optical communications channels. Using different wavelengths for each communications channel may also be possible.

The system also enables the location at which an environmental condition is detected to be determined since the receiver 9308 can resolve optical channels from the different transmitters e.g. based on the signal received or where on the sensor the signal arrives if the receiver's sensor is of a multi-sensor element type. The addressing information or channel information can be passed to the fire alarm control panel and the location of the alert be passed to an operator or fire authority.

In the example of FIG. 93 each of the transmitters and environmental monitors are preferably battery powered to remove any need for wiring.

Figure 94:
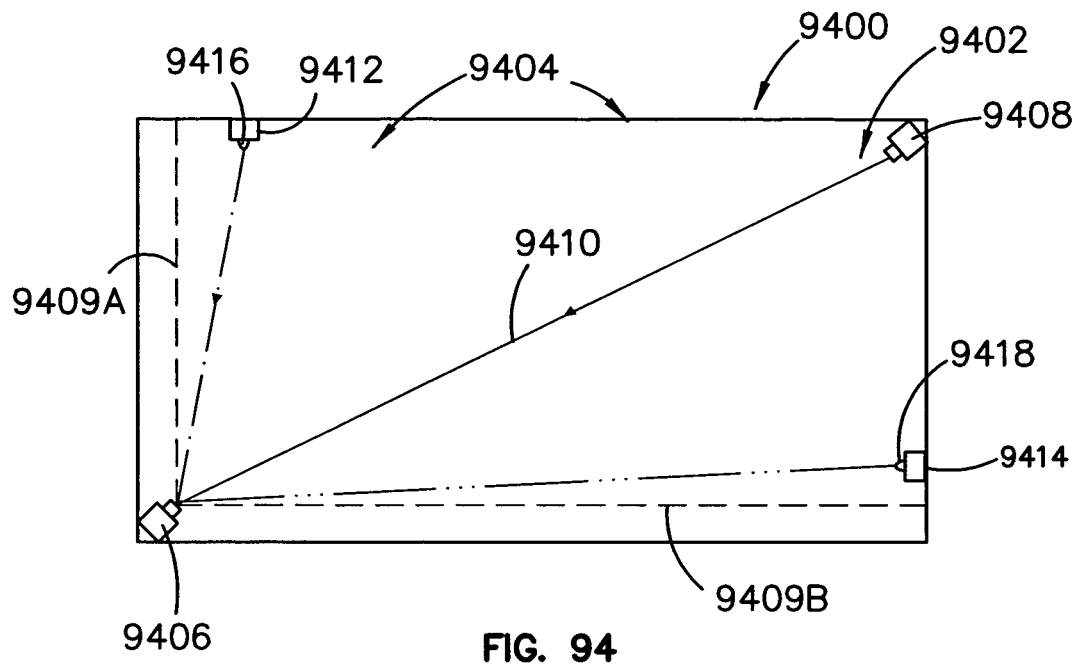
FIG. 94 illustrates a second embodiment of an environmental monitoring system in accordance with a second embodiment of the present invention.

FIG. 94 illustrates a further embodiment of this aspect of the present invention. In this embodiment, the environmental monitoring system 9400 includes a beam detection subsystem 9402 as well as an environmental monitoring subsystem 9404. The beam detection subsystem includes a receiver 9406 and a transmitter 9408. The transmitter is adapted to emit one or more beams of light 9410 which are received by the receiver 9406. The receiver 9406 has a wide field of view having edges indicated by lines 9409, 9409B. Within the field of view of the receiver 9406 there are positioned two environmental monitors 9412, 9414. Environmental monitors 9412 and 9414 may be of any of the types described above, and additionally include a respective light emitter 9416, 9418. The light emitters 9416, 9418 may be a low power LED or the like and are used to generate an optical signal which is received by the receiver 9406. Each of the LEDs 9416, 9418 can be individually modulated to communicate an output of the corresponding environmental monitors 9412, 9414 back to the receiver 9406. As described in the previous embodiment, the optical communications channels can be either time multiplexed or wavelength multiplexed with each other and with the particle detection beam or beams 9410 emitted by the transmitter 9408. This embodiment has the additional advantage over that of FIG. 93 that there is no need for any wiring or communications channel between the environmental monitors 9412 and 9414 and the particle detection subsystem transmitter 9408. Accordingly installation costs are minimised.

Figure 95:
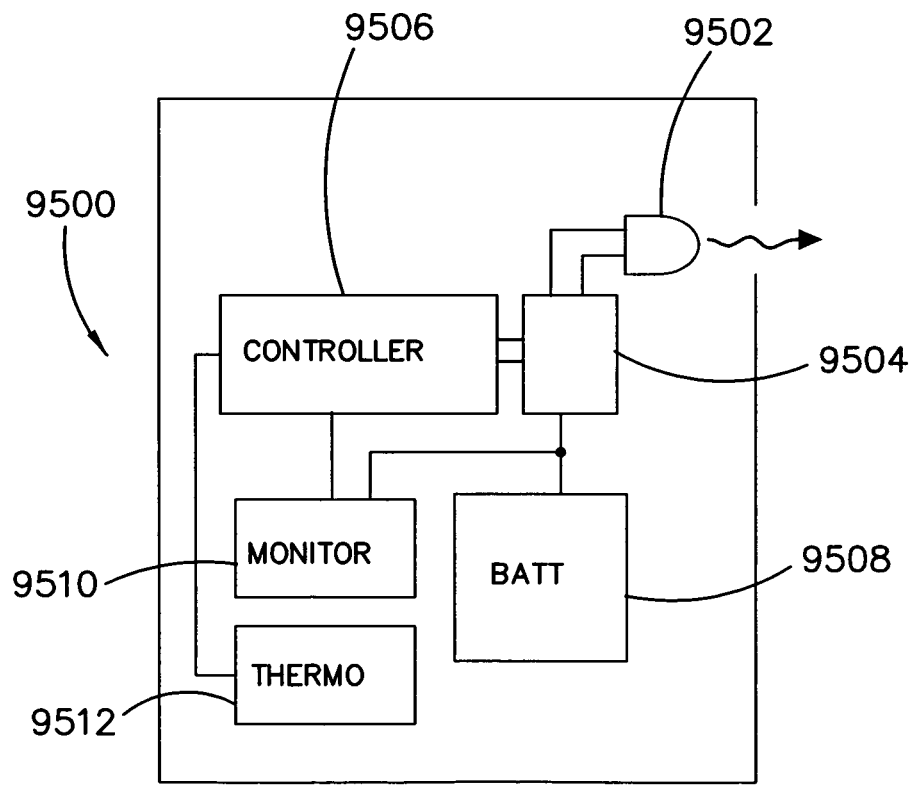
FIG. 95 illustrates schematically a light source able to be used in an embodiment of the present invention.

FIG. 95 illustrates a component of a particle detector system. The component 9500 is a light source which is used to emit one or more beams of light across a volume being monitored for particles. The light source 9500 includes one or more light emitters 9502 which are connected to circuitry 9504 which deliver power to the light emitters 9502. The operation of the light emitter 9502 is controlled by a microcontroller 9506 which causes the light emitters to be illuminated in a predetermined fashion, e.g. to flash in a particular sequence. The light source 9500 is powered by a battery 9508. The output of the battery is monitored by monitoring component 9510 and the environmental conditions in which the component is operating are monitored by the environmental monitor 9512. The environmental monitor 9512 can be a temperature sensing device such as a thermocouple. The controller 9506 receives the output of the battery monitor 9510 and the output of the environmental sensor 9512 and determines an expected battery life.

More particularly, the controller receives signal representing the temperature of the immediate surroundings of the battery and the measured output voltage of the battery 9508. The battery output voltage is compared to a threshold voltage corresponding to the measured temperature and the discharge state of the battery 9508 is determined.

In an alternative embodiment, the battery monitor 9510 is adapted to measure the total current drawn from the battery. For example, the monitor 9510 can be an ammeter and determine the level of current being drawn from the battery. In this case, the controller is adapted to integrate the measured current over time and the remaining available charge is determined. When the remaining charge available is calculated to fall below the predetermined threshold an indication can be generated of the impending discharged state of the battery.

In a further alternative, an estimate of the total current used can be made. For example, in a preferred embodiment the majority of the charge drawn from the battery will be drawn in pulses which are used for flashing the light emitters 9502. If the circuitry 9504 operates at a constant current, which is preferred, the duration of operation of the LED multiplied by this constant current will provide a relatively accurate measurement of the total charge used by the system over time. In a cruder alternative the typical average current consumption known to be required by the equipment can be pre-calculated and the length of time of operation of the component can be used to determine the total current drawn from the battery over time.

In the above embodiments, the environmental conditions, most advantageously the temperature of the immediate surroundings of the battery can be monitored over time and this temperature data can be used by the controller to produce a more accurate estimate of the remaining charge available in the battery 9808. As will be appreciated the controller can be adapted to calculate an estimate of the remaining battery life available under the prevailing conditions. The remaining time can be compared to a warning threshold and if the threshold is exceeded an indication of an approaching discharged state can be generated.

In a preferred embodiment the predetermined time threshold at which an indication of an approaching discharged state of the battery will be generated, may be selected in order to allow maintenance personnel to receive an indication of the impending discharge of the battery during a scheduled maintenance event. If the warning of the impending discharge of the battery can be given at a sufficiently early stage, say before the scheduled maintenance event prior to another scheduled maintenance event at which the battery will need to be changed then no extra unscheduled maintenance event will be required. Moreover, the maintenance personnel can ensure that the required equipment e.g. specialised tools and a battery is obtained prior to the maintenance event at which the battery will need to be changed. For example, where a component has a nominal battery life of 5 years and an annual maintenance inspection is scheduled, an indication of impending battery failure can be raised say 13 or 14 months before the nominal end of life. In this way at the inspection arising about 4 years after commissioning of the system the maintenance personnel will detect that the battery will need to be changed at the following maintenance session (in a year's time) and can plan to bring a replacement battery on the next annual visit. It should be understood that to avoid failure of the system the nominal battery life is set with a significant safety margin. The time of 13 or 14 months is chosen to allow a scheduling margin for the two maintenance sessions i.e. the one at which the maintenance personnel learns of the battery discharge state, and the next one at which it will be changed.

In a preferred form of the present invention, when the component being monitored is a light source of the particle detector, the light source controller can be adapted to signal the battery state to the receiver. This can be done by modulating the amplitude, duration and/or timing of one or more transmitted light pulses in a predetermined fashion. The light pulse used for data transmission can be one of the light pulses used in particle detection or an additional light pulse added to the sequence of light pulses produced by the light source for the purposes of data communication from the light source to the receiver. As described above, such a scheme avoids the need for wiring between the units. Alternatively, the light source may be fitted with additional low powered LED which can be flashed to indicate to a person (rather than the receiver) located remotely from it, the state of its battery.

In a particularly sophisticated embodiment, the controller of the light source can be adapted to generate a battery output signal e.g. by modulating a light beam in a particular code, with which indicates a time until expected a battery discharge. For example, the output signal can indicate the number of months until the battery is expected to be flat. This allows the maintenance personnel to more accurately schedule the next scheduled maintenance session, and also determine if the battery will need to be replaced before the next scheduled visit. Moreover if an accurate 'time to full discharge' is known then the light source can go into a low power mode e.g. in which its duty cycle is reduced from normal to extend battery life. The receiver can be programmed to detect this low duty cycle mode and indicate a fault if a low duty cycle modulation patterns is observed.

Figure 96:
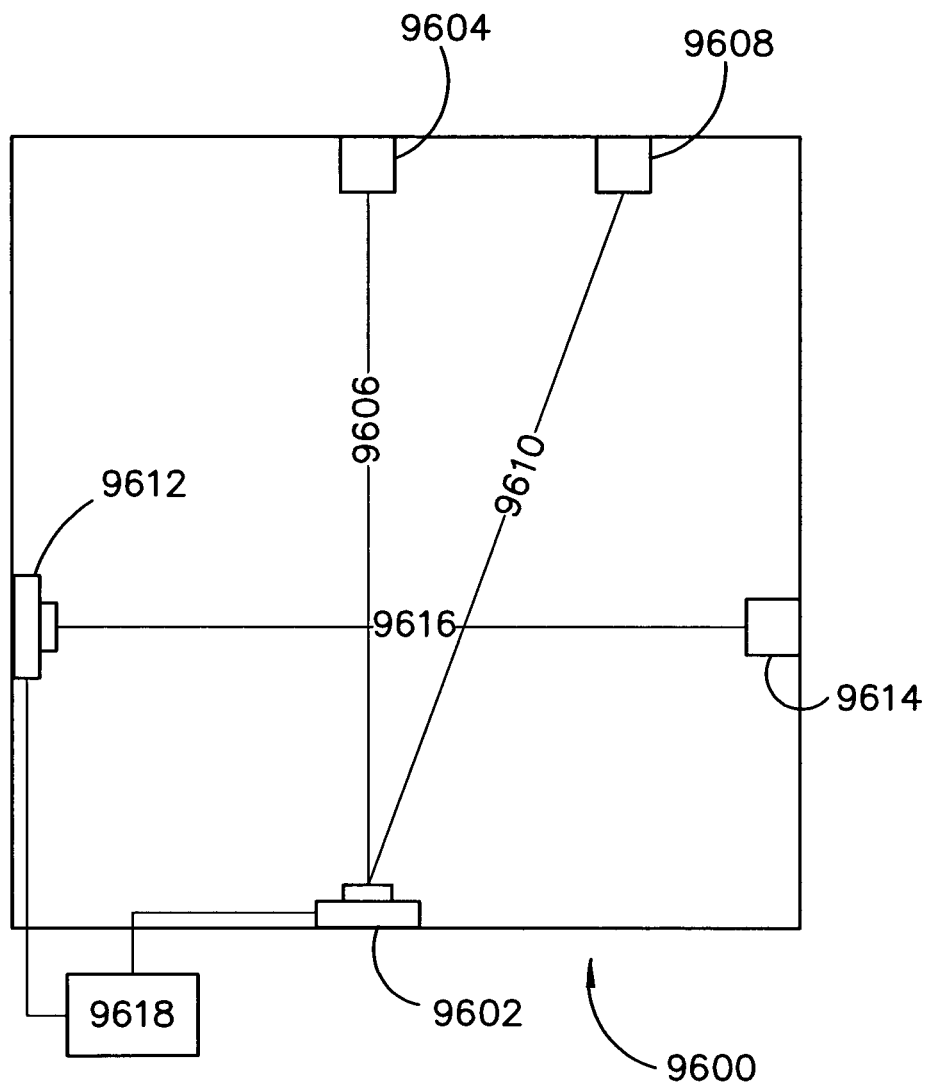
FIG. 96 illustrates a system made in accordance with a further embodiment of the present invention.

FIG. 96 illustrates a system according to a further embodiment of the present invention. In this system 9600 there is provided a first receiver 9602 which is associated with a pair of transmitters 9604 and 9608. The first transmitter 9604 transmits a first beam of light 9606, and the second transmitter 9608 transmits corresponding beam of light 9610. Both beams of light are received by the receiver 9602 and particle detection decisions can be made in accordance with embodiments of the invention described herein. The system 9600 additionally includes a receiver 9612 and associated transmitter 9614 which transmits a beam of light 9616. The beam 9616 is received by the receiver 9612 which can be adapted to determine the presence of particles as described elsewhere herein. The beam detector arrangement effectively provides three beam detectors that have beams that are coincident (or practically coincident) at two places. Both of the receivers 9602 and 9612 are connected to a controller 9618 which is adapted to apply fault and/or alarm logic to determine that the fault conditions and/or particle detection conditions exist. As will be appreciated, the intersecting beams 9606 and 9616, and 9610 and 9616 enable the system 9600 to determine whether particles have been detected at the points of intersection of the beams by correlations the outputs from the receivers 9602 and 9612. Such an arrangement also enables relatively advanced processing to be implemented and enables the particle detection algorithms of each of the individual beam detectors to differ from that used in a single stand alone beam detector. For example, a simple double knock system can be implemented in which at least two of the beams must detect particles above a predetermined threshold level before an alarm is raised. In a preferred form such a system may reduce overall false alarm rates as a false alarm condition is unlikely to occur in two different beams. However, this also permits a lower alarm threshold to be used, thus enabling faster detection of particles, without substantially affecting the false alarm rate of the system. In such a system, the false alarm probability of the entire system is the same as the product of the individual false alarm probabilities of the beams. As will be appreciated, both of the advantages of the above systems can be obtained to some extent by setting an alarm threshold which compromises between sensitivity and false alarm rate improvement. Moreover, temporal characteristics of the particle detection outputs of the various beam detectors can be used to improve particle detection performance or reduce false alarm occurrences. In this regard, the time separation between occurrences of suspected smoke events in each of the beams can be used to improve probability of early detection without increasing false alarm. For example, the time which each of a pair of substantially coincident beams goes into alarm, can be used to determine whether the alarm condition is caused by the presence of particles or a false alarm. If they are substantially coincident in time then the particle detection event is likely to be genuine. On the other hand, if the particle detection event occurs at substantially different times in each of the beams then this is likely to indicate a false alarm is present. In sophisticated systems it may be possible to compare time varying particle detection profiles from each of the beam detectors to identify corresponding particle detection events. For example, this could be done by cross correlating the outputs of a plurality of substantially coincident beam detectors within the system. In the event that high cross correlation between a pair of outputs is determined this can indicate that the output of each of the beam detectors are both experiencing similar conditions e.g. the same particle detection event or same false alarm event. A determination as to which type of event it is could be made by analysing the profiles e.g. a duration of obscuration; a level of obscuration; rate of change at the outset of observation etc to determine if the event is caused by the presence of particles or a foreign body.

It will be understood that the invention disclosed and defined in this specification extends to all alternative combinations of two or more of the individual features mentioned or evident from the text or drawings. All of these different combinations constitute various alternative aspects of the invention.

The invention claimed is:

1. A method performed by a beam detector system configured to detect particles in a monitored space, the method including:
generating with a light source at least one light beam having components in at least a first wavelength band and a second wavelength band such that the first wavelength band has a spatial intensity light profile across the width of the beam that is different to the spatial intensity profile in the second wavelength band;
receiving the at least one light source at an image sensor after the at least one beam traverses the monitored space;
generating output signals representing a level of received light at each of the first and second wavelengths within a region or regions within a field of view of the image sensor that include the light source;
receiving the output signals and determining at least partly on the basis of a relative reduction in the received light in the second wavelength band compared to the first wavelength band, from within the region or regions, that particles are impinging on the at least one beam;
wherein the spatial intensity profiles for the components of the beam in the first wavelength band and the second wavelength band are such that, in the event the light source moves out of alignment with the sensor, the level of light from the region or regions that is received by the image sensor in the first wavelength band decreases before the level of light received by the image sensor in the second wavelength band, thereby causing a relative change in received light level that is distinguishable from said relative reduction in the received light intensity in the second wavelength band compare to the first wavelength band caused by particles in the monitored space impinging on the at least one beam.

2. The method of claim 1 wherein the beam width of light in the first wavelength band is narrower than the beam width of light in the second wavelength band.

3. The method of claim 1 wherein light in a first wavelength band is at a longer wavelength than the second wavelength band.

4. The method of claim 1 wherein the light source includes a plurality of light emitters, each emitter being configured to emit light in one of the first and second wavelength bands.

5. The method of claim 4 wherein the plurality of light emitters includes a light emitter corresponding to one of the first or second wavelength bands arranged to surround one or more light emitters corresponding to the other of the first or second wavelength bands.

6. The method of claim 4 wherein plurality of light emitters comprise a plurality of semiconductor dies in a common light emitting diode (LED) package.

7. The method of claim 1 which includes a plurality of light sources arranged with respect to the image sensor, such that at least one beam from each light source is received at the image sensor after the at least one beam traverses the monitored space.

8. The method of claim 1 wherein the beam detector system is arranged to detect smoke.

* * * * *